(12) United States Patent
Meyers et al.

(10) Patent No.: US 7,071,004 B1
(45) Date of Patent: Jul. 4, 2006

(54) 14094, A NOVEL HUMAN TRYPSIN FAMILY MEMBER AND USES THEREOF

(75) Inventors: Rachel Meyers, Newton, MA (US); Kyle J. Macbeth, Boston, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/846,512

(22) Filed: May 1, 2001

Related U.S. Application Data

(63) Continuation-in-part of application No. 09/633,300, filed on Aug. 8, 2000, now abandoned.

(60) Provisional application No. 60/200,621, filed on Apr. 28, 2000.

(51) Int. Cl.
*G01N 33/53* (2006.01)
(52) U.S. Cl. ............... 436/501; 436/518; 435/7.1; 435/7.8
(58) Field of Classification Search ........... 530/350; 435/4, 72, 18, 23, 24, 195, 212, 7.1, 7.93; 436/501, 518
See application file for complete search history.

(56) References Cited

U.S. PATENT DOCUMENTS

| 5,223,409 | A | 6/1993 | Ladner et al. |
| 6,294,663 | B1 * | 9/2001 | O'Brien et al. ............ 536/23.5 |

FOREIGN PATENT DOCUMENTS

| WO | WO 92/20791 | 11/1992 |
| WO | WO 98/41656 | 9/1998 |
| WO | WO 99/46281 | 9/1999 |
| WO | WO 00/52044 | 9/2000 |
| WO | WO 00/53756 | 9/2000 |
| WO | WO 00/55350 | 9/2000 |
| WO | WO 00/68247 | 11/2000 |
| WO | WO 00/78960 | 12/2000 |
| WO | WO 01/22920 | 4/2001 |
| WO | WO 01/57194 | 8/2001 |
| WO | WO 01/68848 | 9/2001 |
| WO | WO 01/74897 | 10/2001 |
| WO | WO 01/96388 | 12/2001 |
| WO | WO 02/00860 | 1/2002 |

OTHER PUBLICATIONS

Underwood et al, Biochim Biophys Acta. Nov. 15, 2000; 1502(3):337-50.*
Scott et al (Nature Genetics, vol. 27, pp. 59-63).*
Bowie et al (Science, 1990, 247:1306-1310).*
Burgess et al (J of Cell Bio. 111:2129-2138, 1990).*
Lazar et al (Molecular and Cellular Biology, 1988, 8:1247-1252).*
Altschul et al., *J. Mol. Biol.*, 1990, 215:403-410.
Altschul et al., *Nucleic Acids Res.*, 1997, 25(17):3389-3402.
Chanda (ed.), *Current Protocols in Molecular Biology*, 2000, vol. 4, John Wiley & Sons, Inc. (Table of Contents Only).
Daly et al., "Three-dimensional structure of a cysteine-rich repeat from the low-density lipoprotein receptor," Biochemistry, vol. 92, pp. 6334-6338 (1995).
Fass et al., "Molecular basis of familial hypercholesteralaemia from structure of LDL receptor module," Nature, vol. 388, pp. 691-693 (1997).
GenBank Accession No. 015393; Paoloni-Giacobino et al., Created Jul. 15, 1998.
GenBank Accession No. A1978874; Washington University Sequencing Center; Aug. 30, 1999.
GenBank Accession No. AP001623; Shimizu et al., Submitted Apr. 4, 2000.
GenBank Accession No. AP001746; Hattori et al., Submitted Apr. 10, 2000.
Hohenester et al., "Crystal structure of a scavenger receptor cysteine-rich domain sheds light on an ancient superfamily," Nature Struc. Bio., vol. 6(3), pp. 228-232 (1999).
Karlin et al., *Proc. Natl. Acad. Sci. USA*, 1990, 87(6):2264-2268.
Karlin et al., *Proc. Natl. Acad. Sci. USA*, 1993, 90(12):5873-5877.
*Molecular Cloning—A Laboratory Manual*, 1989, 2$^{nd}$ Edition, Sambrook et al. (eds.), Cold Spring Harbor Laboratory Press (Table of Contents only).
Myers et al., *CABIOS*, 1988, 4:11-17.
Paolini-Giacobino et al., "Cloning of the TMPRSS2 Gene, which enclodes a novel serinve protease with transmembrane, LDLRA, and SRCR domains and maps to 21q22.3" Genomics, vol. 44, pp. 309-320 (1997).
Rawlings et al., "Evolutionary families of peptidases," Biochem. J., vol. 290, pp. 205-218 (1993).

(Continued)

*Primary Examiner*—Misook Yu
(74) *Attorney, Agent, or Firm*—Millennium Pharmaceuticals, Inc.

(57) ABSTRACT

The invention provides isolated nucleic acids molecules, designated 14094 nucleic acid molecules, which encode a novel trypsin family member. Elevated expression of 14094 mRNA was detected in breast, ovarian, lung, and liver cancers compared to normal cells derived from these tissues. The invention also provides antisense nucleic acid molecules, recombinant expression vectors containing 14094 nucleic acid molecules, host cells into which the expression vectors have been introduced, and nonhuman transgenic animals in which a 14094 gene has been introduced or disrupted. The invention still further provides isolated 14094 proteins, fusion proteins, antigenic peptides and anti-14094 antibodies. Therapeutic and diagnostic methods utilizing compositions of the invention to, for example, treat, prevent, and/or diagnose neoplastic conditions, are also provided.

11 Claims, 6 Drawing Sheets

OTHER PUBLICATIONS

Resnick et al., "The SRCR superfamily: a family reminiscent of the Ig superfamily," TIBS 19, pp. 5-8, Jan. 1994.
Sonnhammer et al., *Proteins*, 1997, 28(3):405-420.
Tanimoto et al., "Hepsin, a cell surface serine protease identified in hepatoma cells, is overexpressed in ovarian cancer," Cancer Research, vol. 57, pp. 2884-2887 (1997).
Torres-Rosado et al., "Hepsin, a putative cell-surface serine protease, is required for mammalian cell growth," Proc. Natl. Acad. Sci., vol. 90, pp. 7181-7185 (1993).
Weintraub et al., *Trends in Genetics*, Jan. 1985.
Sequence Alignment, us-09-633-300-1.rng, pp. 1-3.
Sequence Alignment, us-09-633-300-3.rng, pp. 1-3.
Ezzell, "Magic Bullets Fly Again", *Scientific American* 285:34-41 (2001).
Houghten et al., "The Use of Synthetic Peptide Combinatorial Libraries for the Identification of Bioactive Peptides", *BioTechniques* 13:412-421 (1992).
Kazama et al., "Hepsin, a Putative Membrane-associated Serine Protease, Activates Human Factor VII and Initiates a Pathway of Blood Coagulation on the Cell Surface Leading to Thrombin Formation", *J. Biol. Chem.* 270:66-72 (1995).
Vu et al., "Identification and Cloning of the Membrane-associated Serine Protease, Hepsin, from Mouse Preimplantation Embryos", *J. Biol. Chem.* 272:31315-31320 (1997).
Yamaoka et al., "Cloning and Characterization of the cDNA for Human Airway Trypsin-like Protease", *J. Biol. Chem.* 273:11895-11901 (1998).
Geneseq Accession No. AAZ233949; Record dated Dec. 7, 1999.
Geneseq Accession No. AAY41694; Record dated Dec. 7, 1999.
EMBL Accession No. AI469095; Record dated Mar. 17, 1999.
EMBL Accession No. AA922301; Record dated Apr. 24, 1998.
EMBL Accession No. AX340919; Abstract.
EMBL Accession No. AX341376; Abstract.
EMBL Accession No. AB038157; Record dated Jan. 08, 2001.
Underwood et al., "TADG12, a novel serine protease overexpressed in ovarian carcinoma", Proc. Am. Assoc. for Cancer Res. Annual 41:130 (2000).

* cited by examiner

```
trypsin: domain 1 of 1, from 217 to 443: score 293.0, E = 3.2e-92
                *->IvGGreaqpgsfgsPwqvslqvrsgggsrkhfCGGsLisenwVLTAA
                   IvGG +   ++ Pwq+slq+ +      +h+CGGs+i + w++TAA
     14094   217  IVGGNMSLLSQW--PWQASLQFQG-----YHLCGGSVITPLWIITAA  256

HCvsgaasapassvrVSlsvrlGehnlsltegteqkfdvkktiivHpnyn
                   HCv++      +++s+++       +G   +sl  +      v+k i+ H++y
     14094   257  HCVYD--LYLPKSWTI----QVGL--VSLLDNPAPSHLVEK-IVYHSKYK  297 pdtldngaYdnDiALlkLkspgvtlgdtvrpicLpsassdlpvGttctvs
                   p+  l+       nDiAL+kL++p +t+++  ++p+cLp +   ++p+G c+ s
     14094   298  PKRLG-----NDIALMKLAGP-LTFNEMIQPVCLPNSEENFPDGKVCWTS  341

GwGrrptknlg.lsdtLqevvvpvvsretCrsayeyggtdDkvefvtdnm
                   GwG    t+++g+ s +L ++ vp++s++ C+++    ygg     +++ m
     14094   342  GWGA--TEDGGdASPVLNHAAVPLISNKICNHRDVYGGI------ISPSM  383 iCagal.ggkdaCqGDSGGPLvcsdgnrdgrwelvGivSwGsygCargnk
                   +Cag+l+gg+d+CqGDSGGPLvc          w+lvG +S+G  gCa+ nk
     14094   384  LCAGYLtGGVDSCQGDSGGPLVCQER---RLWKLVGATSFG-IGCAEVNK  429

PGvytrVssyldWI<-*
                   PGvytrV+s+ldWI
     14094   430  PGVYTRVTSFLDWI     443
```

Fig. 2A

```
trypsin_2: domain 1 of 1, from 216 to 443: score 328.2, E = 9.2e-95
                *->RIVGGseakigsfPWqvsLq......CGGSLIsprwVLTAAHC....
                   RIVGG+ +   ++PWq+sLq ++ + CGGS+I+p w++TAAHC +
     14094   216     RIVGGNMSLLSQWPWQASLQfqgyhlCGGSVITPLWIITAAHCvydl  262

......rVrlGshdlssgeeteggprldspggqvikVskiievHpnYn..
                            +++ ++ +G +l +        + + V+ki+ H +Y ++
     14094   263  ylpkswTIQVGLVSLLDNP-----------APSHLVEKIV-YHSKYKpk  299

...NDIALLkLkepvtlsdsntvrPicLPssneiktsegntvpaGttctV
                        + +NDIAL+kL+ p+t+++  ++P+cLP+s         ++++p+G c+
     14094   300  rlgNDIALMKLAGPLTFNE--MIQPVCLPNS-------EENFPDGKVCWT  340 sGWGrtsegpeesgggslpdvLqevnvpivsnetCr............Ml
                   sGWG t++      gg + vL ++ vp++sn+ C++++  +++  +++Ml
     14094   341  SGWGATED------GGDASPVLNHAAVPLISNKICNhrdvyggiispsML  384

CAGyleggntpgGkDaCqGDSGGPLvc......vLvGiVSWGssslygCa
                   CAGyl+      gG+D+CqGDSGGPLvc++++ ++LvG +S+G    +gCa
     14094   385  CAGYLT-----GGVDSCQGDSGGPLVCqerrlwKLVGATSFG----IGCA  425 rpnkPGVYTrVssyldWI<-*
                   + nkPGVYTrV+s+ldWI
     14094   426  EVNKPGVYTRVTSFLDWI     443
```

Fig. 2B

```
BEGIN SEQ ID NO: 6 ─┐                           END SEQ ID NO: 6 ─┐
                    ▼                                             ▼
         *->stCggpdeFqCgsgrrCIprswvCDGdpDCeDGSDEslenCaa<-*
            +C+   ++++C+s+  CI    +CDG  DC+DG+DE    +C++
  14094  71    FDCS--GKYRCRSSFKCIELIARCDGVSDCKDGEDE--YRCVR   109
```

Fig. 3A

```
                 ┌─ BEGIN SEQ ID NO: 7
                 ▼
         *->vgGssrCeGrVEVrhdgskWgtVCdssWslrdanvdpQaskvCrqLG
            vgG  +++  +++V+   + W+t C+++W  + anv      +C+qLG
  14094  110    VGG--QNA-VLQVF-TAASWKTMCSDDWKGHYANV------ACAQLG  146

CGgavsll.gpyfseggqPagqreiwldgvnCsGnE...tsLsqCpvrvt
         +   vs+ +    s+ g      ++++++    +  ++++     +++
  14094  147 FPSYVSSDnLRVSSLEG------QFREEFVSIDHLlpdDKVTALHHS--  187 ppglsrqcshdgedagVvCs<-*
         ++   ++c    g+ + ++C▲_____ END SEQ ID NO: 7
  14094  188 -VYVREGCAS-GHVVTLQCT    205
```

Fig. 3B

SEQUENCE LISTING

```
<160> NUMBER OF SEQ ID NOS: 13

<210> SEQ ID NO 1
<211> LENGTH: 2948
<212> TYPE: DNA
<213> ORGANISM: Homo sapiens
<220> FEATURE:
<221> NAME/KEY: CDS
<222> LOCATION: (628)...(1986)
<220> FEATURE:
<221> NAME/KEY: misc_feature
<222> LOCATION: (1)...(2948)
<223> OTHER INFORMATION: n = A,T,C or G

<400> SEQUENCE: 1
aagagttgca tatcgcctcc catcaacaaa ctttccntgt atttccanac aatgtatttt      60
gtttgtcaaa tccagttttc ttgtaaacat tgggggtaa ataacagagg tggcttatga     120
gtatttcttc cagggtaaaa agcaaagaa ttccggtttt ctgtatcctt ttcacttact     180
gttacccact ttgcctcgtc ttcaccctgt ccaaacaccg gtctccaatt tgcccttcag    240
agaacttaag tcaaggagag ttgaaattca caggccaggg cacatctttt atttatttca    300
ttatgttggc caacagaact tgattgtaaa taataataaa gaaatctgtt atatactttc    360
caaactccaa aaaaaaccg gaattcagcc tggttaagtc caagctgaat tccgggtggg     420
ggaaggaccg ggcaccggac ggctcgggta ctttcgttct taattaggtc atgcccgtat    480
gagccaggaa agggctgtgt ttatgggaag ccagtaacac tgtggcctac tatctcttcc    540
gtggtgccat ctcatttttt gggactcggg aattatgagg tagaggtgga ggcggagccg   600
gatgtcagag gtcctgaaat agtcacc atg ggg gaa aat gat ccg cct gct gtt    654
                              Met Gly Glu Asn Asp Pro Pro Ala Val
                                1               5 gaa gcc ccc ttc tca ttc cga tcg ctt ttt ggc ctt gat gat ttg aaa      702
Glu Ala Pro Phe Ser Phe Arg Ser Leu Phe Gly Leu Asp Asp Leu Lys
 10              15                  20                  25 ata agt cct gtt gca cca gat gca gat gct gtt gct gca cag atc ctg      750
Ile Ser Pro Val Ala Pro Asp Ala Asp Ala Val Ala Ala Gln Ile Leu
                 30                  35                  40 tca ctg ctg cca ttg aag ttt ttt cca atc atc gtc att ggg atc att      798
Ser Leu Leu Pro Leu Lys Phe Phe Pro Ile Ile Val Ile Gly Ile Ile
             45                  50                  55 gca ttg ata tta gca ctg gcc att ggt ctg ggc atc cac ttc gac tgc      846
Ala Leu Ile Leu Ala Leu Ala Ile Gly Leu Gly Ile His Phe Asp Cys
         60                  65                  70
```

-continued

| | |
|---|---|
| tca ggg aag tac aga tgt cgc tca tcc ttt aag tgt atc gag ctg ata<br>Ser Gly Lys Tyr Arg Cys Arg Ser Ser Phe Lys Cys Ile Glu Leu Ile<br>75                       80                      85 | 894 |
| gct cga tgt gac gga gtc tcg gat tgc aaa gac ggg gag gac gag tac<br>Ala Arg Cys Asp Gly Val Ser Asp Cys Lys Asp Gly Glu Asp Glu Tyr<br>90                      95                   100               105 | 942 |
| cgc tgt gtc cgg gtg ggt ggt cag aat gcc gtg ctc cag gtg ttc aca<br>Arg Cys Val Arg Val Gly Gly Gln Asn Ala Val Leu Gln Val Phe Thr<br>                   110                   115                  120 | 990 |
| gct gct tcg tgg aag acc atg tgc tcc gat gac tgg aag ggt cac tac<br>Ala Ala Ser Trp Lys Thr Met Cys Ser Asp Asp Trp Lys Gly His Tyr<br>        125                   130                   135 | 1038 |
| gca aat gtt gcc tgt gcc caa ctg ggt ttc cca agc tat gtg agt tca<br>Ala Asn Val Ala Cys Ala Gln Leu Gly Phe Pro Ser Tyr Val Ser Ser<br>140                     145                   150 | 1086 |
| gat aac ctc aga gtg agc tcg ctg gag ggg cag ttc cgg gag gag ttt<br>Asp Asn Leu Arg Val Ser Ser Leu Glu Gly Gln Phe Arg Glu Glu Phe<br>       155                   160                   165 | 1134 |
| gtg tcc atc gat cac ctc ttg cca gat gac aag gtg act gca tta cac<br>Val Ser Ile Asp His Leu Leu Pro Asp Asp Lys Val Thr Ala Leu His<br>170                       175                   180               185 | 1182 |
| cac tca gta tat gtg agg gag gga tgt gcc tct ggc cac gtg gtt acc<br>His Ser Val Tyr Val Arg Glu Gly Cys Ala Ser Gly His Val Val Thr<br>                   190                   195                  200 | 1230 |
| ttg cag tgc aca gcc tgt ggt cat aga agg ggc tac agc tca cgc atc<br>Leu Gln Cys Thr Ala Cys Gly His Arg Arg Gly Tyr Ser Ser Arg Ile<br>        205                   210                   215 | 1278 |
| gtg ggt gga aac atg tcc ttg ctc tcg cag tgg ccc tgg cag gcc agc<br>Val Gly Gly Asn Met Ser Leu Leu Ser Gln Trp Pro Trp Gln Ala Ser<br>220                       225                   230 | 1326 |
| ctt cag ttc cag ggc tac cac ctg tgc ggg ggc tct gtc atc acg ccc<br>Leu Gln Phe Gln Gly Tyr His Leu Cys Gly Gly Ser Val Ile Thr Pro<br>       235                   240                   245 | 1374 |
| ctg tgg atc atc act gct gca cac tgt gtt tat gac ttg tac ctc ccc<br>Leu Trp Ile Ile Thr Ala Ala His Cys Val Tyr Asp Leu Tyr Leu Pro<br>250                       255                   260               265 | 1422 |
| aag tca tgg acc atc cag gtg ggt cta gtt tcc ctg ttg gac aat cca<br>Lys Ser Trp Thr Ile Gln Val Gly Leu Val Ser Leu Leu Asp Asn Pro<br>                   270                   275                  280 | 1470 |
| gcc cca tcc cac ttg gtg gag aag att gtc tac cac agc aag tac aag<br>Ala Pro Ser His Leu Val Glu Lys Ile Val Tyr His Ser Lys Tyr Lys<br>        285                   290                   295 | 1518 |
| cca aag agg ctg ggc aat gac atc gcc ctt atg aag ctg gcc ggg cca<br>Pro Lys Arg Leu Gly Asn Asp Ile Ala Leu Met Lys Leu Ala Gly Pro<br>300                       305                   310 | 1566 |
| ctc acg ttc aat gaa atg atc cag cct gtg tgc ctg ccc aac tct gaa<br>Leu Thr Phe Asn Glu Met Ile Gln Pro Val Cys Leu Pro Asn Ser Glu<br>       315                   320                   325 | 1614 |
| gag aac ttc ccc gat gga aaa gtg tgc tgg acg tca gga tgg ggg gcc<br>Glu Asn Phe Pro Asp Gly Lys Val Cys Trp Thr Ser Gly Trp Gly Ala<br>330                       335                   340               345 | 1662 |
| aca gag gat gga ggt gac gcc tcc cct gtc ctg aac cac gcg gcc gtc<br>Thr Glu Asp Gly Gly Asp Ala Ser Pro Val Leu Asn His Ala Ala Val<br>                   350                   355                  360 | 1710 |
| cct ttg att tcc aac aag atc tgc aac cac agg gac gtg tac ggt ggc<br>Pro Leu Ile Ser Asn Lys Ile Cys Asn His Arg Asp Val Tyr Gly Gly<br>        365                   370                   375 | 1758 |
| atc atc tcc ccc tcc atg ctc tgc gcg ggc tac ctg acg ggt ggc gtg<br>Ile Ile Ser Pro Ser Met Leu Cys Ala Gly Tyr Leu Thr Gly Gly Val<br>380                       385                   390 | 1806 |

```
gac agc tgc cag ggg gac agc ggg ggg ccc ctg gtg tgt caa gag agg      1854
Asp Ser Cys Gln Gly Asp Ser Gly Gly Pro Leu Val Cys Gln Glu Arg
    395                 400                 405 agg ctg tgg aag tta gtg gga gcg acc agc ttt ggc atc ggc tgc gca      1902
Arg Leu Trp Lys Leu Val Gly Ala Thr Ser Phe Gly Ile Gly Cys Ala
410                 415                 420                 425 gag gtg aac aag cct ggg gtg tac acc cgt gtc acc tcc ttc ctg gac      1950
Glu Val Asn Lys Pro Gly Val Tyr Thr Arg Val Thr Ser Phe Leu Asp
                430                 435                 440 tgg atc cac gag cag atg gag aga gac cta aaa acc tgaaaggaa            1996
Trp Ile His Glu Gln Met Glu Arg Asp Leu Lys Thr
                445                 450 ggggacaagt agccacctga gttcctgagg tgatgaagac agcccgatcc tccccctggac   2056 tcccgtgtag gaacctgcac acgagcagac acccttggag ctctgagttc cggcaccagt   2116
agcaggcccg aaagaggcac ccttccatct gattccagca caaccttcaa gctgcttttt   2176
gttttttgtt tttttgagat ggagtctcgc tctgttgccc aggctggagt gcagtggcga   2236
aatccctgct cactgcagcc tccgcttccc tggttcaagc gattctcttg cctcagcttc   2296
cccagtagct gggaccacag gtgcccgcca ccacacccaa ctaattttt tattttagt    2356 agagacaggg tttcaccatg ttggccaggc tgctctcaaa cccctgacct caaatgatgt   2416
gcctgcttca gcctcccaca gtgctgggat tacaggcatg gccaccacg cctagcctca    2476 cgctcctttc tgatcttcac taagaacaaa agaagcagca acttgcaagg gcggcctttc   2536
ccactggtcc atctggtttt ctctccaggg gtcttgcaaa attcctgacg agataagcag   2596
ttatgtgacc tcacgtgcaa agccaccaac agccactcag aaaagacgca ccagcccaga   2656
agtgcagaac tgcagtcact gcacgttttc atctctaggg accagaacca aacccaccct   2716
ttctacttcc aagacttatt ttcacatgtg gggaggttaa tctaggaatg actcgtttaa   2776
ggcctatttt catgatttct ttgtagcatt tggtgcttga cgtattattg tcctttgatt   2836
ccaaataata tgtttccttc cctcatwraa maaaaaaaaa aaaaaaarr rmrrssgcta   2896 vavmarktta gagaaaaaac ctacccacrc cttccccctg aamctraaam ya            2948
```

<210> SEQ ID NO 2
<211> LENGTH: 453
<212> TYPE: PRT
<213> ORGANISM: Homo sapiens

<400> SEQUENCE: 2

```
Met Gly Glu Asn Asp Pro Pro Ala Val Glu Ala Pro Phe Ser Phe Arg
 1               5                  10                  15

Ser Leu Phe Gly Leu Asp Asp Leu Lys Ile Ser Pro Val Ala Pro Asp
            20                  25                  30

Ala Asp Ala Val Ala Ala Gln Ile Leu Ser Leu Leu Pro Leu Lys Phe
        35                  40                  45

Phe Pro Ile Ile Val Ile Gly Ile Ala Leu Ile Leu Ala Leu Ala
    50                  55                  60

Ile Gly Leu Gly Ile His Phe Asp Cys Ser Gly Lys Tyr Arg Cys Arg
65                  70                  75                  80

Ser Ser Phe Lys Cys Ile Glu Leu Ile Ala Arg Cys Asp Gly Val Ser
                85                  90                  95

Asp Cys Lys Asp Gly Glu Asp Glu Tyr Arg Cys Val Arg Val Gly Gly
            100                 105                 110

Gln Asn Ala Val Leu Gln Val Phe Thr Ala Ala Ser Trp Lys Thr Met
        115                 120                 125
```

| Cys | Ser | Asp | Asp | Trp | Lys | Gly | His | Tyr | Ala | Asn | Val | Ala | Cys | Ala | Gln |
|---|---|---|---|---|---|---|---|---|---|---|---|---|---|---|---|
| | 130 | | | | 135 | | | | 140 | | | | | | |

| Leu | Gly | Phe | Pro | Ser | Tyr | Val | Ser | Ser | Asp | Asn | Leu | Arg | Val | Ser | Ser |
|---|---|---|---|---|---|---|---|---|---|---|---|---|---|---|---|
| 145 | | | | | 150 | | | | | 155 | | | | | 160 |

| Leu | Glu | Gly | Gln | Phe | Arg | Glu | Glu | Phe | Val | Ser | Ile | Asp | His | Leu | Leu |
|---|---|---|---|---|---|---|---|---|---|---|---|---|---|---|---|
| | | | | 165 | | | | | 170 | | | | 175 | | |

| Pro | Asp | Asp | Lys | Val | Thr | Ala | Leu | His | His | Ser | Val | Tyr | Val | Arg | Glu |
|---|---|---|---|---|---|---|---|---|---|---|---|---|---|---|---|
| | | 180 | | | | | 185 | | | | | 190 | | | |

| Gly | Cys | Ala | Ser | Gly | His | Val | Val | Thr | Leu | Gln | Cys | Thr | Ala | Cys | Gly |
|---|---|---|---|---|---|---|---|---|---|---|---|---|---|---|---|
| | | 195 | | | | | 200 | | | | | 205 | | | |

| His | Arg | Arg | Gly | Tyr | Ser | Ser | Arg | Ile | Val | Gly | Gly | Asn | Met | Ser | Leu |
|---|---|---|---|---|---|---|---|---|---|---|---|---|---|---|---|
| | 210 | | | | | 215 | | | | | 220 | | | | |

| Leu | Ser | Gln | Trp | Pro | Trp | Gln | Ala | Ser | Leu | Gln | Phe | Gln | Gly | Tyr | His |
|---|---|---|---|---|---|---|---|---|---|---|---|---|---|---|---|
| 225 | | | | | 230 | | | | | 235 | | | | | 240 |

| Leu | Cys | Gly | Gly | Ser | Val | Ile | Thr | Pro | Leu | Trp | Ile | Ile | Thr | Ala | Ala |
|---|---|---|---|---|---|---|---|---|---|---|---|---|---|---|---|
| | | | | 245 | | | | | 250 | | | | | 255 | |

| His | Cys | Val | Tyr | Asp | Leu | Tyr | Leu | Pro | Lys | Ser | Trp | Thr | Ile | Gln | Val |
|---|---|---|---|---|---|---|---|---|---|---|---|---|---|---|---|
| | | | 260 | | | | | 265 | | | | | 270 | | |

| Gly | Leu | Val | Ser | Leu | Leu | Asp | Asn | Pro | Ala | Pro | Ser | His | Leu | Val | Glu |
|---|---|---|---|---|---|---|---|---|---|---|---|---|---|---|---|
| | | 275 | | | | | 280 | | | | | 285 | | | |

| Lys | Ile | Val | Tyr | His | Ser | Lys | Tyr | Lys | Pro | Lys | Arg | Leu | Gly | Asn | Asp |
|---|---|---|---|---|---|---|---|---|---|---|---|---|---|---|---|
| | 290 | | | | | 295 | | | | | 300 | | | | |

| Ile | Ala | Leu | Met | Lys | Leu | Ala | Gly | Pro | Leu | Thr | Phe | Asn | Glu | Met | Ile |
|---|---|---|---|---|---|---|---|---|---|---|---|---|---|---|---|
| 305 | | | | | 310 | | | | | 315 | | | | | 320 |

| Gln | Pro | Val | Cys | Leu | Pro | Asn | Ser | Glu | Glu | Asn | Phe | Pro | Asp | Gly | Lys |
|---|---|---|---|---|---|---|---|---|---|---|---|---|---|---|---|
| | | | | 325 | | | | | 330 | | | | | 335 | |

| Val | Cys | Trp | Thr | Ser | Gly | Trp | Gly | Ala | Thr | Glu | Asp | Gly | Gly | Asp | Ala |
|---|---|---|---|---|---|---|---|---|---|---|---|---|---|---|---|
| | | | 340 | | | | | 345 | | | | | 350 | | |

| Ser | Pro | Val | Leu | Asn | His | Ala | Ala | Val | Pro | Leu | Ile | Ser | Asn | Lys | Ile |
|---|---|---|---|---|---|---|---|---|---|---|---|---|---|---|---|
| | 355 | | | | | 360 | | | | | 365 | | | | |

| Cys | Asn | His | Arg | Asp | Val | Tyr | Gly | Gly | Ile | Ile | Ser | Pro | Ser | Met | Leu |
|---|---|---|---|---|---|---|---|---|---|---|---|---|---|---|---|
| 370 | | | | | 375 | | | | | 380 | | | | | |

| Cys | Ala | Gly | Tyr | Leu | Thr | Gly | Gly | Val | Asp | Ser | Cys | Gln | Gly | Asp | Ser |
|---|---|---|---|---|---|---|---|---|---|---|---|---|---|---|---|
| 385 | | | | | 390 | | | | | 395 | | | | | 400 |

| Gly | Gly | Pro | Leu | Val | Cys | Gln | Glu | Arg | Arg | Leu | Trp | Lys | Leu | Val | Gly |
|---|---|---|---|---|---|---|---|---|---|---|---|---|---|---|---|
| | | | | 405 | | | | | 410 | | | | | 415 | |

| Ala | Thr | Ser | Phe | Gly | Ile | Gly | Cys | Ala | Glu | Val | Asn | Lys | Pro | Gly | Val |
|---|---|---|---|---|---|---|---|---|---|---|---|---|---|---|---|
| | | | 420 | | | | | 425 | | | | | 430 | | |

| Tyr | Thr | Arg | Val | Thr | Ser | Phe | Leu | Asp | Trp | Ile | His | Glu | Gln | Met | Glu |
|---|---|---|---|---|---|---|---|---|---|---|---|---|---|---|---|
| | | 435 | | | | | 440 | | | | | 445 | | | |

| Arg | Asp | Leu | Lys | Thr |
|---|---|---|---|---|
| | | | | 450 |

<210> SEQ ID NO 3
<211> LENGTH: 1362
<212> TYPE: DNA
<213> ORGANISM: Homo sapiens

<400> SEQUENCE: 3

| atgggggaaa | atgatccgcc | tgctgttgaa | gccccttct | cattccgatc | gcttttttggc | 60 |
|---|---|---|---|---|---|---|
| cttgatgatt | tgaaaataag | tcctgttgca | ccagatgcag | atgctgttgc | tgcacagatc | 120 |
| ctgtcactgc | tgccattgaa | gttttttcca | atcatcgtca | ttgggatcat | tgcattgata | 180 |
| ttagcactgg | ccattggtct | gggcatccac | ttcgactgct | cagggaagta | cagatgtcgc | 240 |

```
tcatcctttta agtgtatcga gctgatagct cgatgtgacg gagtctcgga ttgcaaagac    300
ggggaggacg agtaccgctg tgtccgggtg ggtggtcaga atgccgtgct ccaggtgttc    360
acagctgctt cgtggaagac catgtgctcc gatgactgga agggtcacta cgcaaatgtt    420
gcctgtgccc aactgggttt cccaagctat gtgagttcag ataacctcag agtgagctcg    480
ctggagggc agttccggga ggagtttgtg tccatcgatc acctcttgcc agatgacaag    540
gtgactgcat acaccactc agtatatgtg agggagggat gtgcctctgg ccacgtggtt    600
accttgcagt gcacagcctg tggtcataga aggggctaca gctcacgcat cgtgggtgga    660
aacatgtcct tgctctcgca gtggccctgg caggccagcc ttcagttcca gggctaccac    720
ctgtgcgggg gctctgtcat cacgcccctg tggatcatca ctgctgcaca ctgtgtttat    780
gacttgtacc tccccaagtc atggaccatc caggtgggtc tagtttccct gttggacaat    840
ccagccccat cccacttggt ggagaagatt gtctaccaca gcaagtacaa gccaaagagg    900
ctgggcaatg acatcgccct tatgaagctg gccgggccac tcacgttcaa tgaaatgatc    960
cagcctgtgt gcctgcccaa ctctgaagag aacttccccg atggaaaagt gtgctggacg   1020
tcaggatggg gggccacaga ggatggaggt gacgcctccc ctgtcctgaa ccacgcggcc   1080
gtcccttga tttccaacaa gatctgcaac cacagggacg tgtacggtgg catcatctcc   1140
ccctccatgc tctgcgcggg ctacctgacg ggtggcgtgg acagctgcca ggggacagc   1200
ggggggcccc tggtgtgtca agagaggagg ctgtggaagt tagtgggagc gaccagcttt   1260
ggcatcggct gcgcagaggt gaacaagcct ggggtgtaca cccgtgtcac ctccttcctg   1320
gactggatcc acgagcagat ggagagagac ctaaaaacct ga                      1362
```

<210> SEQ ID NO 4
<211> LENGTH: 260
<212> TYPE: PRT
<213> ORGANISM: Artificial Sequence
<220> FEATURE:
<223> OTHER INFORMATION: consensus sequence

<400> SEQUENCE: 4

```
Ile Val Gly Gly Arg Glu Ala Gln Pro Gly Ser Phe Gly Ser Pro Trp
 1               5                  10                  15

Gln Val Ser Leu Gln Val Arg Ser Gly Gly Ser Arg Lys His Phe
                20                  25                  30

Cys Gly Gly Ser Leu Ile Ser Glu Asn Trp Val Leu Thr Ala Ala His
             35                  40                  45

Cys Val Ser Gly Ala Ala Ser Ala Pro Ala Ser Ser Val Arg Val Ser
         50                  55                  60

Leu Ser Arg Val Arg Leu Gly Glu His Asn Leu Ser Leu Thr Glu Gly
 65                  70                  75                  80

Thr Glu Gln Lys Phe Asp Val Lys Lys Thr Ile Val His Pro Asn
                 85                  90                  95

Tyr Asn Pro Asp Thr Leu Asp Asn Gly Ala Tyr Asp Asn Asp Ile Ala
                100                 105                 110

Leu Leu Lys Leu Lys Ser Pro Gly Val Thr Leu Gly Asp Thr Val Arg
             115                 120                 125

Pro Ile Cys Leu Pro Ser Ala Ser Ser Asp Leu Pro Val Gly Thr Thr
         130                 135                 140

Cys Thr Val Ser Gly Trp Gly Arg Arg Pro Thr Lys Asn Leu Gly Leu
145                 150                 155                 160
```

```
Ser Asp Thr Leu Gln Glu Val Val Pro Val Val Ser Arg Glu Thr
            165                 170                 175

Cys Arg Ser Ala Tyr Glu Tyr Gly Gly Thr Asp Lys Val Glu Phe
            180                 185                 190

Val Thr Asp Asn Met Ile Cys Ala Gly Ala Leu Gly Gly Lys Asp Ala
            195                 200                 205

Cys Gln Gly Asp Ser Gly Gly Pro Leu Val Cys Ser Asp Gly Asn Arg
210                 215                 220

Asp Gly Arg Trp Glu Leu Val Gly Ile Val Ser Trp Gly Ser Tyr Gly
225                 230                 235                 240

Cys Ala Arg Gly Asn Lys Pro Gly Val Tyr Thr Arg Val Ser Ser Tyr
            245                 250                 255

Leu Asp Trp Ile
            260

<210> SEQ ID NO 5
<211> LENGTH: 226
<212> TYPE: PRT
<213> ORGANISM: Artificial Sequence
<220> FEATURE:
<223> OTHER INFORMATION: consensus sequence

<400> SEQUENCE: 5

Arg Ile Val Gly Gly Ser Glu Ala Lys Ile Gly Ser Phe Pro Trp Gln
 1               5                  10                  15

Val Ser Leu Gln Cys Gly Gly Ser Leu Ile Ser Pro Arg Trp Val Leu
            20                  25                  30

Thr Ala Ala His Cys Arg Val Arg Leu Gly Ser His Asp Leu Ser Ser
            35                  40                  45

Gly Glu Glu Thr Glu Gly Gly Pro Arg Leu Asp Ser Pro Gly Gly Gln
    50                  55                  60

Val Ile Lys Val Ser Lys Ile Ile Glu Val His Pro Asn Tyr Asn Asn
65                  70                  75                  80

Asp Ile Ala Leu Leu Lys Leu Lys Glu Pro Val Thr Leu Ser Asp Ser
                85                  90                  95

Asn Thr Val Arg Pro Ile Cys Leu Pro Ser Ser Asn Glu Ile Lys Thr
            100                 105                 110

Ser Glu Gly Asn Thr Val Pro Ala Gly Thr Thr Cys Thr Val Ser Gly
            115                 120                 125

Trp Gly Arg Thr Ser Glu Gly Pro Glu Glu Ser Gly Gly Gly Ser Leu
130                 135                 140

Pro Asp Val Leu Gln Glu Val Asn Val Pro Ile Val Ser Asn Glu Thr
145                 150                 155                 160

Cys Arg Met Leu Cys Ala Gly Tyr Leu Glu Gly Gly Asn Thr Pro Gly
                165                 170                 175

Gly Lys Asp Ala Cys Gln Gly Asp Ser Gly Gly Pro Leu Val Cys Val
            180                 185                 190

Leu Val Gly Ile Val Ser Trp Gly Ser Ser Ser Leu Tyr Gly Cys Ala
            195                 200                 205

Arg Pro Asn Lys Pro Gly Val Tyr Thr Arg Val Ser Ser Tyr Leu Asp
            210                 215                 220

Trp Ile
225
```

```
<210> SEQ ID NO 6
<211> LENGTH: 43
<212> TYPE: PRT
<213> ORGANISM: Artificial Sequence
<220> FEATURE:
<223> OTHER INFORMATION: consensus sequence

<400> SEQUENCE: 6

Ser Thr Cys Gly Gly Pro Asp Glu Phe Gln Cys Gly Ser Gly Arg Arg
 1               5                  10                  15

Cys Ile Pro Arg Ser Trp Val Cys Asp Gly Asp Pro Asp Cys Glu Asp
             20                  25                  30

Gly Ser Asp Glu Ser Leu Glu Asn Cys Ala Ala
         35                  40

<210> SEQ ID NO 7
<211> LENGTH: 113
<212> TYPE: PRT
<213> ORGANISM: Artificial Sequence
<220> FEATURE:
<223> OTHER INFORMATION: consensus sequence

<400> SEQUENCE: 7

Val Gly Gly Ser Ser Arg Cys Glu Gly Arg Val Glu Val Arg His Asp
 1               5                  10                  15

Gly Ser Lys Trp Gly Thr Val Cys Asp Ser Ser Trp Ser Leu Arg Asp
             20                  25                  30

Ala Asn Val Asp Pro Gln Ala Ser Lys Val Cys Arg Gln Leu Gly Cys
         35                  40                  45

Gly Gly Ala Val Ser Leu Leu Gly Pro Tyr Phe Ser Glu Gly Gly Gly
     50                  55                  60

Pro Ala Gly Gln Arg Glu Ile Trp Leu Asp Gly Val Asn Cys Ser Gly
65                  70                  75                  80

Asn Glu Thr Ser Leu Ser Gln Cys Pro Val Arg Val Thr Pro Pro Gly
                 85                  90                  95

Leu Ser Arg Gln Cys Ser His Asp Gly Glu Asp Ala Gly Val Val Cys
             100                 105                 110

Ser

<210> SEQ ID NO 8
<211> LENGTH: 5
<212> TYPE: PRT
<213> ORGANISM: Homo sapiens

<400> SEQUENCE: 8

Arg Ile Val Gly Gly
 1               5

<210> SEQ ID NO 9
<211> LENGTH: 5
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: 2
<223> OTHER INFORMATION: Xaa = Asp or Glu
<220> FEATURE:
<221> NAME/KEY: VARIANT
<222> LOCATION: 5
<223> OTHER INFORMATION: Xaa = Gly or Ser
```

```
<400> SEQUENCE: 9

Gly Xaa Ser Gly Xaa
 1               5

<210> SEQ ID NO 10
<211> LENGTH: 6
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: 1
<223> OTHER INFORMATION: Xaa = Leu, Ile, Val, or Met
<220> FEATURE:
<221> NAME/KEY: VARIANT
<222> LOCATION: 2
<223> OTHER INFORMATION: Xaa = Ser or Thr
<220> FEATURE:
<221> NAME/KEY: VARIANT
<222> LOCATION: 4
<223> OTHER INFORMATION: Xaa = Ser, Thr, Ala, or Gly

<400> SEQUENCE: 10

Xaa Xaa Ala Xaa His Cys
 1               5

<210> SEQ ID NO 11
<211> LENGTH: 2951
<212> TYPE: DNA
<213> ORGANISM: Homo sapiens
<220> FEATURE:
<221> NAME/KEY: CDS
<222> LOCATION: (628)...(1989)
<220> FEATURE:
<221> NAME/KEY: misc_feature
<222> LOCATION: (1)...(2951)
<223> OTHER INFORMATION: n = A,T,C or G

<400> SEQUENCE: 11
```

| | | | | |
|---|---|---|---|---|
| aagagttgca | tatcgcctcc | catcaacaaa | ctttccntgt | atttccanac | aatgtatttt | 60 |
| gtttgtcaaa | tccagttttc | ttgtaaagat | tgggggtaa | ataacagagg | tggcttatga | 120 |
| gtatttcttc | cagggtaaaa | agcaaaagaa | ttccggtttt | ctgtatcctt | ttcacttact | 180 |
| gttaccact | ttgcctcgtc | ttcaccctgt | ccaaacaccg | gtctccaatt | tgcccttcag | 240 |
| agaacttaag | tcaaggagag | ttgaaattca | caggccaggg | cacatctttt | atttattca | 300 |
| ttatgttggc | caacagaact | tgattgtaaa | taataataaa | gaaatctgtt | atatactttc | 360 |
| caaactccaa | aaaaaaccg | gaattcagcc | tggttaagtc | caagctgaat | tccggtgggg | 420 |
| ggaaggaccg | ggcaccggac | ggctcgggta | ctttcgttct | taattaggtc | atgcccgtat | 480 |
| gagccaggaa | agggctgtgt | ttatgggaag | ccagtaacac | tgtggcctac | tatctcttcc | 540 |
| gtggtgccat | ctacattttt | gggactcggg | aattatgagg | tagaggtgga | ggcggagccg | 600 |

```
gatgtcagag gtcctgaaat agtcacc atg ggg gaa aat gat ccg cct gct gtt       654
                                 Met Gly Glu Asn Asp Pro Pro Ala Val
                                  1               5 gaa gcc ccc ttc tca ttc cga tcg ctt ttt ggc ctt gat gat ttg aaa         702
Glu Ala Pro Phe Ser Phe Arg Ser Leu Phe Gly Leu Asp Asp Leu Lys
      10              15                  20                  25 ata agt cct gtt gca cca gat gca gat gct gtt gct gca cag atc ctg         750
Ile Ser Pro Val Ala Pro Asp Ala Asp Ala Val Ala Ala Gln Ile Leu
              30                  35                  40
```

-continued

| | | |
|---|---|---|
| tca ctg ctg cca ttg aag ttt ttt cca atc atc gtc att ggg atc att<br>Ser Leu Leu Pro Leu Lys Phe Phe Pro Ile Ile Val Ile Gly Ile Ile<br>              45                        50                        55 | | 798 |
| gca ttg ata tta gca ctg gcc att ggt ctg ggc atc cac ttc gac tgc<br>Ala Leu Ile Leu Ala Leu Ala Ile Gly Leu Gly Ile His Phe Asp Cys<br>        60                        65                        70 | | 846 |
| tca ggg aag tac aga tgt cgc tca tcc ttt aag tgt atc gag ctg ata<br>Ser Gly Lys Tyr Arg Cys Arg Ser Ser Phe Lys Cys Ile Glu Leu Ile<br>75                        80                        85 | | 894 |
| gct cga tgt gac gga gtc tcg gat tgc aaa gac ggg gag gac gag tac<br>Ala Arg Cys Asp Gly Val Ser Asp Cys Lys Asp Gly Glu Asp Glu Tyr<br>90                        95                        100                      105 | | 942 |
| cgc tgt gtc cgg gtg ggt ggt cag aat gcc gtg ctc cag gtg ttc aca<br>Arg Cys Val Arg Val Gly Gly Gln Asn Ala Val Leu Gln Val Phe Thr<br>                        110                        115                      120 | | 990 |
| gct gct tcg tgg aag acc atg tgc tcc gat gac tgg aag ggt cac tac<br>Ala Ala Ser Trp Lys Thr Met Cys Ser Asp Asp Trp Lys Gly His Tyr<br>                  125                        130                      135 | | 1038 |
| gca aat gtt gcc tgt gcc caa ctg ggt ttc cca agc tat gtg agt tca<br>Ala Asn Val Ala Cys Ala Gln Leu Gly Phe Pro Ser Tyr Val Ser Ser<br>        140                        145                        150 | | 1086 |
| gat aac ctc aga gtg agc tcg ctg gag ggg cag ttc cgg gag gag ttt<br>Asp Asn Leu Arg Val Ser Ser Leu Glu Gly Gln Phe Arg Glu Glu Phe<br>155                        160                        165 | | 1134 |
| gtg tcc atc gat cac ctc ttg cca gat gac aag gtg act gca tta cac<br>Val Ser Ile Asp His Leu Leu Pro Asp Asp Lys Val Thr Ala Leu His<br>170                        175                        180                      185 | | 1182 |
| cac tca gta tat gtg agg gag gga tgt gcc tct ggc cac gtg gtt acc<br>His Ser Val Tyr Val Arg Glu Gly Cys Ala Ser Gly His Val Val Thr<br>                        190                        195                      200 | | 1230 |
| ttg cag tgc aca gcc tgt ggt cat aga agg ggc tac agc tca cgc atc<br>Leu Gln Cys Thr Ala Cys Gly His Arg Arg Gly Tyr Ser Ser Arg Ile<br>                  205                        210                      215 | | 1278 |
| gtg ggt gga aac atg tcc ttg ctc tcg cag tgg ccc tgg cag gcc agc<br>Val Gly Gly Asn Met Ser Leu Leu Ser Gln Trp Pro Trp Gln Ala Ser<br>        220                        225                        230 | | 1326 |
| ctt cag ttc cag ggc tac cac ctg tgc ggg ggc tct gtc atc acg ccc<br>Leu Gln Phe Gln Gly Tyr His Leu Cys Gly Gly Ser Val Ile Thr Pro<br>235                        240                        245 | | 1374 |
| ctg tgg atc atc act gct gca cac tgt gtt tat gac ttg tac ctc ccc<br>Leu Trp Ile Ile Thr Ala Ala His Cys Val Tyr Asp Leu Tyr Leu Pro<br>250                        255                        260                      265 | | 1422 |
| aag tca tgg acc atc cag gtg ggt cta gtt tcc ctg ttg gac aat cca<br>Lys Ser Trp Thr Ile Gln Val Gly Leu Val Ser Leu Leu Asp Asn Pro<br>                        270                        275                      280 | | 1470 |
| gcc cca tcc cac ttg gtg gag aag att gtc tac cac agc aag tac aag<br>Ala Pro Ser His Leu Val Glu Lys Ile Val Tyr His Ser Lys Tyr Lys<br>                  285                        290                      295 | | 1518 |
| cca aag agg ctg ggc aat gac atc gcc ctt atg aag ctg gcc ggg cca<br>Pro Lys Arg Leu Gly Asn Asp Ile Ala Leu Met Lys Leu Ala Gly Pro<br>        300                        305                        310 | | 1566 |
| ctc acg ttc aat gaa atg atc cag cct gtg tgc ctg ccc aac tct gaa<br>Leu Thr Phe Asn Glu Met Ile Gln Pro Val Cys Leu Pro Asn Ser Glu<br>315                        320                        325 | | 1614 |
| gag aac ttc ccc gat gga aaa gtg tgc tgg acg tca gga tgg ggg gcc<br>Glu Asn Phe Pro Asp Gly Lys Val Cys Trp Thr Ser Gly Trp Gly Ala<br>330                        335                        340                      345 | | 1662 |
| aca gag gat gga gca ggt gac gcc tcc cct gtc ctg aac cac gcg gcc<br>Thr Glu Asp Gly Ala Gly Asp Ala Ser Pro Val Leu Asn His Ala Ala<br>                        350                        355                      360 | | 1710 |

| | | | | | | | | | | | | | | | |
|---|---|---|---|---|---|---|---|---|---|---|---|---|---|---|---|
| gtc | cct | ttg | att | tcc | aac | aag | atc | tgc | aac | cac | agg | gac | gtg | tac | ggt | 1758
| Val | Pro | Leu | Ile | Ser | Asn | Lys | Ile | Cys | Asn | His | Arg | Asp | Val | Tyr | Gly |
| | | 365 | | | | | 370 | | | | | 375 | | | |

```
gtc cct ttg att tcc aac aag atc tgc aac cac agg gac gtg tac ggt    1758
Val Pro Leu Ile Ser Asn Lys Ile Cys Asn His Arg Asp Val Tyr Gly
        365                 370                 375 ggc atc atc tcc ccc tcc atg ctc tgc gcg ggc tac ctg acg ggt ggc    1806
Gly Ile Ile Ser Pro Ser Met Leu Cys Ala Gly Tyr Leu Thr Gly Gly
            380                 385                 390 gtg gac agc tgc cag ggg gac agc ggg ggg ccc ctg gtg tgt caa gag    1854
Val Asp Ser Cys Gln Gly Asp Ser Gly Gly Pro Leu Val Cys Gln Glu
        395                 400                 405 agg agg ctg tgg aag tta gtg gga gcg acc agc ttt ggc atc ggc tgc    1902
Arg Arg Leu Trp Lys Leu Val Gly Ala Thr Ser Phe Gly Ile Gly Cys
410                 415                 420                 425 gca gag gtg aac aag cct ggg gtg tac acc cgt gtc acc tcc ttc ctg    1950
Ala Glu Val Asn Lys Pro Gly Val Tyr Thr Arg Val Thr Ser Phe Leu
                430                 435                 440 gac tgg atc cac gag cag atg gag aga gac cta aaa acc tgaagaggaa     1999
Asp Trp Ile His Glu Gln Met Glu Arg Asp Leu Lys Thr
            445                 450
```

| | | |
|---|---|---|
| ggggacaagt agccacctga gttcctgagg tgatgaagac agcccgatcc tcccctggac | 2059 |
| tcccgtgtag gaacctgcac acgagcagac acccttggag ctctgagttc cggcaccagt | 2119 |
| agcaggcccg aaagaggcac ccttccatct gattccagca caaccttcaa gctgcttttt | 2179 |
| gttttttgtt tttttgagat ggagtctcgc tctgttgccc aggctggagt gcagtggcga | 2239 |
| aatccctgct cactgcagcc tccgcttccc tggttcaagc gattctcttg cctcagcttc | 2299 |
| cccagtagct gggaccacag gtgcccgcca ccacacccaa ctaattttg tatttttagt | 2359 |
| agagacaggg tttcaccatg ttggccaggc tgctctcaaa ccctgacct caaatgatgt | 2419 |
| gcctgcttca gcctcccaca gtgctgggat tacaggcatg gccaccacg cctagcctca | 2479 |
| cgctcctttc tgatcttcac taagaacaaa agaagcagca acttgcaagg gcggcctttc | 2539 |
| ccactggtcc atctggtttt ctctccaggg gtcttgcaaa attcctgacg agataagcag | 2599 |
| ttatgtgacc tcacgtgcaa agccaccaac agccactcag aaaagacgca ccagcccaga | 2659 |
| agtgcagaac tgcagtcact gcacgttttc atctctaggg accagaacca aacccaccct | 2719 |
| ttctacttcc aagacttatt ttcacatgtg gggaggttaa tctaggaatg actcgtttaa | 2779 |
| ggcctatttt catgatttct ttgtagcatt tggtgcttga cgtattattg tcctttgatt | 2839 |
| ccaaataata tgtttccttc cctcatwraa maaaaaaaa aaaaaaaarr rmrrssgcta | 2899 |
| vavmarktta gagaaaaaac ctacccacrc cttccccctg aamctraaam ya | 2951 |

<210> SEQ ID NO 12
<211> LENGTH: 454
<212> TYPE: PRT
<213> ORGANISM: Homo sapiens

<400> SEQUENCE: 12

```
Met Gly Glu Asn Asp Pro Pro Ala Val Glu Ala Pro Phe Ser Phe Arg
1               5                   10                  15

Ser Leu Phe Gly Leu Asp Asp Leu Lys Ile Ser Pro Val Ala Pro Asp
            20                  25                  30

Ala Asp Ala Val Ala Ala Gln Ile Leu Ser Leu Leu Pro Leu Lys Phe
        35                  40                  45

Phe Pro Ile Ile Val Ile Gly Ile Ile Ala Leu Ile Leu Ala Leu Ala
    50                  55                  60

Ile Gly Leu Gly Ile His Phe Asp Cys Ser Gly Lys Tyr Arg Cys Arg
65                  70                  75                  80
```

```
Ser Ser Phe Lys Cys Ile Glu Leu Ile Ala Arg Cys Asp Gly Val Ser
            85                  90                  95

Asp Cys Lys Asp Gly Glu Asp Glu Tyr Arg Cys Val Arg Val Gly Gly
            100                 105                 110

Gln Asn Ala Val Leu Gln Val Phe Thr Ala Ala Ser Trp Lys Thr Met
            115                 120                 125

Cys Ser Asp Asp Trp Lys Gly His Tyr Ala Asn Val Ala Cys Ala Gln
            130                 135                 140

Leu Gly Phe Pro Ser Tyr Val Ser Ser Asp Asn Leu Arg Val Ser Ser
145                 150                 155                 160

Leu Glu Gly Gln Phe Arg Glu Glu Phe Val Ser Ile Asp His Leu Leu
            165                 170                 175

Pro Asp Asp Lys Val Thr Ala Leu His His Ser Val Tyr Val Arg Glu
            180                 185                 190

Gly Cys Ala Ser Gly His Val Val Thr Leu Gln Cys Thr Ala Cys Gly
            195                 200                 205

His Arg Arg Gly Tyr Ser Ser Arg Ile Val Gly Gly Asn Met Ser Leu
            210                 215                 220

Leu Ser Gln Trp Pro Trp Gln Ala Ser Leu Gln Phe Gln Gly Tyr His
225                 230                 235                 240

Leu Cys Gly Gly Ser Val Ile Thr Pro Leu Trp Ile Ile Thr Ala Ala
                245                 250                 255

His Cys Val Tyr Asp Leu Tyr Leu Pro Lys Ser Trp Thr Ile Gln Val
            260                 265                 270

Gly Leu Val Ser Leu Leu Asp Asn Pro Ala Pro Ser His Leu Val Glu
            275                 280                 285

Lys Ile Val Tyr His Ser Lys Tyr Lys Pro Lys Arg Leu Gly Asn Asp
290                 295                 300

Ile Ala Leu Met Lys Leu Ala Gly Pro Leu Thr Phe Asn Glu Met Ile
305                 310                 315                 320

Gln Pro Val Cys Leu Pro Asn Ser Glu Glu Asn Phe Pro Asp Gly Lys
            325                 330                 335

Val Cys Trp Thr Ser Gly Trp Gly Ala Thr Glu Asp Gly Ala Gly Asp
            340                 345                 350

Ala Ser Pro Val Leu Asn His Ala Ala Val Pro Leu Ile Ser Asn Lys
            355                 360                 365

Ile Cys Asn His Arg Asp Val Tyr Gly Gly Ile Ile Ser Pro Ser Met
            370                 375                 380

Leu Cys Ala Gly Tyr Leu Thr Gly Gly Val Asp Ser Cys Gln Gly Asp
385                 390                 395                 400

Ser Gly Gly Pro Leu Val Cys Gln Glu Arg Arg Leu Trp Lys Leu Val
                405                 410                 415

Gly Ala Thr Ser Phe Gly Ile Gly Cys Ala Glu Val Asn Lys Pro Gly
            420                 425                 430

Val Tyr Thr Arg Val Thr Ser Phe Leu Asp Trp Ile His Glu Gln Met
            435                 440                 445

Glu Arg Asp Leu Lys Thr
            450

<210> SEQ ID NO 13
<211> LENGTH: 1365
<212> TYPE: DNA
<213> ORGANISM: Homo sapiens
```

-continued

```
<400> SEQUENCE: 13
atgggggaaa atgatccgcc tgctgttgaa gcccccttct cattccgatc gcttttggc      60 cttgatgatt tgaaaataag tcctgttgca ccagatgcag atgctgttgc tgcacagatc    120
ctgtcactgc tgccattgaa gttttttcca atcatcgtca ttgggatcat tgcattgata    180
ttagcactgg ccattggtct gggcatccac ttcgactgct cagggaagta cagatgtcgc    240
tcatccttta agtgtatcga gctgatagct cgatgtgacg gagtctcgga ttgcaaagac    300
ggggaggacg agtaccgctg tgtccgggtg ggtggtcaga atgccgtgct ccaggtgttc    360
acagctgctt cgtggaagac catgtgctcc gatgactgga agggtcacta cgcaaatgtt    420
gcctgtgccc aactgggttt cccaagctat gtgagttcag ataacctcag agtgagctcg    480
ctggaggggc agttccggga ggagtttgtg tccatcgatc acctcttgcc agatgacaag    540
gtgactgcat acaccactc agtatatgtg agggagggat gtgcctctgg ccacgtggtt     600
accttgcagt gcacagcctg tggtcataga aggggctaca gctcacgcat cgtgggtgga    660
aacatgtcct tgctctcgca gtggccctgg caggccagcc ttcagttcca gggctaccac    720
ctgtgcgggg gctctgtcat cacgcccctg tggatcatca ctgctgcaca ctgtgtttat    780
gacttgtacc tccccaagtc atggaccatc caggtgggtc tagtttccct gttggacaat    840
ccagccccat cccacttggt ggagaagatt gtctaccaca gcaagtacaa gccaaagagg    900
ctgggcaatg acatcgccct tatgaagctg gccgggccac tcacgttcaa tgaaatgatc    960
cagcctgtgt gcctgcccaa ctctgaagag aacttccccg atggaaaagt gtgctggacg   1020
tcaggatggg gggccacaga ggatggagca ggtgacgcct ccctgtcct gaaccacgcg    1080 gccgtccctt tgatttccaa caagatctgc aaccacaggg acgtgtacgg tggcatcatc   1140
tccccctcca tgctctgcgc gggctacctg acgggtggcg tggacagctg ccaggggac   1200 agcgggggc ccctggtgtg tcaagagagg aggctgtgga agttagtggg agcgaccagc   1260
tttggcatcg gctgcgcaga ggtgaacaag cctggggtgt acaccgtgt cacctccttc    1320 ctggactgga tccacgagca gatggagaga gacctaaaaa cctga                 1365
```

14094, A NOVEL HUMAN TRYPSIN FAMILY MEMBER AND USES THEREOF

RELATED APPLICATIONS

This application is a continuation-in-part of application Ser. No. 09/633,300, filed 8 Aug. 2000 now abandoned, which claims the benefit of U.S. Provisional Patent Application No. 60/200,621, filed Apr. 28, 2000, and U.S. patent application Ser. No. 09/633,300, filed Aug. 8, 2000, the contents of which are hereby incorporated by reference.

BACKGROUND OF THE INVENTION

Four major classes of proteases are known and are designated by the principal functional group in their active site: serine, thiol, carboxyl, and metallo. Serine proteases are characterized by the presence of a unique serine residue that functions as a nucleophile to cleave peptide bonds. In some cases, the serine forms covalent adducts with substrates and inhibitors. The serine functions with two other principal residues of the active site, a histidine, and an acid, frequently aspartic acid. Together these three residues compose the catalytic triad which is a signature of the family. Serine proteases are divided into two major evolutionary families. One family is represented by the bacterial protease subtilisin. The other family is the trypsin-chymotrypsin family and includes chymotrypsin, trypsin, and elastase. Other members of the trypsin-chymotrypsin family include thrombin, plasmin, kallikrein, and acrosin. Members of the trypsin-chymotrypsin serine protease family are involved in a range of diverse cellular functions including, cell motility, cell growth and differentiation, hormone production, organogenesis, extracellular matrix regulation, blood clotting, and complementation activation.

These proteases catalyze the hydrolysis of peptide bonds in proteins and peptides. While the various serine proteases catalyze this reaction in very similar ways, they differ in their preference for the amino acid side chains immediately C-terminal to the cleave site. Trypsin cleaves bonds only after lysine and arginine residues, whereas chymotrypsin cleaves bonds after large hydrophobic residues. Other proteases of this family have less distinct preferences for this position, but also depend to varying extents on the residues at neighboring positions.

Some members of the trypsin serine protease family play critical roles in a variety of important biological events including regulating cell proliferation, tumor growth, tumor invasion, metastasis, development, and tissue remodeling. Accordingly, there is a need for identifying and characterizing novel trypsin serine proteases.

SUMMARY OF THE INVENTION

The present invention is based, in part, on the discovery of a novel trypsin family member, referred to herein as "14094". The nucleotide sequence of a cDNA encoding 14094 is shown in SEQ ID NO:1 and SEQ ID NO:11, and the amino acid sequence of a 14094 polypeptide is shown in SEQ ID NO:2 and SEQ ID NO:12. In addition, the nucleotide sequences of the coding region are depicted in SEQ ID NO:3 and SEQ ID NO:13.

Accordingly, in one aspect, the invention features a nucleic acid molecule that encodes a 14094 protein or polypeptide, e.g., a biologically active portion of the 14094 protein. In a preferred embodiment the isolated nucleic acid molecule encodes a polypeptide having the amino acid sequence of SEQ ID NO:2 or SEQ ID NO:12. In other embodiments, the invention provides isolated 14094 nucleic acid molecules having the nucleotide sequence shown in SEQ ID NO:1, SEQ ID NO:11, SEQ ID NO:3, or SEQ ID NO:13. In still other embodiments, the invention provides nucleic acid molecules that are substantially identical (e.g., naturally occurring allelic variants) to the nucleotide sequence shown in SEQ ID NO:1, SEQ ID NO:3, SEQ ID NO:1, or SEQ ID NO:13. In other embodiments, the invention provides a nucleic acid molecule which hybridizes under a stringency condition described herein to a nucleic acid molecule comprising the nucleotide sequence of SEQ ID NO:1, SEQ ID NO:3, SEQ ID NO:11, or SEQ ID NO:13, wherein the nucleic acid encodes a full length 14094 protein or an active fragment thereof.

In a related aspect, the invention further provides nucleic acid constructs that include a 14094 nucleic acid molecule described herein. In certain embodiments, the nucleic acid molecules of the invention are operatively linked to native or heterologous regulatory sequences. Also included, are vectors and host cells containing the 14094 nucleic acid molecules of the invention e.g., vectors and host cells suitable for producing 14094 nucleic acid molecules and polypeptides.

In another related aspect, the invention provides nucleic acid fragments suitable as primers or hybridization probes for the detection of 14094-encoding nucleic acids.

In still another related aspect, isolated nucleic acid molecules that are antisense to a 14094 encoding nucleic acid molecule are provided.

In another aspect, the invention features, 14094 polypeptides, and biologically active or antigenic fragments thereof that are useful, e.g., as reagents or targets in assays applicable to treatment and diagnosis of 14094-mediated or -related disorders. In another embodiment, the invention provides 14094 polypeptides having a 14094 activity. Preferred polypeptides are 14094 proteins including at least one trypsin domain, and, preferably, having a 14094 activity, e.g., a 14094 activity as described herein.

In other embodiments, the invention provides 14094 polypeptides, e.g., a 14094 polypeptide having the amino acid sequence shown in SEQ ID NO:2, or SEQ ID NO:12; an amino acid sequence that is substantially identical to the amino acid sequence shown in SEQ ID NO:2, or SEQ ID NO:12; or an amino acid sequence encoded by a nucleic acid molecule having a nucleotide sequence which hybridizes under a stringency condition described herein to a nucleic acid molecule comprising the nucleotide sequence of SEQ ID NO:1, SEQ ID NO:3, SEQ ID NO:11, or SEQ ID NO:13 or an active fragment thereof.

In a related aspect, the invention further provides nucleic acid constructs which include a 14094 nucleic acid molecule described herein.

In a related aspect, the invention provides 14094 polypeptides or fragments operatively linked to non-14094 polypeptides to form fusion proteins.

In another aspect, the invention features antibodies and antigen-binding fragments thereof, that react with, or more preferably specifically bind 14094 polypeptides.

In another aspect, the invention provides methods of screening for compounds that modulate the expression or activity of the 14094 polypeptides or nucleic acids.

In still another aspect, the invention provides a process for modulating 14094 polypeptide or nucleic acid expression or activity, e.g. using the screened compounds. In certain embodiments, the methods involve treatment of conditions related to aberrant activity or expression of the 14094 polypeptides or nucleic acids, such as conditions involving aberrant or deficient cellular proliferation or differentiation.

The invention also provides assays for determining the activity of or the presence or absence of 14094 polypeptides or nucleic acid molecules in a biological sample, including for disease diagnosis.

In still another aspect, the invention provides a process for modulating 14094 polypeptide or nucleic acid expression or activity, e.g. using the screened compounds. In certain embodiments, the methods involve treatment of conditions related to aberrant activity or expression of the 14094 polypeptides or nucleic acids, such as conditions involving aberrant or deficient cellular proliferation or differentiation, or tumor invasion or metastasis.

In yet another aspect, the invention provides methods for inhibiting the proliferation or inducing the killing or differentiation, of a 14094-expressing cell (e.g., a 14094-expressing hyperproliferative cell), comprising contacting the cell with a an agentm e.g., a compound identified using the methods described herein) that modulates the activity, or expression, of the 14094 polypeptide or nucleic acid, thereby inhibiting the proliferation or inducing the killing or differentiation of the 14094-expressing cell.

In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol.

In a preferred embodiment, the hyperproliferative cell is found in a solid tumor, a soft tissue tumor, or a metastatic lesion. Preferably, the tumor is a sarcoma, a carcinoma, or an adenocarcinoma. Preferably, the hyperproliferative cell is found in a cancerous or pre-cancerous tissue, e.g., a cancerous or pre-cancerous tissue where a 14094 polypeptide or nucleic acid is expressed, e.g., breast, ovarian, colon, liver, lung, kidney, or brain cancer. Most preferably, the hyperproliferative cell is found in a tumor from the breast, ovary, colon, liver or lung.

In a preferred embodiment, the compound is an inhibitor of a 14094 polypeptide. Preferably, the inhibitor is chosen from a peptide, a phosphopeptide, a small organic molecule, a small inorganic molecule and an antibody (e.g., an antibody conjugated to a therapeutic moiety selected from a cytotoxin, a cytotoxic agent and a radioactive metal ion). The inhibitor can also be a trypsin inhibitor or a derivative thereof, or a peptidomimetic, e.g., a phosphonate analog of a peptide substrate.

In a preferred embodiment, the compound is an inhibitor of a 14094 nucleic acid, e.g., an antisense, a ribozyme, or a triple helix molecule.

In a preferred embodiment, the compound is administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

In another aspect, the invention features methods for treating or preventing a disorder characterized by aberrant cellular proliferation or differentiation of a 14094-expressing cell, in a subject. Preferably, the method includes comprising administering to the subject (e.g., a mammal, e.g., a human) an effective amount of a compound (e.g., a compound identified using the methods described herein) that modulates the activity, or expression, of the 14094 polypeptide or nucleic acid.

In a preferred embodiment, the disorder is a cancerous or pre-cancerous condition. Most preferably, the disorder is a cancer, e.g., a solid tumor, a soft tissue tumor, or a metastatic lesion. Preferably, the cancer is a sarcoma, a carcinoma, or an adenocarcinoma. Preferably, the cancer is found in a tissue where a 14094 polypeptide or nucleic acid is expressed, e.g., breast, ovarian, colon, liver, lung, kidney, or brain cancer. Most preferably, the cancer is found in the breast, ovary, colon, liver and lung.

In a preferred embodiment, the compound is an inhibitor of a 14094 polypeptide. Preferably, the inhibitor is chosen from a peptide, a phosphopeptide, a small organic molecule, a small inorganic molecule and an antibody (e.g., an antibody conjugated to a therapeutic moiety selected from a cytotoxin, a cytotoxic agent and a radioactive metal ion). The inhibitor can also be a trypsin inhibitor or a derivative thereof, or a peptidomimetic, e.g., a phosphonate analog of a peptide substrate.

In a preferred embodiment, the compound is an inhibitor of a 14094 nucleic acid, e.g., an antisense, a ribozyme, or a triple helix molecule.

In a preferred embodiment, the compound is administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

The invention also provides assays for determining the activity of or the presence or absence of 14094 polypeptides or nucleic acid molecules in a biological sample, including for disease diagnosis. Preferably, the biological sample includes a cancerous or pre-cancerous cell or tissue. For example, the cancerous tissue can be a solid tumor, a soft tissue tumor, or a metastatic lesion. Preferably, the cancerous tissue is a sarcoma, a carcinoma, or an adenocarcinoma. Preferably, the cancerous tissue is from the breast, ovarian, colon, lung, liver, kidney, or brain.

In a further aspect the invention provides assays for determining the presence or absence of a genetic alteration in a 14094 polypeptide or nucleic acid molecule in a sample, for, e.g., disease diagnosis. Preferably, the sample includes a cancer cell or tissue. For example, the cancer can be a solid tumor, a soft tissue tumor, or a metastatic lesion. Preferably, the cancer is a sarcoma, a carcinoma, or an adenocarcinoma. Preferably, the cancer is a breast, ovarian, colon, lung, liver, kidney, or brain cancer.

In a still further aspect, the invention provides methods for staging a disorder, or evaluating the efficacy of a treatment of a disorder, e.g., proliferative disorder, e.g., cancer (e.g., breast, ovarian, colon, liver or lung cancer). The method includes: treating a subject, e.g., a patient or an animal, with a protocol under evaluation (e.g., treating a subject with one or more of: chemotherapy, radiation, and/or a compound identified using the methods described herein); and evaluating the expression of a 14094 nucleic acid or polypeptide before and after treatment. A change, e.g., a decrease or increase, in the level of a 14094 nucleic acid (e.g., mRNA) or polypeptide after treatment, relative to the level of expression before treatment, is indicative of the efficacy of the treatment of the disorder.

In a preferred embodiment, the disorder is a cancer of the breast, ovary, colon, lung, or liver. The level of 14094 nucleic acid or polypeptide expression can be detected by any method described herein.

In a preferred embodiment, the evaluating step includes obtaining a sample (e.g., a tissue sample, e.g., a biopsy, or a fluid sample) from the subject, before and after treatment and comparing the level of expressing of a 14094 nucleic acid (e.g., mRNA) or polypeptide before and after treatment.

In another aspect, the invention provides methods for evaluating the efficacy of a therapeutic or prophylactic agent (e.g., an anti-neoplastic agent). The method includes: contacting a sample with an agent (e.g., a compound identified using the methods described herein, a cytotoxic agent) and, evaluating the expression of 14094 nucleic acid or polypeptide in the sample before and after the contacting step. A change, e.g., a decrease or increase, in the level of 14094 nucleic acid (e.g., mRNA) or polypeptide in the sample obtained after the contacting step, relative to the level of expression in the sample before the contacting step, is indicative of the efficacy of the agent. The level of 14094 nucleic acid or polypeptide expression can be detected by any method described herein.

In a preferred embodiment, the sample includes cells obtained from a cancerous tissue where a 14094 polypeptide or nucleic acid is obtained, e.g., a cancer of the breast, ovary, colon, lung, or liver.

In a preferred embodiment, the sample is a tissue sample (e.g., a biopsy), a bodily fluid, cultured cells (e.g., a tumor cell line).

In further aspect, the invention provides assays for determining the presence or absence of a genetic alteration in a 14094 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 14094 molecule. In one embodiment, the capture probe is a nucleic acid, e.g., a probe complementary to a 14094 nucleic acid sequence. In another embodiment, the capture probe is a polypeptide, e.g., an antibody specific for 14094 polypeptides. Also featured is a method of analyzing a sample by contacting the sample to the aforementioned array and detecting binding of the sample to the array.

Other features and advantages of the invention will be apparent from the following detailed description, and from the claims.

BRIEF DESCRIPTION OF THE DRAWINGS

FIGS. 2A and 2B depict alignments of the trypsin domain of human 14094 with consensus amino acid sequences derived from a hidden Markov model (HMM). In FIG. 3A, the upper sequence is the consensus amino acid sequence for a model trypsin domain from PFAM (SEQ ID NO:4), while the lower amino acid sequence corresponds to amino acids 217 to 443 of SEQ ID NO:2. In FIG. 3B, the upper sequence is the consensus amino acid sequence for a model trypsin domain from SMART (SEQ ID NO:5), while the lower amino acid sequence corresponds to amino acids 216 to 443 of SEQ ID NO:2.

FIGS. 3A and 3B depict alignments of human 14094 with consensus amino acid sequences derived from a hidden Markov model (HMM). In FIG. 4A, the upper sequence is the consensus amino acid sequence for a model low-density lipoprotein (LDL) receptor domain class A from PFAM (SEQ ID NO:6), while the lower amino acid sequence corresponds to amino acids 71 to 109 of SEQ ID NO:2. In FIG. 4B, the upper sequence is the consensus amino acid sequence for a model scavenger receptor cysteine-rich domain from PFAM (SEQ ID NO:7), while the lower amino acid sequence corresponds to amino acids 110 to 205 of SEQ ID NO:2.

DETAILED DESCRIPTION

Figure 1:
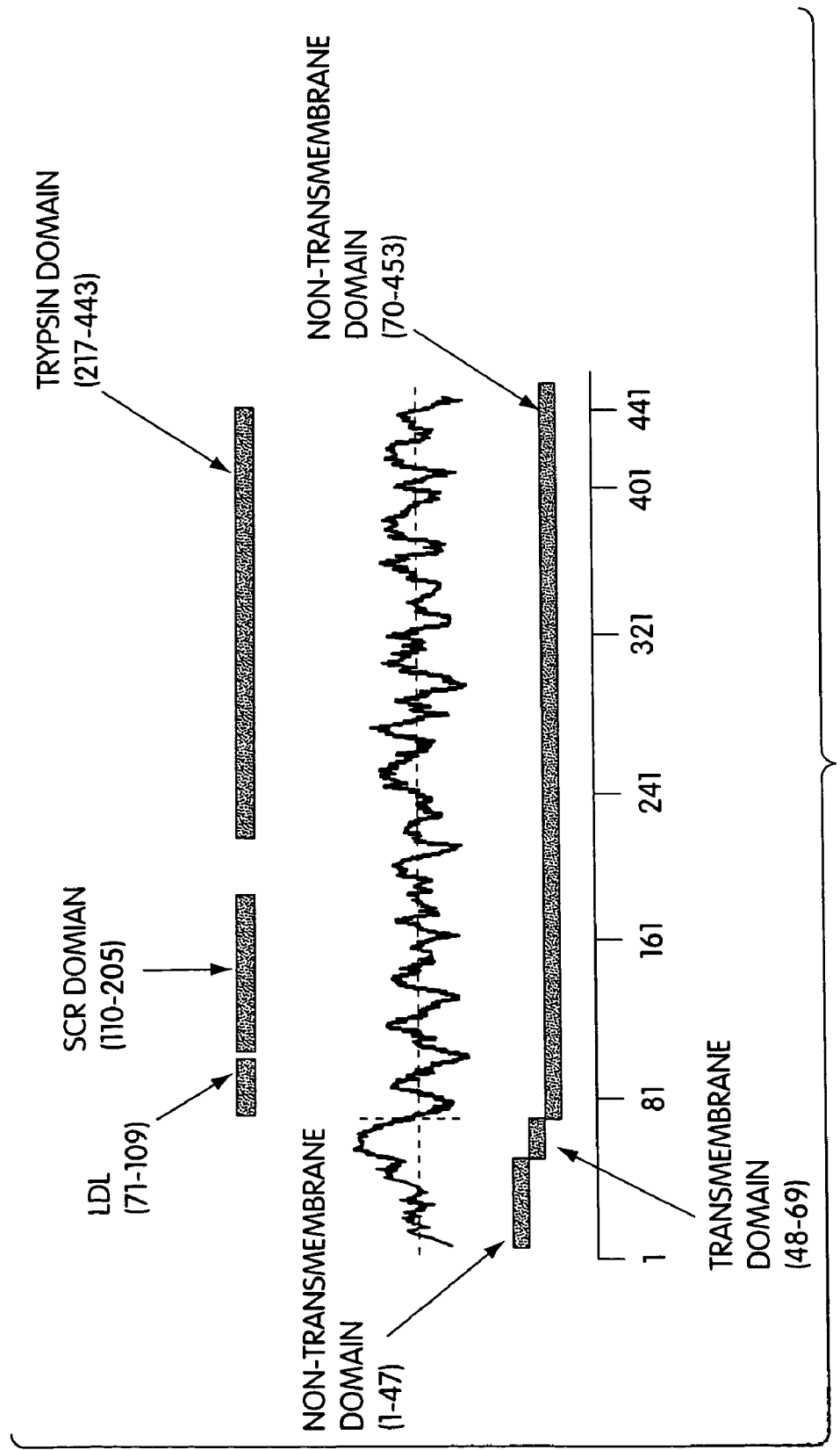
FIG. 1 depicts a hydropathy plot of human 14094. Domains including the low density lipoprotein receptor domain (LDL), scavenger receptor cysteine-rich domain (SCR), and the trypsin domain are indicated as are transmembrane and non-transmembrane domains. The numbers corresponding to the amino acid sequence of human 14094 (SEQ ID NO:2) are indicated. Polypeptides of the invention include fragments which include: all or part of a hydrophobic sequence, i.e., a sequence above the dashed line, e.g., the sequence of from about amino acid residue 30–65, about amino acids 135–155; all or part of a hydrophilic sequence, i.e., a sequence below the dashed line, e.g., the sequence of from about amino acid residue 90 to about amino acid residue 110 of SEQ ID NO:2.

Human 14094 nucleic acids include nucleic acids having the sequences recited in SEQ ID NO:1 and SEQ ID NO:11 (as recited, e.g., in Example 1).

The 14094 sequence SEQ ID NO:1, which is approximately 2948 nucleotides long, including untranslated regions, contains a predicted methionine-initiated coding sequence of about 1365 nucleotides, including the termination codon (SEQ ID NO:3). The coding sequence encodes a 453 amino acid protein (SEQ ID NO:2), not including the termination codon (SEQ ID NO:2, as recited in Example 1).

The 14094 sequence SEQ ID NO:11, which is approximately 2951 nucleotides long, including untranslated regions, contains a predicted methionine-initiated coding sequence of about 1368 nucleotides, including the termination codon (SEQ ID NO:13). The coding sequence encodes a 454 amino acid protein (SEQ ID NO:12), not including the termination codon (SEQ ID NO:13, as recited in Example 1). Whereas features of human 14094 molecules are described below with reference to SEQ ID NO:1, 2, and 3, one skilled in art can readily identify the corresponding features in the 14094 molecules with respect to SEQ ID NO:11, 12, and 13.

Human 14094 contains the following regions or other structural features:

a predicted trypsin domain (PFAM Accession PF00089) located at about amino acid 217 to 443 of SEQ ID NO:2, which includes a histidine active site located at about amino acid 257 and a serine active site located at about amino acid 400 of SEQ ID NO:2;

an Arg-Ile-Val-Gly-Gly (or "RIVGG") sequence (SEQ ID NO:8), which is a typical proteolytic activator site of many serine protease zymogens, located at about amino acids 216–220 of SEQ ID NO:2;

a predicted low-density lipoprotein (LDL) receptor domain class A domain (PFAM Accession PF00057) located at about amino acids 71–109 of SEQ ID NO:2, which includes six conserved cysteines, located at about amino acid residues, 73, 79, 85, 92, 98, and 107 of SEQ ID NO:2;

a predicted scavenger receptor cysteine-rich domain (PFAM Accession PF00530) located at about amino acids 110 to 205 of SEQ ID NO:2;

one predicted transmembrane regions located at about amino acids 48 to 69 of SEQ ID NO:2;

two predicted non-transmembrane regions located at about amino acids 1 to about 47 (N-terminal non-transmembrane region), and from about amino acids 70 to about 453;

a predicted N-glycosylation site (PS00001) located from about amino acids 221 to about 224 of SEQ ID NO:2;

a predicted glycosaminoglycan attachment site (PS00002) located from about amino acids 341 to 344 of SEQ ID NO:2;

six predicted protein kinase C phosphorylation sites (PS00005) located at about amino acids 14 to about 16, from about amino acids 74 to about 76, from about amino acids 82 to about 84, from about amino acids 124 to about 126, from about amino acids 214 to about 216, and from about amino acids 365 to about 367 of SEQ ID NO:2;

four predicted casein kinase II phosphorylation sites (PS00006) located at about amino acids 159 to about 162, from about amino acids 276 to 279, from about amino acids 315 to about 318, and from about amino acids 438 to about 441 of SEQ ID NO:2;

a predicted tyrosine kinase phosphorylation site (PS00007) located at about amino acids 99 to about 105 of SEQ ID NO:2; and seven predicted N-myristylation sites (PS00008) located at about amino acids 94 to about 99, from about amino acids 111 to about 116, from about amino acids 193 to about 198, from about amino acids 219 to about 224, from about amino acids 302 to about 307, from about amino acids 391 to about 396, and from about amino acids 421 to about 426 of SEQ ID NO:2.

TABLE 1

Summary of Sequence Information for 14094

| Gene | cDNA | ORF | Polypeptide |
|---|---|---|---|
| 14094 | SEQ NO: 1, | SEQ ID NO: 3 | SEQ ID NO: 2 |
| 14094 | SEQ ID NO: 11 | SEQ ID NO: 13 | SEQ ID NO: 12 |

TABLE 2

Summary of Domains of 14094

| Domain | Location in SEQ ID NO:2 |
|---|---|
| Transmembrane domain | about 48–69 |
| Low-density lipoprotein receptor domain class A | about 71–109 |

TABLE 2-continued

Summary of Domains of 14094

| Domain | Location in SEQ ID NO:2 |
|---|---|
| scavenger receptor cysteine-rich domain | about 110–205 |
| Trypsin domain | about 216–443 |

The 14094 polypeptide contains a significant number of structural characteristics in common with members of the trypsin serine protease family (Rawlings and Barret (1993) *Biochem J.* 290: 205–218, and *Meth. Enzymol.* (1994) 244: 19–61, the contents of which are hereby incorporated by reference in their entirety). Based on the presence of the histidine-aspartate-serine catalytic triad, the 14094 polypeptide appears to be a member of the serine protease clan SA (Rawlings and Barret, supra). The clan SA includes the trypsin-chymotrypsin family (S1), the α-lytic endopeptidase family (S2), and the Togavirus endopeptidase family (S3).

The 14094 polypeptide belongs to the trypsin-chymotrypsin family (S1). The prototype of this family is chymotrypsin and the 3D structure of some of its members has been resolved. The trypsin-chymotrypsin family (S1) includes such members as: trypsin (forms I, II, III, IV, Va and Vb); trypsin-like enzyme; hepsin; TMPRSS2; venombin; cercarial elastase; brachyurin; Factor C; Proclotting enzyme; easter gene product; snake gene product; stubble gene product; Vitellin-degrading endopeptidase; hypodermin C; Serine proteases 1 and 2; achelase; chymotrypsin (forms A, B, II, and 2); Proteinase RVV-V (forms α and γ); flavoboxin; venombin A; Crotalase; enteropeptidase; acrosin; ancrod; seminin; semenogelase; tissue kallikrein; renal kallikrein; submandibular kallikrein; 7S nerve growth factor (chains α and γ); epidermal growth factor-binding protein (forms 1, 2, and 3); tonin; arginine esterase; pancreatic elastase I; pancreatic elastase II (forms A and B); pancreatic endopeptidase E (forms A and B); leukocyte elastase; medullasin; azurocidin; cathepsin G; proteinase 3 (myeloblastin); chymase (forms I and II); γ-renin; tryptase (forms 1, 2, and 3); granzyme A; natural killer cell protease 1; gilatoxin; granzymes B, C, D, E, F, G and Y; carboxypeptidase A complex component III; complement factors D, B, I; complement components C1r, C1s, and C2; calcium-dependent serine protease; hypodermin A, B, and C; haptoglobin (forms 1 and 2); haptoglobin-related protein; plasmin; apolipoprotein (a); hepatocyte growth factor; medullasin; thrombin; t-plasminogen activator; u-plasminogen activator; salivary plasminogen activator; plasma kallikrein; coagulation factors VII, IX, X, XI, and XII; and proteins C and Z, as well as as-yet unidentified members.

The 14094 polypeptides are homologous to the S1 family members, TMPRSS2 and hepsin. These three proteins are predicted type II integral membrane proteins with extracellular protease domains. For example, TMPRSS2 possesses an extracellular protease domain, an extracellular low density lipoprotein receptor A (LDLRA), scavenger receptor cysteine rich (SRCR) domains, a transmembrane domain and a cytoplasmic domain (Paoloni-Giacobino, A. et al. (1997) *Genomics* 44: 309–320). TMPRSS2 proteins have been implicated in regulating cell proliferation and motility. Hepsin proteases are also transmembrane proteins that include a trypsin protease domain located on its extracellular side. Hepsin proteases are overexpressed in ovarian tumors and hepatoma cells (Tanimoto, H. et al. (1997) *Cancer Res.* 57:2884–2887). Further in vitro studies have shown inhibition of hepatoma cell proliferation using hepsin inhibitors (Torres-Rosado, A. et al. (1993) *Proc. Natl. Acad. Sci.* USA 90: 7181–7185).

Accordingly, the 14094 polypeptide contains a significant number of structural characteristics in common with members of the S1 family of the SA clan of serine-type proteases (also referred to herein as "trypsin-chymotrypsin" or "trypsin" family members). The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, a "trypsin-chymotrypsin family member" typically contains a catalytic unit which is generally a polypeptide sequence of about 100 to about 300 amino acids, more preferably about 150 to about 250 amino acid residues, about 200 to about 230, or about 220, although some members have N-terminal extensions of unrelated peptide segments. The catalytic unit almost always forms the C-terminal portion of the enzyme. These proteases typically cleave arginine or lysine residues in a target protein.

Trypsin-chymotrypsin family members preferably have at least one trypsin domain, comprising at least one histidine active site residue, and at least one serine active site residue. Trypsin-chymotrypsin family members can also include an aspartate residue within the trypsin domain. These three residues act as a "catalytic triad", with serine as nucleophile, aspartate as electrophile, and histidine as base. The serine nucleophile typically occurs in a signature motif characterized by Prosite Motif PS00135 (also PDOC00124): G-[DE]-S-G-[GS] (SEQ ID NO:9). Typically, a trypsin domain additionally includes an activation and cleavage site, Arg-Ile-Val-Gly-Gly (or "RIVGG"; SEQ ID NO:8), which is present just N-terminal to the serine protease domain.

14094 polypeptides contain structural features similar to trypsin-chymotrypsin family members. For example, the trypsin domain of the 14094 polypeptide has a conserved histidine residue present at about amino acid 257 of SEQ ID NO:2, and a serine active site located at amino acid 400 of SEQ ID NO:2. The trypsin domain of the 14094 polypeptide additionally includes nine conserved cysteines, which are present at about amino acids 242, 258, 324, 338, 369, 385, 396, 406, and 424 of SEQ ID NO:2. Eight of these cysteines can form disulfide bonds together in an intramolecular context. Preferably, the disulfide bonds are formed between residues about 242 and 258, 338 and 406, 369 and 385, 396 and 424 of SEQ ID NO:2. Cysteine 324 can form an intermolecular disulfide with a cysteine N-terminal to the trypsin domain. The trypsin domain of 14094 polypeptide also begins with the motif Arg-Ile-Val-Gly-Gly (SEQ ID NO:8), which is a signature for the proteolytic activation site of many zymogens of serine proteases. This motif can be found at about amino acids 216 to 220 of SEQ ID NO:2. The invention also features 14094 polypeptides which are in mature and processed form, e.g., a polypeptide which is cleaved between Arg 216 of SEQ ID NO:2 and Ile 217 of SEQ ID NO:2 or a polypeptide that includes about amino acids 217 to 453 of SEQ ID NO:2. The mature and processed polypeptides may be proteolytically active.

In addition, the 14094 polypeptide includes the sequence GDSGG, which matches PS00135, at about amino acids 398 to 402 of SEQ ID NO:2. The histidine base typically occurs in a signature motif characterized by Prosite Motif PS00134 (also PDOC00124): [LIVM]-[ST]-A-[STAG]-H—C (SEQ ID NO:10). A 14094 polypeptide also contains the sequence ITAAHC, which matches PS00134, at about amino acids 253 to 258 of SEQ ID NO:2.

Trypsin-chymotrypsin family members occasionally function intracellularly, but more generally, they act extracellularly. Examples of such extracellular activity include release or activation of growth factors, degradation of extracellular matrix, coagulation, fibrinolysis, zymogen and growth hormone activation, and complement activation. Trypsin-chymotrypsin family members have been implicated in modulating tumor invasion and growth by, for example, releasing or activating growth factors and/or digesting extracellular matrix components.

A 14094 polypeptide includes at least one "trypsin domain" or at least one region homologous with a "trypsin domain".

As used herein, the term "trypsin domain" (or a "trypsin-chymotrypsin" domain) refers to a protein domain having an amino acid sequence of from about 50 to about 350 amino acid residues and having a bit score for the alignment of the sequence to the trypsin domain (HMM) of at least 80. Preferably, a trypsin domain includes at least about 100 to about 300 amino acids, more preferably about 150 to about 250 amino acid residues, about 200 to about 230, or about 226 amino acids and has a bit score for the alignment of the sequence to the trypsin domain (HMM) of at least 100, preferably at least 200, more preferably at least 220, and most preferably 250 or greater. The trypsin domain (HMM) has been assigned the PFAM Accession (PF00089). An alignment of the trypsin domain (from about amino acids 217 to about 443 of SEQ ID NO:2) of human 14094 with a consensus amino acid sequence derived from a hidden Markov model (PFAM) is depicted in FIG. 3A. An alignment of the trypsin domain (from about amino acids 217 to about 443 of SEQ ID NO:2) of human 14094 with a consensus amino acid sequence derived from another hidden Markov model (SMART) is depicted in FIG. 3B.

In a preferred embodiment, a 14094 polypeptide or protein has a "trypsin" domain or a region which includes at least about 100 to about 300 amino acids, more preferably about 150 to about 250 amino acid residues, about 210 to about 235, or about 226 amino acids amino acid residues and has at least about 70%, 80%, 90%, 95%, 99%, or 100% homology with a "trypsin domain," e.g., the trypsin domain of human 14094 (e.g., residues about 217 to 443 of SEQ ID NO:2). Preferably, the trypsin domain includes at least one histidine active site residue, and at least one serine active site residue. The trypsin domain can also include an aspartate residue, thus forming a catalytic triad, with serine as nucleophile, aspartate as electrophile, and histidine as base. The trypsin domain can additionally include an activation and cleavage site, Arg-Ile-Val-Gly-Gly (or "RIVGG"; SEQ ID NO:9), which is present just N-terminal to the serine protease domain.

To identify the presence of a "trypsin" domain in a 14094 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al. (1990) *Meth. Enzymol.* 183:146–159; Gribskov et al.(1987) *Proc. Natl. Acad. Sci. USA* 84:4355–4358; Krogh et al.(1994) *J. Mol. Biol.* 235:1501–1531; and Stultz et al.(1993) *Protein Sci.* 2:305–314, the contents of which are incorporated herein by reference. A search was performed against the PFAM HMM database resulting in the identification of a "trypsin domain" in the amino acid sequence of human 14094 at about residues 217 to about 443 of SEQ ID NO:2 with a bit score of 293 (see FIGS. 1 and 3).

A 14094 molecule can additionally include an "LDL-receptor class A" domain, or regions homologous with a "LDL-receptor class A" domain.

A LDL-receptor class A domain is characterized by a common fold, of about 40 amino acids, characterized by six conserved cysteines which form three disulfide bonds to produce a stable folded structure (Daly et al. (1995) *Proc Natl Acad Sci USA* 92:63334–63338). In the LDL-receptor, seven of these domains are present as consecutive units (Sudhof et al. (1985) *Science* 228:815–822). The LDL-receptor class A domains bind to LDL and calcium, particularly, the acid residues located between the fourth and sixth cysteines of this domain mediate high-affinity binding to the positively charged LDL and calcium ligands. This domain is also present in a variety of extracellular polypeptides, for example in human enterokinase complement factor I, complement components C6, C7, C8, and C9, and perlecan.

Figure 4:
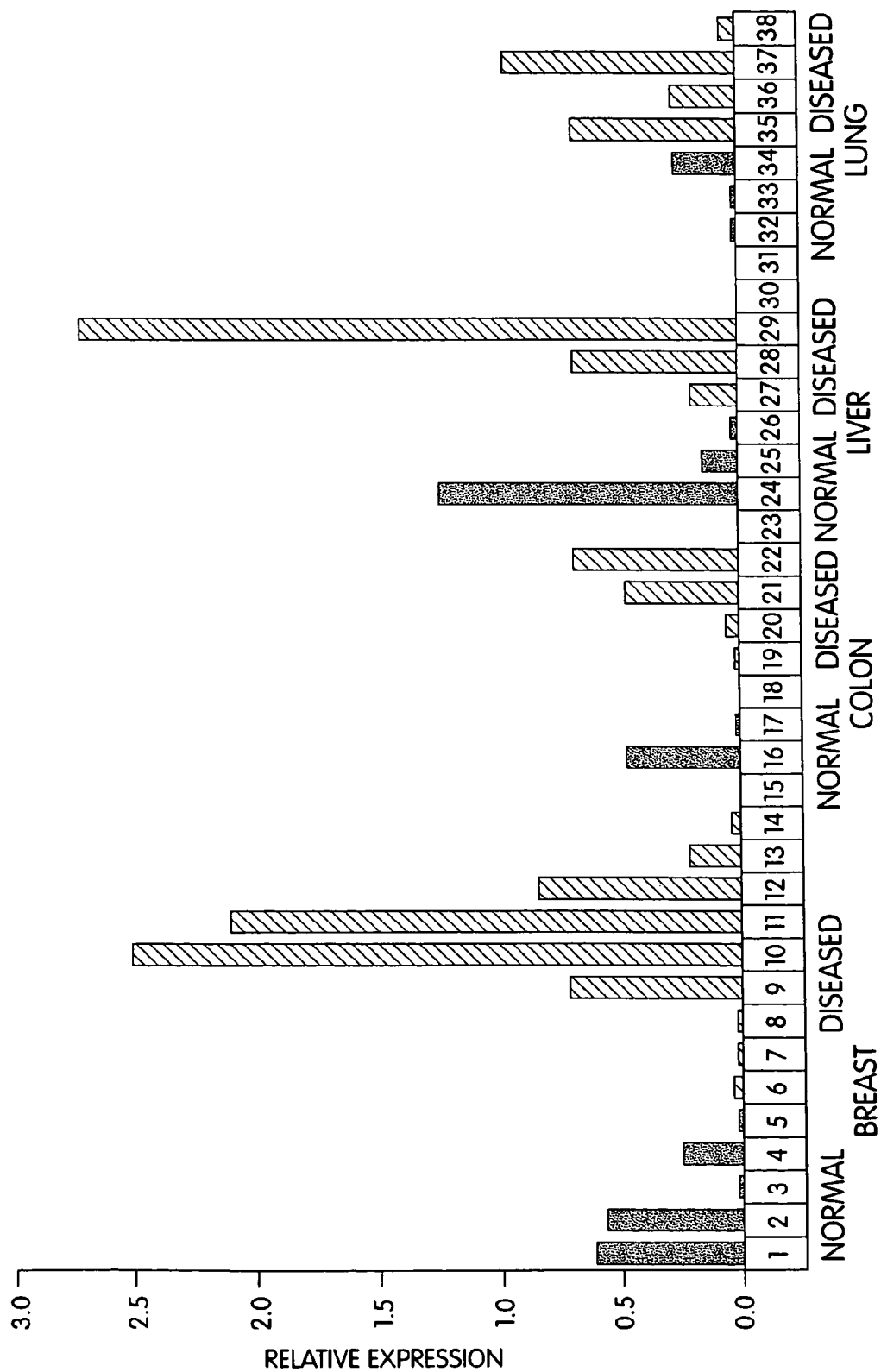
FIG. 4 is a bar graph depicting the expression of 14094 RNA in a panel of normal and tumor human tissues, including breast, colon, liver, and lung, detected using TAQ-MAN® analysis. 14094 RNA expression in normal (solid bars) and malignant ("diseased"; hatched bars) tissues from the breast, colon, liver and lung is shown. Elevated expression of 14094 RNA was detected in malignant tissues relative to normal tissues.

As used herein, the term "LDL-receptor class A domain" includes an amino acid sequence of about 30 to 50 amino acid residues in length, six conserved cysteine residues, an acidic patch located between the fourth and sixth cysteine, and having a bit score for the alignment of the sequence to the LDL-receptor class A domain (HMM) of at least 20. Preferably, a LDL-receptor class A domain includes at least about 20 to 70 amino acids, more preferably about 30 to 50 amino acid residues, or about 34 to 42 amino acids and has a bit score for the alignment of the sequence to the LDL-receptor class A domain (HMM) of at least 20 or greater. The LDL-receptor class A domain (HMM) has been assigned the PFAM Accession Number PF00057. An alignment of the LDL-receptor class A domain (amino acids 71 to 109 of SEQ ID NO:2) of human 14094 with a consensus amino acid sequence (SEQ ID NO:6) derived from a hidden Markov model is depicted in FIG. 4A.

In a preferred embodiment 14094 polypeptide or protein has a "LDL-receptor class A domain" or a region which includes at least about 20 to 70 more preferably about 30 to 50 or 34 to 42 amino acid residues and has at least about 70% 80% 90% 95%, 99%, or 100% homology with a "LDL-receptor class A domain," e.g., the LDL-receptor class A domain of human 14094 (e.g., residues 71 to 109 of SEQ ID NO:2). In a preferred embodiment, 14094 polypeptide has as part of its LDL-receptor class A domain six conserved cysteines, which can be present at about amino acids, 73, 79, 85, 92, 98, and 107 of SEQ ID NO:2. In another preferred embodiment, 14094 polypeptide has at least one, two, three, four, most preferably at least five acidic residues between about amino acids 92 and 107 of SEQ ID NO:2.

To identify the presence of a "LDL-receptor class A" domain in a 14094 protein sequence, and make the determination that a polypeptide or protein of interest has a particular profile, the amino acid sequence of the protein can be searched against a database of HMMs as described above. A search was performed against the HMM database resulting in the identification of a "LDL-receptor class A domain" domain in the amino acid sequence of human 14094 at about residues 71 to 109 of SEQ ID NO:2 (FIG. 1).

14094 molecule can further include a "scavenger receptor cysteine-rich" domain or regions homologous with a "scavenger receptor cysteine-rich" domain.

A scavenger receptor cysteine-rich domain is characterized by a common fold of approximately 100 amino acids, first identified in the type I macrophage scavenger receptor (Resnick et al. (1994) *Trends Biocehm Sci* 19:5–8; Freeman et al. (1990) *Proc Natl Acad Sci USA* 87:8810–8814). The domain is frequently found on the extracellular face of cell surface proteins or in plasma and other body fluids. Proteins, including CD5, CD6, macrophage scavenger receptor type I, the serine protease complement factor 1, cyclophilin C-binding protein, and Mac-2 binding protein contain this structural feature. The crystal structure of one such domain reveals a six-stranded β-sheet embracing an α-helix (Honenester et al. (1999) *Nat Str Biology* 6:228–232). In one case, the function of this domain has been elucidated. The most membrane-proximal scavenger receptor domain in CD6 is responsible for binding to the CD6-ligand, activated leukocyte cell adhesion molecule.

A 14094 polypeptide can include a "scavenger receptor cysteine-rich domain" or regions homologous with a "scavenger receptor cysteine-rich domain".

As used herein, the term "scavenger receptor cysteine-rich domain" includes an amino acid sequence of about 80 to 120 amino acid residues in length and having a bit score for the alignment of the sequence to the scavenger receptor cysteine-rich domain (HMM) of at least 3. Preferably, a scavenger receptor cysteine-rich domain includes at least about 80 to 120 amino acids, more preferably about 87 to 110 amino acid residues, or about 90 to 100 amino acids and has a bit score for the alignment of the sequence to the scavenger receptor cysteine-rich domain (HMM) of at least 3 or greater. The scavenger receptor cysteine-rich domain (HMM) has been assigned the PFAM Accession Number PF00530. An alignment of the scavenger receptor cysteine-rich domain (amino acids 110 to 205 of SEQ ID NO:2) of human 14094 with a consensus amino acid sequence (SEQ ID NO:7) derived from a hidden Markov model is depicted in FIG. 4B.

In a preferred embodiment 14094 polypeptide or protein has a "scavenger receptor cysteine-rich domain" or a region which includes at least about 80 to 120 more preferably about 87 to 110 or 90 to 100 amino acid residues and has at least about 70% 80% 90% 95%, 99%, or 100% homology with a "scavenger receptor cysteine-rich domain," e.g., the scavenger receptor cysteine-rich domain of human 14094 (e.g., residues 110 to 205 of SEQ ID NO:2).

To identify the presence of a "scavenger receptor cysteine-rich" domain in a 14094 protein sequence, and make the determination that a polypeptide or protein of interest has a particular profile, the amino acid sequence of the protein can be searched against a database of HMMs as described above. A search was performed against the HMM database resulting in the identification of a "scavenger receptor cysteine-rich domain" domain in the amino acid sequence of human 14094 at about residues 110 to 205 of SEQ ID NO:2 (see FIG. 1).

In one embodiment, a 14094 protein includes at least one transmembrane domain. As used herein, the term "transmembrane domain" includes an amino acid sequence of about 15 amino acid residues in length that spans a phospholipid membrane. More preferably, a transmembrane domain includes about at least 14, 16, 18, 20, 22, 24, 25, 30, 35 or 40 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al, (1996) *Annual Rev. Neurosci.* 19: 235–63, the contents of which are incorporated herein by reference.

In a preferred embodiment, a 14094 polypeptide or protein has at least one transmembrane domain or a region which includes at least 14, 16, 18, 20, 22, 24, 25, 30, 35 or 40 amino acid residues and has at least about 70%, 80%, 90%, 95%, 99%, or 100% homology with a "transmembrane domain," e.g., at least one transmembrane domain of human 14094 (e.g., from about amino acid residues 48 to about 69 of SEQ ID NO:2).

In another embodiment, a 14094 protein includes at least one "extracellular domain".

As defined herein, the term "extracellular domain" includes an amino acid sequence having a length of at least about 200, preferably about 250–500, more preferably about 300–450, more preferably about 350–400, and most preferably about 383 amino acid residues, and has an amino acid sequence that is outside of a cell, or extracellularly. The extracellular domain is the C-terminal amino acid of a loop is adjacent to an N-terminal amino acid of a transmembrane domain in a naturally-occurring 14094 or 14094-like molecule. For example, an extracellular domain can be found at about amino acids 70453 of SEQ ID NO:2.

In a preferred embodiment 14094 polypeptide or protein has at least one extracellular domain or a region which includes at least about 200, preferably about 250–500, more preferably about 300–450, more preferably about 350–400, and most preferably about 383 amino acid residues and has at least about 60%, 70%, 80%, 90%, 95%, 99%, or 100% homology with an "extracellular domain," e.g., at least one extracellular domain of human 14094 (e.g., residues 70–453 of SEQ ID NO:2).

In another embodiment, a 14094 protein includes a "cytoplasmic domain" in the sequence of the protein. As used herein, a "cytoplasmic domain" includes an amino acid sequence having a length of at least about 30, preferably about 30–60, more preferably about 40–50, even more preferably about 47 amino acid residues and is located within a cell or within the cytoplasm of a cell. The C-terminal amino acid residue of a "cytoplasmic domain" is adjacent to a N-terminal amino acid residue of a transmembrane domain in a naturally-occurring 14094 or 14094-like protein. For example, a cytoplasmic domain is found at about amino acid residues 1–47 of SEQ ID NO:2.

In a preferred embodiment, a 14094 polypeptide or protein has a cytoplasmic domain or a region which includes at least about 30, preferably about 30–60, more preferably about 40–50, even more preferably about 47 amino acid residues and has at least about 60%, 70%, 80%, 90% 95%, 99%, or 100% homology with an "cytoplasmic domain," e.g., the cytoplasmic domain of human 14094 (e.g., residues 1–47 of SEQ ID NO:2).

A 14094 family member can include one or more of: a trypsin domain, an extracellular domain, a transmembrane domain, a cytoplasmic domain, an LDL-receptor class A domain, and a scavenger receptor cysteine-rich domain.

As the 14094 polypeptides of the invention may modulate 14094-mediated activities, they may be useful as of for developing novel diagnostic and therapeutic agents for 14094-mediated or -related disorders, as described below.

As used herein, a "14094 activity", "biological activity of 14094" or "functional activity of 14094", refers to an activity exerted by a 14094 protein, polypeptide or nucleic acid molecule on e.g., a 14094-responsive cell or on a 14094 substrate, e.g., a protein substrate, as determined in vivo or in vitro, according to standard assay techniques. In one embodiment, a 14094 activity is a direct activity, such as an association with a 14094 target molecule, or an enzymatic activity on a second protein. A "target molecule" or "binding partner" is a molecule with which a 14094 protein binds or interacts in nature. In another embodiment, a 14094 activity is an indirect activity, such as a cellular signaling activity mediated by interaction of the 14094 protein with a second protein. For example, the 14094 proteins of the present invention can have one or more of the following activities: (1) modulate (stimulate or inhibit) cellular proliferation (2) modulate cell differentiation; (3) modulate tumorigenesis and tumor invasion; (4) alter extracellular matrix composition; (5) catalyze polypeptide growth factor activation and release; (6) regulate the blood clotting cascade; (7) catalyze proteolytic cleavage of a substrate, e.g., a protein substrate (e.g., cleavage at an arginine or lysine residue; (8) catalyze the proteolytic activation of signaling molecules, e.g., other proteases, growth factor activation or release; or (9) regulate of cell motility or attachment.

Figure 5:
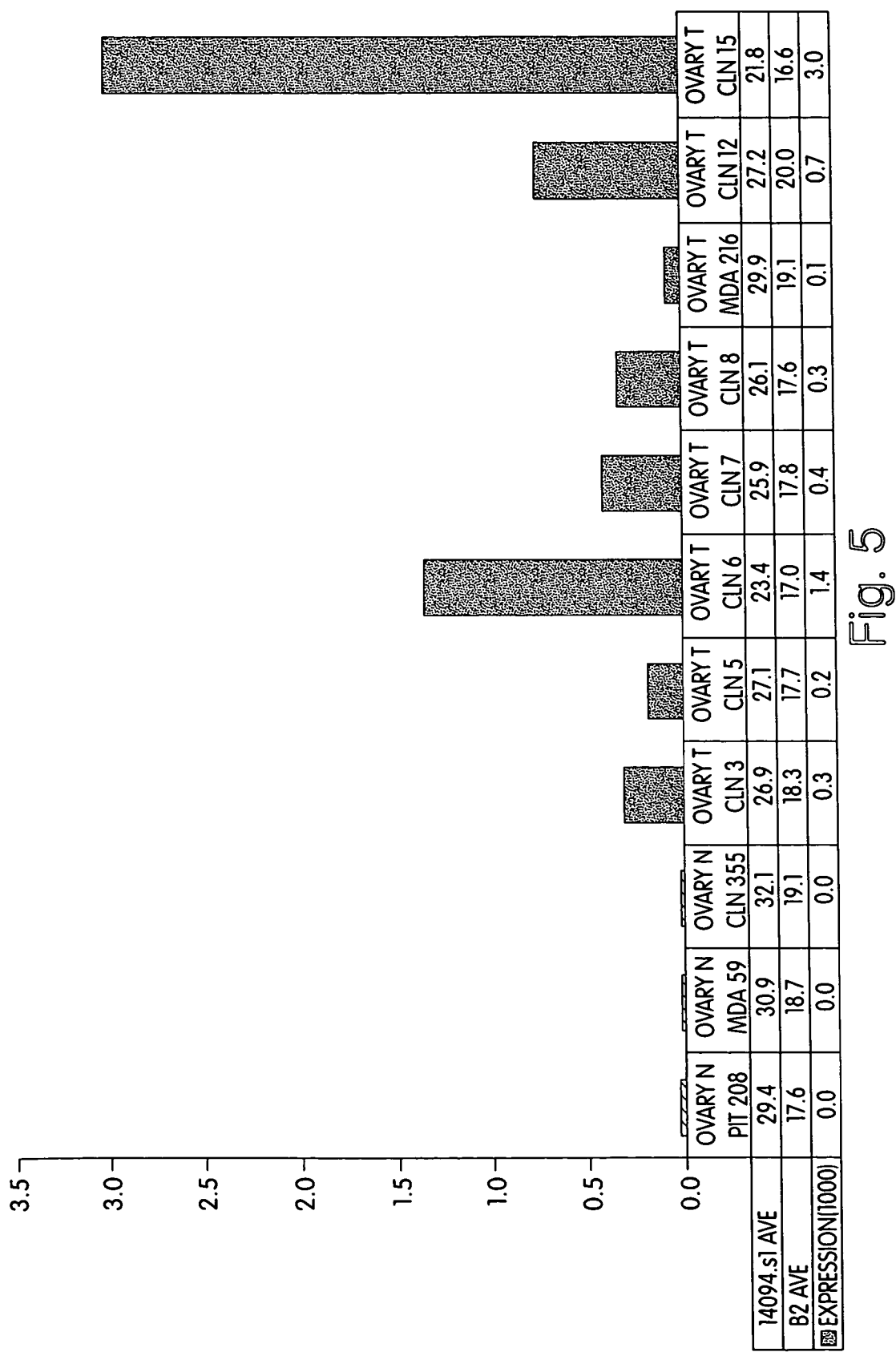
FIG. 5 is a bar graph depicting the expression of 14094 RNA in a panel of normal and tumor human ovarian samples, detected using TAQMAN® analysis. Elevated expression of 14094 RNA was detected in malignant ovarian tissues relative to normal tissues.
Figure 6:
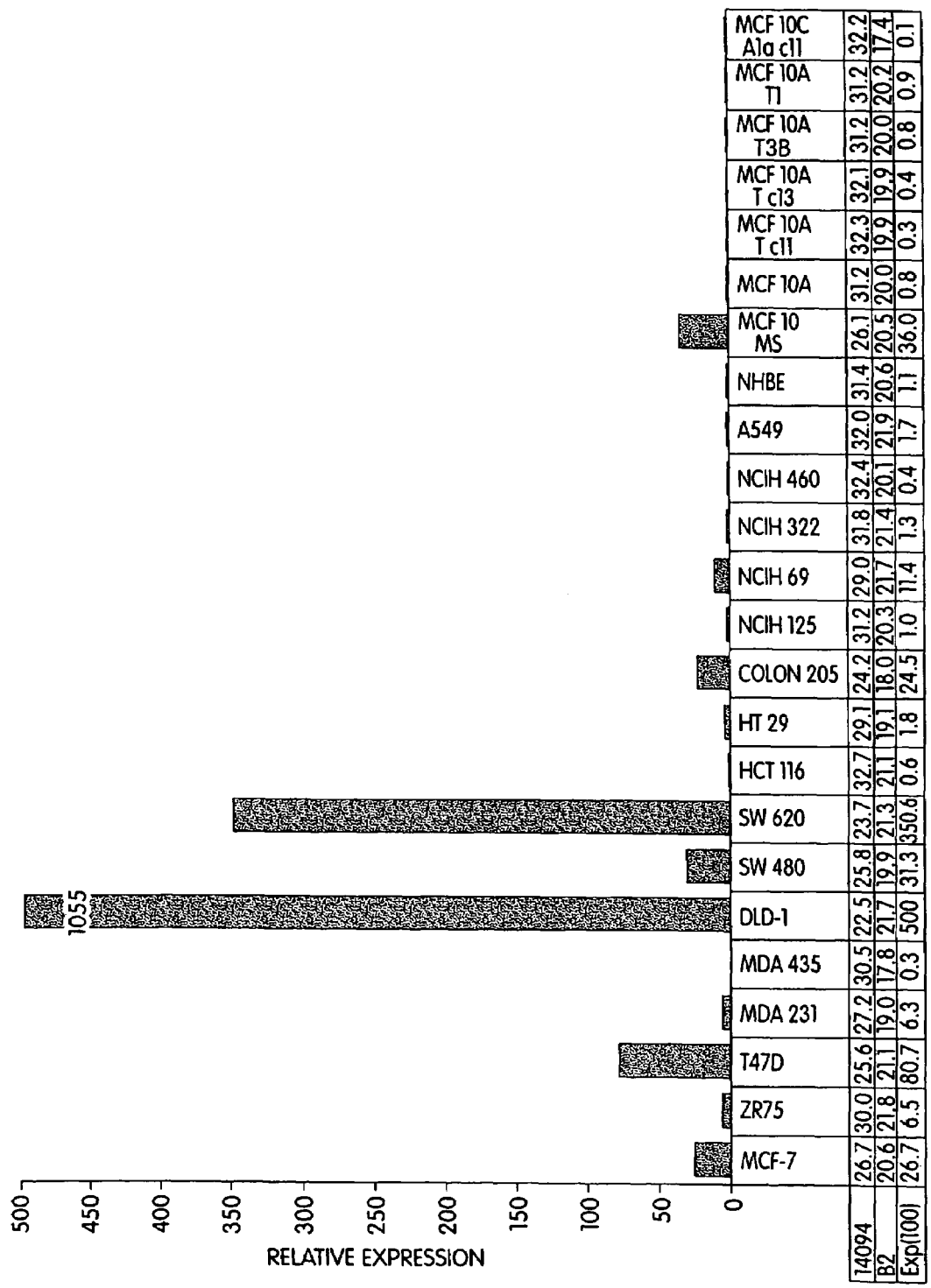
FIG. 6 is a bar graph depicting the expression of 14094 RNA in a panel of cell lines, detected using TAQMAN® analysis. Elevated expression of 14094 RNA was detected in DLD-1 and SW 620 cells lines. Both DLD-1 and SW620 are cell lines derived from colorectal carcinomas. SW620 is a lymph node metastasis of a colorectal carcinoma.

Based on the above-described sequence similarities, the 14094 molecules of the present invention are predicted to have similar biological activities as other trypsin family members, such as hepsin proteases. Hepsin proteases are overexpressed in ovarian tumors and hepatoma cells (Tanimoto, H. et al. (1997) *Cancer Res.* 57:2884–2887). Further in vitro studies have shown inhibition of hepatoma cell proliferation using hepsin inhibitors (Torres-Rosado, A. et al. (1993) *Proc. Natl. Acad. Sci. USA* 90: 7181–7185). 14094 is highly expressed in cells and tissues derived from tumors of the breast (e.g., IDC and DCIS), ovary (e.g., cystadenomas and mucinous tumors), lung (e.g., adenocarcinoma), liver, and colon (e.g., colonic adenocarcinomas) (see Tables 3–7 and FIGS. 4–6). Moreover, 14094 mRNA is expressed, although at lower levels compared to the expression in tumors, in cells derived from breast, ovary, kidney, liver, and aorta. Accordingly, the 14094 molecules can serve as novel diagnostic targets and therapeutic agents for controlling disorders involving the cells or tissues where they are expressed. For example, the 14094 molecules can serve as novel diagnostic targets and therapeutic agents for controlling disorders of cell proliferation, cell differentiation, organogenesis, coagulation, and cell signaling.

The polypeptides and nucleic acids of the invention can also be used to treat, prevent, and/or diagnose cancers and neoplastic conditions in addition to the ones described above. As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Examples of cellular proliferative and/or differentiative disorders include cancer, e.g., carcinoma, sarcoma, or metastatic disorders. The 14094 molecules can act as novel diagnostic targets and therapeutic agents for controlling breast cancer, ovarian cancer, colon cancer, lung cancer, metastasis of such cancers and the like. A metastatic tumor can arise from a multitude of primary tumor types, including but not limited to those of breast, lung, liver, colon and ovarian origin.

Examples of cancers or neoplastic conditions, in addition to the ones described above, include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

As the 14094 mRNA is expressed in the normal breast, kidney, liver, and aorta, it is likely that 14094 molecules of the present invention are involved in disorders characterized by aberrant activity of these cells. Thus, the 14094 molecules can act as novel diagnostic targets and therapeutic agents for controlling disorders involving aberrant activity of these cells.

The presence of 14094 RNA or protein can also be used to identify a cell or tissue, or other biological sample, as being derived from breast, kidney, liver, and aorta, or being of human origin. Expression can also be used to diagnose or stage a disorder, e.g., a cancer, a breast, ovarian, or liver disorder, especially a cancer of the breast. Expression can be determined by evaluating RNA, e.g., by hybridization of a 14094 specific probe, or with a 14094 specific antibody.

The 14094 protein, fragments thereof, and derivatives and other variants of the sequence in SEQ ID NO:2 thereof are collectively referred to as "polypeptides or proteins of the invention" or "14094 polypeptides or proteins". Nucleic acid molecules encoding such polypeptides or proteins are collectively referred to as "nucleic acids of the invention" or "14094 nucleic acids." 14094 molecules refer to 14094 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1–6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:1, 3, 11 or 13 corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a 14094 protein. The gene can optionally further include non-coding sequences, e.g., regulatory sequences and introns. Preferably, a gene encodes a mammalian 14094 protein or derivative thereof.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of 14094 protein is at least 10% pure. In a preferred embodiment, the preparation of 14094 protein has less than about 30%, 20%, 10% and more preferably 5% (by dry weight), of non-14094 protein (also referred to herein as a "contaminating protein"), or of chemical precursors or non-14094 chemicals. When the 14094 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 14094 without abolishing or substantially altering a 14094 activity. Preferably the alteration does not substantially alter the 14094 activity, e.g., the activity is at least 20%, 40%, 60%, 70% or 80% of wild-type. An "essential" amino acid residue is a residue that, when altered from the wild-type sequence of 14094, results in abolishing a 14094 activity such that less than 20% of the wild-type activity is present. For example, conserved amino acid residues in 14094 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 14094 protein is preferably replaced with another amino acid residue from the same side chain family. Alternatively, in another embodiment, mutations can be introduced randomly along all or part of a 14094 coding sequence, such as by saturation mutagenesis, and the resultant mutants can be screened for 14094 biological activity to identify mutants that retain activity. Following mutagenesis of SEQ ID NO:1, 11, 3 or 13, the encoded protein can be expressed recombinantly and the activity of the protein can be determined.

As used herein, a "biologically active portion" of a 14094 protein includes a fragment of a 14094 protein which participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a 14094 molecule and a non-14094 molecule or between a first 14094 molecule and a second 14094 molecule (e.g., a dimerization interaction). Biologically active portions of a 14094 protein include peptides comprising amino acid sequences sufficiently homologous to or derived from the amino acid sequence of the 14094 protein, e.g., the amino acid sequence shown in SEQ ID NO:2, which include less amino acids than the full length 14094 proteins, and exhibit at least one activity of a 14094 protein. Typically, biologically active portions comprise a domain or motif with at least one activity of the 14094 protein, e.g., a protease activity. A biologically active portion of a 14094 protein can be a polypeptide which is, for example, 10, 25, 50, 100, 200 or more amino acids in length. Biologically active portions of a 14094 protein can be used as targets for developing agents which modulate a 14094 mediated activity, e.g., a protease activity.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444–453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11–17) which has been incorporated into the ALIGN program (version 2.0), using a PAM 120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403–10. BLAST nucleotide searches can be performed with the NBLAST program, score=100, wordlength=12 to obtain nucleotide sequences homologous to 14094 nucleic acid molecules of the invention. BLAST protein searches can be performed with the XBLAST program, score=50, wordlength=3 to obtain amino acid sequences homologous to 14094 protein molecules of the invention. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used.

Particular 14094 polypeptides of the present invention have an amino acid sequence substantially identical to the amino acid sequence of SEQ ID NO:2. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%, 91%, 92%, 93%, 94%, 95%, 96%, 97%, 98% or 99% identity to SEQ ID NO:2 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%, 91%, 92%, 93%, 94%, 95%, 96%, 97%, 98% or 99% identity to SEQ ID NO:1, 11, 3 or 13 are termed substantially identical.

"Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 14094 polypeptide described herein, e.g., a full-length 14094 protein or a fragment thereof, e.g., a biologically active portion of 14094 protein. Also included is a nucleic acid fragment suitable for use as a hybridization probe, which can be used, e.g., to identify a nucleic acid molecule encoding a polypeptide of the invention, 14094 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1 or 11, or a portion of any of these nucleotide sequences. In one embodiment, the nucleic acid molecule includes sequences encoding the human 14094 protein (i.e., "the coding region" of SEQ ID NO:1 or 11, as shown in SEQ ID NO:3 or 13), as well as 5' untranslated sequences. Alternatively, the nucleic acid molecule can include only the coding region of SEQ ID NO:1 or 11 (e.g., SEQ ID NO:3 or 13) and, e.g., no flanking sequences which normally accompany the subject sequence. In another embodiment, the nucleic acid molecule encodes a sequence corresponding to a fragment of the protein from about amino acid 217 to 443 of SEQ ID NO:2.

In another embodiment, an isolated nucleic acid molecule of the invention includes a nucleic acid molecule which is a complement of the nucleotide sequence shown in SEQ ID NO:1, 11, 13, or 3, or a portion of any of these nucleotide sequences. In other embodiments, the nucleic acid molecule of the invention is sufficiently complementary to the nucleotide sequence shown in SEQ ID NO:1, 11, 13, or 3, such that it can hybridize (e.g., under a stringency condition described herein) to the nucleotide sequence shown in SEQ ID NO:1, 11, 13, or 3, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1, 11, 13, or 3, or a portion, preferably of the same length, of any of these nucleotide sequences.

14094 Nucleic Acid Fragments

A nucleic acid molecule of the invention can include only a portion of the nucleic acid sequence of SEQ ID NO:1, 11, 13, or 3. For example, such a nucleic acid molecule can include a fragment which can be used as a probe or primer or a fragment encoding a portion of a 14094 protein, e.g., an immunogenic or biologically active portion of a 14094 protein. A fragment can comprise nucleotides about 643 to about 1331 of SEQ ID NO:1, which encodes a trypsin domain of human 14094. The nucleotide sequence determined from the cloning of the 14094 gene allows for the generation of probes and primers designed for use in identifying and/or cloning other 14094 family members, or fragments thereof, as well as 14094 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 30, 60, 100, 120, 200, 350 or more amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 14094 nucleic acid fragment can include a sequence corresponding to a trypsin domain.

14094 probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:1, 11, 13, or 3, or of a naturally occurring allelic variant or mutant of SEQ ID NO:1, 11, 13, or 3.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes, e.g., a trypsin domain from about amino acid 216 to 443 of SEQ ID NO:2; a histidine active site located at about amino acid 253 to about 258 of SEQ ID NO:2; a serine active site located at about amino acid 398 to 402 of SEQ ID NO:2, and corresponding regions of SEQ ID NO:12.

In another embodiment a set of primers is provided, e.g., primers suitable for use in a PCR, which can be used to amplify a selected region of a 14094 sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: a trypsin domain from about amino acid 216 to 443 of SEQ ID NO:2; a histidine active site located at about amino acid 253 to about 258 of SEQ ID NO:2; a serine active site located at about amino acid-398 to 402 of SEQ ID NO:2, and corresponding regions of SEQ ID NO:12.

A nucleic acid fragment can encode an epitope bearing region of a polypeptide described herein.

A nucleic acid fragment encoding a "biologically active portion of a 14094 polypeptide" can be prepared by isolating a portion of the nucleotide sequence of SEQ ID NO:1, 11, 13, or 3, which encodes a polypeptide having a 14094 biological activity (e.g., the biological activities of the 14094 proteins are described herein), expressing the encoded portion of the 14094 protein (e.g., by recombinant expression in vitro) and assessing the activity of the encoded portion of the 14094 protein. For example, a nucleic acid fragment encoding a biologically active portion of 14094 includes a trypsin domain, e.g., amino acid residues about 217 to 443 of SEQ ID NO:2, or corresponding regions of SEQ ID NO:12. A nucleic acid fragment encoding a biologically active portion of a 14094 polypeptide, may comprise a nucleotide sequence which is greater than 311 or more nucleotides in length.

In preferred embodiments, the fragment includes at least one, and preferably at least 5, 10, 15 nucleotides from about nucleotides 1 to 1270, 1579 to 1749, 1928 to 2614, and 2871 to 2948 of SEQ ID NO:1, or corresponding regions of SEQ ID NO:11.

In a preferred embodiment, the fragment has nucleotide sequence which other than (e.g., differs by at least one nucleotide from) the nucleotide sequence of 015393, AI 469095, AA 883068, AA 528170 and AW 193752.

In preferred embodiments, nucleic acids include a nucleotide sequence which is about 311, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800 or 2900 nucleotides in length and hybridizes under stringent hybridization conditions to a nucleic acid molecule of SEQ ID NO:1, SEQ ID NO:11, SEQ ID NO:3, or SEQ ID NO:13.

14094 Nucleic Acid Variants

The invention further encompasses nucleic acid molecules that differ from the nucleotide sequence shown in SEQ ID NO:1, 11, 13, or 3. Such differences can be due to degeneracy of the genetic code (and result in a nucleic acid which encodes the same 14094 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2 or SEQ ID NO:12. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in *E. coli*, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1, SEQ ID NO:11, SEQ ID NO:3, or SEQ ID NO:13, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the polypeptide sequence shown in SEQ ID NO:2, SEQ ID NO:12, or a fragment of this sequence. Such nucleic acid molecules can readily be identified as being able to hybridize under a stringency condition described herein, to the nucleotide sequence shown in SEQ ID NO 1, SEQ ID NO:11 or a fragment of the sequence. Nucleic acid molecules corresponding to orthologs, homologs, and allelic variants of the 14094 cDNAs of the invention can further be isolated by mapping to the same chromosome or locus as the 14094 gene.

Preferred variants include those that are correlated with modulating (stimulating and/or enhancing or inhibiting) cellular proliferation, differentiation, or tumorigenesis; modulating an immune response (i.e. modulating the complementation system); modulating hormone production; modulating the blood clotting cascade; or modulating proteolysis of protein substrates.

Allelic variants of 14094, e.g., human 14094, include both functional and non-functional proteins. Functional allelic variants are naturally occurring amino acid sequence variants of the 14094 protein within a population that maintain the ability to bind peptide sequences and exhibit proteolytic activity. Functional allelic variants will typically contain only conservative substitution of one or more amino acids of SEQ ID NO:2 or 12, or substitution, deletion or insertion of non-critical residues in non-critical regions of the protein. Non-functional allelic variants are naturally-occurring amino acid sequence variants of the 14094, e.g., human 14094, protein within a population that do not have the ability to bind peptide sequences and exhibit proteolytic activity. Non-functional allelic variants will typically contain a non-conservative substitution, a deletion, or insertion, or premature truncation of the amino acid sequence of SEQ ID NO:2 or 12, or a substitution, insertion, or deletion in critical residues or critical regions of the protein.

Moreover, nucleic acid molecules encoding other 14094 family members and, Thus, which have a nucleotide sequence which differs from the 14094 sequences of SEQ ID NO:1, 11, 13, or 3, are intended to be within the scope of the invention.

Antisense Nucleic Acid Molecules, Ribozymes and Modified 14094 Nucleic Acid Molecules In another aspect, the invention features, an isolated nucleic acid molecule which is antisense to 14094. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 14094 coding strand, or to only a portion thereof (e.g., the coding region of human 14094 corresponding to SEQ ID NO:3 or 13). In another embodiment, the antisense nucleic acid molecule is antisense to a "noncoding region" of the coding strand of a nucleotide sequence encoding 14094 (e.g., the 5' and 3' untranslated regions).

An antisense nucleic acid can be designed such that it is complementary to the entire coding region of 14094 mRNA, but more preferably is an oligonucleotide which is antisense to only a portion of the coding or noncoding region of 14094 mRNA. For example, the antisense oligonucleotide can be complementary to the region surrounding the translation start site of 14094 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 14094 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'—O— methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. A ribozyme having specificity for a 14094-encoding nucleic acid can include one or more sequences complementary to the nucleotide sequence of a 14094 cDNA disclosed herein (i.e., SEQ ID NO:1, 11, 13, or 3), and a sequence having known catalytic sequence responsible for mRNA cleavage (see U.S. Pat. No. 5,093,246 or Haselhoff and Gerlach (1988) *Nature* 334:585–591). For example, a derivative of a *Tetrahymena* L-19 IVS RNA can be constructed in which the nucleotide sequence of the active site is complementary to the nucleotide sequence to be cleaved in a 14094-encoding mRNA. See, e.g., Cech et al. U.S. Pat. No. 4,987,071; and Cech et al. U.S. Pat. No. 5,116,742. Alternatively, 14094 mRNA can be used to select a catalytic RNA having a specific ribonuclease activity from a pool of RNA molecules. See, e.g., Bartel, D. and Szostak, J. W. (1993) *Science* 261:1411–1418.

14094 gene expression can be inhibited by targeting nucleotide sequences complementary to the regulatory region of the 14094 (e.g., the 14094 promoter and/or enhancers) to form triple helical structures that prevent transcription of the 14094 gene in target cells. See generally, Helene, C. (1991) *Anticancer Drug Des.* 6:569–84; Helene, C. i (1992) *Ann. N.Y. Acad. Sci.* 660:27–36; and Maher, L. J. (1992) *Bioassays* 14:807–15. The potential sequences that can be targeted for triple helix formation can be increased by creating a so-called "switchback" nucleic acid molecule. Switchback molecules are synthesized in an alternating 5'–3',3'–5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 14094 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech.* 19:17 and Faria et al. (2001) *Nature Biotech.* 19:40–44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic &Medicinal Chemistry* 4: 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670–675.

PNAs of 14094 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 14094 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958–976) or intercalating agents. (see, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 14094 nucleic acid of the invention, two complementary regions one having a fluorophore and one a quencher such that the molecular beacon is useful for quantitating the presence of the 14094 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 14094 Polypeptides

In another aspect, the invention features, an isolated 14094 protein, or fragment, e.g., a biologically active portion, for use as immunogens or antigens to raise or test (or more generally to bind) anti-14094 antibodies. 14094 protein can be isolated from cells or tissue sources using standard protein purification techniques. 14094 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and posttranslational events. The polypeptide can be expressed in systems, e.g., cultured cells, which result in substantially the same posttranslational modifications present when expressed the polypeptide is expressed in a native cell, or in systems which result in the alteration or omission of posttranslational modifications, e.g., glycosylation or cleavage, present when expressed in a native cell.

In a preferred embodiment, a 14094 polypeptide has one or more of the following characteristics:

(i) it exhibits proteolytic activity;

(ii) it has an amino acid composition, molecular weight of a 14094 polypeptide, e.g., a polypeptide of SEQ ID NO:2 or 12;

(iii) it has an overall sequence similarity of at least 60%, preferably at least 70, more preferably at least 80, 90, or 95%, with a polypeptide of SEQ ID NO:2 or 12;

(iv) it can be found in breast, kidney, liver, brain, and aorta;

(v) it has a trypsin domain with a sequence similarity which is preferably about 70%, 80%, 90% or 95%, with amino acid residues about 217 to about 443 of SEQ ID NO:2, or a corresponding region of SEQ ID NO:12; or (vi) it has at least 10, preferably at least 12, and most preferably at least 15 of the 20 cysteines found in the amino acid sequence of the native protein.

In a preferred embodiment the 14094 protein, or fragment thereof, differs from the corresponding sequence in SEQ ID NO:2 or 12. In one embodiment the 14094 protein or fragment thereof differs by at least one but by less than 15, 10 or 5 amino acid residues. In another it differs from the corresponding sequence in SEQ ID NO:2 or 12 by at least one residue but less than 20%, 15%, 10% or 5% of the residues in it differ from the corresponding sequence in SEQ ID NO:2 or 12. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in a trypsin domain. In another preferred embodiment one or more differences are in transmembrane domains or non-transmembrane domains.

Other embodiments include a protein that contain one or more changes in amino acid sequence, e.g., a change in an amino acid residue which is not essential for activity. Such 14094 proteins differ in amino acid sequence from SEQ ID NO:2 or 12, yet retain biological activity.

In one embodiment, the prottein includes an amino acid sequence at least about 60%, 65%, 70%, 75%, 80%, 85%, 90%, 95%, 98% or more homologous to SEQ ID NO:2 or 12.

A 14094 protein or fragment is provided which varies from the sequence of SEQ ID NO.2 or 12 in regions defined by amino acids about 1 to about 216, and from about amino acid 444 to about 455 by at least one but by less than 15, 10 or 5 amino acid residues in the protein or fragment, but which does not differ from SEQ ID NO:2 or 12 in regions defined by amino acids about 217 to about 443 (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 14094 protein includes at least one trypsin domain. Moreover, other biologically active portions, in which other regions of the protein are deleted, can be prepared by recombinant techniques and evaluated for one or more of the functional activities of a native 14094 protein.

In another embodiment, an active 14094 polypeptides is proteolytically processed from zymogen form to its mature and processed form, e.g., a polypeptide which is cleaved between Arg 216 of SEQ ID NO:2 and Ile 217 of SEQ ID NO:2, a polypeptide that includes about amino acids 217 to 453 of SEQ ID NO:2, or corresponding regions of SEQ ID NO:12. The mature and processed polypeptides may be covalently attached to another 14094 polypeptide fragment, e.g., by means of a disulfide bond.

In a preferred embodiment, the 14094 protein has an amino acid sequence shown in SEQ ID NO:2 or 12 In other embodiments, the 14094 protein is substantially identical to SEQ ID NO:2 or 12. In yet another embodiment, the 14094 protein is substantially identical to SEQ ID NO:2 or 0.12 and retains the functional activity of the protein of SEQ ID NO:2 or 12, as described in detail in the subsections above.

14094 Chimeric or Fusion Proteins

In another aspect, the invention provides 14094 chimeric or fusion proteins. As used herein, a 14094 "chimeric protein" or "fusion protein" includes a 14094 polypeptide linked to a non-14094 polypeptide. A "non-14094 polypeptide" refers to a polypeptide having an amino acid sequence corresponding to a protein which is not substantially homologous to the 14094 protein, e.g., a protein which is different from the 14094 protein and which is derived from the same or a different organism. The 14094 polypeptide of the fusion protein can correspond to all or a portion e.g., a fragment described herein of a 14094 amino acid sequence. In a preferred embodiment, a 14094 fusion protein includes at least one (or two) biologically active portion of a 14094 protein. The non-14094 polypeptide can be fused to the N-terminus or C-terminus of the 14094 polypeptide.

The fusion protein can include a moiety which has a high affinity for a ligand. For example, the fusion protein can be a GST-14094 fusion protein in which the 14094 sequences are fused to the C-terminus of the GST sequences. Such fusion proteins can facilitate the purification of recombinant 14094. Alternatively, the fusion protein can be a 14094 protein containing a heterologous signal sequence at its N-terminus. In certain host cells (e.g., mammalian host cells), expression and/or secretion of 14094 can be increased through use of a heterologous signal sequence.

Fusion proteins can include all or a part of a serum protein, e.g., an IgG constant region, or human serum albumin.

The 14094 fusion proteins of the invention can be incorporated into pharmaceutical compositions and administered to a subject in vivo. The 14094 fusion proteins can be used to affect the bioavailability of a 14094 substrate. 14094 fusion proteins may be useful therapeutically for the treatment of disorders caused by, for example, (i) aberrant modification or mutation of a gene encoding a 14094 protein; (ii) mis-regulation of the 14094 gene; and (iii) aberrant post-translational modification of a 14094 protein.

Moreover, the 14094-fusion proteins of the invention can be used as immunogens to produce anti-14094 antibodies in a subject, to purify 14094 ligands and in screening assays to identify molecules which inhibit the interaction of 14094 with a 14094 substrate.

Expression vectors are commercially available that already encode a fusion moiety (e.g., a GST polypeptide). A 14094-encoding nucleic acid can be cloned into such an expression vector such that the fusion moiety is linked in-frame to the 14094 protein.

Variants of 14094 Proteins

In another aspect, the invention also features a variant of a 14094 polypeptide, e.g., which functions as an agonist (mimetics) or as an antagonist. Variants of the 14094 proteins can be generated by mutagenesis, e.g., discrete point mutation, the insertion or deletion of sequences or the truncation of a 14094 protein. An agonist of the 14094 proteins can retain substantially the same, or a subset, of the biological activities of the naturally occurring form of a 14094 protein. An antagonist of a 14094 protein can inhibit one or more of the activities of the naturally occurring form of the 14094 protein by, for example, competitively modulating a 14094-mediated activity of a 14094 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 14094 protein.

Variants of a 14094 protein can be identified by screening combinatorial libraries of mutants, e.g., truncation mutants, of a 14094 protein for agonist or antagonist activity.

Libraries of fragments e.g., N terminal, C terminal, or internal fragments, of a 14094 protein coding sequence can be used to generate a variegated population of fragments for screening and subsequent selection of variants of a 14094 protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of 14094 proteins. Recursive ensemble mutagenesis (REM), a new technique which enhances the frequency of functional mutants in the libraries, can be used in combination with the screening assays to identify 14094 variants (Arkin and Yourvan (1992) *Proc. Natl. Acad. Sci. USA* 89:7811–7815; Delgrave et al. (1993) *Protein Engineering* 6:327–331).

Cell based assays can be exploited to analyze a variegated 14094 library. For example, a library of expression vectors can be transfected into a cell line, e.g., a cell line, which ordinarily responds to 14094 in a substrate-dependent manner. The transfected cells are then contacted with 14094 and the effect of the expression of the mutant on signaling by the 14094 substrate can be detected. Plasmid DNA can then be recovered from the cells which score for inhibition, or alternatively, potentiation of signaling by the 14094 substrate, and the individual clones further characterized.

In another aspect, the invention features a method of making a 14094 polypeptide, e.g., a peptide having a non-wild type activity, e.g., an antagonist, agonist, or super agonist of a naturally occurring 14094 polypeptide, e.g., a naturally occurring 14094 polypeptide. The method includes: altering the sequence of a 14094 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 14094 polypeptide a biological activity of a naturally occurring 14094 polypeptide. The method includes: altering the sequence, e.g., by substitution or deletion of one or more residues, of a 14094 polypeptide, e.g., altering the sequence of a non-conserved region, or a domain or residue described herein, and testing the altered polypeptide for the desired activity.

Anti-14094 Antibodies

In another aspect, the invention provides an anti-14094 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901–917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-14094 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 14094 polypeptide or fragment thereof. Examples of antigen-binding fragments of the anti-14094 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-14094 antibody can be a polyclonal or a monoclonal antibody. In other embodiments, the antibody can be recombinantly produced, e.g., produced by phage display or by combinatorial methods.

Phage display and combinatorial methods for generating anti-14094 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) *EMBO J.* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982, the contents of all of which are incorporated by reference herein).

In one embodiment, the anti-14094 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856–859; Green, L. L. et al. 1994 *Nature Genet.* 7:13–21; Morrison, S. L. et al. 1994 *Proc. Natl. Acad. Sci. USA* 81:6851–6855; Bruggeman et al. 1993 *Year Immunol* 7:3340; Tuaillon et al. 1993 *PNAS* 90:3720–3724; Bruggeman et al. 1991 *Eur J Immunol* 21:1323–1326).

An anti-14094 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041–1043); Liu et al. (1987) *PNAS* 84:3439–3443; Liu et al., 1987, *J. Immunol.* 139:3521–3526; Sun et al. (1987) *PNAS* 84:214–218; Nishimura et al., 1987, *Canc. Res.* 47:999–1005; Wood et al. (1985) *Nature* 314:446–449; and Shaw et al., 1988, *J Natl Cancer Inst.* 80:1553–1559).

A humanized or CDR-grafted antibody will have at least one or two but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 14094 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202–1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 14094 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552–525; Verhoeyan et al. 1988 *Science* 239:1534; Beidler et al. 1988 *J. Immunol.* 141:4053–4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12–16 of U.S. Pat. No. 5,585,089, the e.g., columns 12–16 of U.S. Pat. No. 5,585,089, the contents of which are hereby incorporated by reference. Other techniques for humanizing antibodies are described in Padlan et al. EP 519596 A1, published on Dec. 23, 1992.

In preferred embodiments an antibody can be made by immunizing with purified 14094 antigen, or a fragment thereof, e.g., a fragment described herein, membrane associated antigen, tissue, e.g., crude tissue preparations, whole cells, preferably living cells, lysed cells, or cell fractions, e.g., membrane fractions.

A full-length 14094 protein or, antigenic peptide fragment of 14094 can be used as an immunogen or can be used to identify anti-14094 antibodies made with other immunogens, e.g., cells, membrane preparations, and the like. The antigenic peptide of 14094 should include at least 8 amino acid residues of the amino acid sequence shown in SEQ ID NO:2 or 12 and encompasses an epitope of 14094. Preferably, the antigenic peptide includes at least 10 amino acid residues, more preferably at least 15 amino acid residues, even more preferably at least 20 amino acid residues, and most preferably at least 30 amino acid residues.

Fragments of 14094 which include from about amino acids 1 to 46, or 394 to 453 of SEQ ID NO:2 can be used to make, e.g., used as immunogens or used to characterize the specificity of an antibody, antibodies against hydrophilic regions of the 14094 protein. Similarly, a fragment of 14094 which includes from about amino acids 137 to 153 of SEQ ID NO:2 can be used to make an antibody against a hydrophobic region of the 14094 protein. A fragments of 14094 which includes residues about 70 to 453 of SEQ ID NO:2 can be used to make an antibody against an extracellular region of the 14094 protein. A fragments of 14094 which includes residues about 1 to 47 of SEQ ID NO:2 can be used to make an antibody against an intracellular region of the 14094 protein. A fragment of 14094 which includes residues about 217 to 443 of SEQ ID NO:2 can be used to make an antibody against the trypsin region of the 14094 protein. A fragment of 14094 which includes residues about 110 to 205 of SEQ ID NO:2 can be used to make an antibody against the scavenger receptor cysteine-rich domain of the 14094 protein. A fragment of 14094 which includes residues about 71 to 109 of SEQ ID NO:2 can be used to make an antibody against the LDL receptor domain of the 14094 protein. The corresponding regions of SEQ ID NO:12 can also be used to generate an antibody.

Antibodies reactive with, or specific for, any of these regions, or other regions or domains described herein are provided.

Antibodies which bind only native 14094 protein, only denatured or otherwise non-native 14094 protein, or which bind both, are with in the invention. Antibodies with linear or conformational epitopes are within the invention. Conformational epitopes can sometimes be identified by identifying antibodies which bind to native but not denatured 14094 protein.

Preferred epitopes encompassed by the antigenic peptide are regions of 14094 are located on the surface of the protein, e.g., hydrophilic regions, as well as regions with high antigenicity. For example, an Emini surface probability analysis of the human 14094 protein sequence can be used to indicate the regions that have a particularly high probability of being localized to the surface of the 14094 protein and are thus likely to constitute surface residues useful for targeting antibody production.

In a preferred embodiment the antibody can bind to the extracellular portion of =1 the 14094 protein, e.g., it can bind to a whole cell which expresses the 14094 protein. In another embodiment, the antibody binds an intracellular portion of the 14094 protein. In preferred embodiments antibodies can bind one or more of purified antigen, membrane associated antigen, tissue, e.g., tissue sections, whole cells, preferably living cells, lysed cells, cell fractions, e.g., membrane fractions.

The anti-14094 antibody can be a single chain antibody. A single-chain antibody (scFV) may be engineered (see, for example, Colcher, D. et al. (1999) *Ann N Y Acad Sci* 880:263–80; and Reiter, Y. (1996) *Clin Cancer Res* 2:245–52). The single chain antibody can be dimerized or multimerized to generate multivalent antibodies having specificities for different epitopes of the same target 14094 protein.

In a preferred embodiment the antibody has: effector function; and can fix complement. In other embodiments the antibody does not; recruit effector cells; or fix complement.

In a preferred embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

In a preferred embodiment, an anti-14094 antibody alters (e.g., increases or decreases) the proteolytic activity of a 14094 polypeptide. For example, the antibody can bind at or in proximity to the active site, e.g., to an epitope that includes a residue located from about 250 to 260 or 390 to 410 of SEQ ID NO:2, or a corresponding region of SEQ ID NO:12.

The antibody can be coupled to a toxin, e.g., a polypeptide toxin, e.g., ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-14094 antibody (e.g., monoclonal antibody) can be used to isolate 14094 by standard techniques, such as affinity chromatography or immunoprecipitation. Moreover, an anti-14094 antibody can be used to detect 14094 protein (e.g., in a cellular lysate or cell supernatant) in order to evaluate the abundance and pattern of expression of the protein. Anti-14094 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention also includes a nucleic acids which encodes an anti-14094 antibody, e.g., an anti-14094 antibody described herein. Also included are vectors which include the nucleic acid and sells transformed with the nucleic acid, particularly cells which are useful for producing an antibody, e.g., mammalian cells, e.g. CHO or lymphatic cells.

The invention also includes cell lines, e.g., hybridomas, which make an anti-14094 antibody, e.g., and antibody described herein, and method of using said cells to make a 14094 antibody.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 14094 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 14094 proteins, mutant forms of 14094 proteins, fusion proteins, and the like).

The recombinant expression vectors of the invention can be designed for expression of 14094 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:3140), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 14094 activity assays, (e.g., direct assays or competitive assays described in detail below), or to generate antibodies specific for 14094 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif.

119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

The 14094 expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a 14094 nucleic acid molecule within a recombinant expression vector or a 14094 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 14094 protein can be expressed in bacterial cells (such as *E. coli*), insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 14094 protein. Accordingly, the invention further provides methods for producing a 14094 protein using the host cells of the invention. In one embodiment, the method includes culturing the host cell of the invention (into which a recombinant expression vector encoding a 14094 protein has been introduced) in a suitable medium such that a 14094 protein is produced. In another embodiment, the method further includes isolating a 14094 protein from the medium or the host cell.

In another aspect, the invention features a cell or purified preparation of cells which include a 14094 transgene, or which otherwise misexpress 14094. The cell preparation can consist of human or non-human cells, e.g., rodent cells, e.g., mouse or rat cells, rabbit cells, or pig cells. In preferred embodiments, the cell or cells include a 14094 transgene, e.g., a heterologous form of a 14094, e.g., a gene derived from humans (in the case of a non-human cell). The 14094 transgene can be misexpressed, e.g., overexpressed or underexpressed. In other preferred embodiments, the cell or cells include a gene that mis-expresses an endogenous 14094, e.g., a gene the expression of which is disrupted, e.g., a knockout. Such cells can serve as a model for studying disorders that are related to mutated or mis-expressed 14094 alleles or for use in drug screening.

In another aspect, the invention features a human cell, e.g., a hematopoietic stem cell, transformed with nucleic acid which encodes a subject 14094 polypeptide.

Also provided are cells, preferably human cells, e.g., human hematopoietic or fibroblast cells, in which an endogenous 14094 is under the control of a regulatory sequence that does not normally control the expression of the endogenous 14094 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 14094 gene. For example, an endogenous 14094 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 14094 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol.* 14:1107; Joki et al. (2001) *Nat. Biotechnol.* 19:35; and U.S. Pat. No. 5,876,742. Production of 14094 polypeptide can be regulated in the subject by administering an agent (e.g., a steroid hormone) to the subject. In another preferred embodiment, the implanted recombinant cells express and secrete an antibody specific for a 14094 polypeptide. The antibody can be any antibody or any antibody derivative described herein.

Transgenic Animals

The invention provides non-human transgenic animals. Such animals are useful for studying the function and/or activity of a 14094 protein and for identifying and/or evaluating modulators of 14094 activity. As used herein, a "transgenic animal" is a non-human *animal*, preferably a *mammal*, more preferably a rodent such as a rat or *mouse*, in which one or more of the cells of the animal includes a *transgene*. *Other* examples of transgenic animals include *non-human primates, sheep, dogs, cows, goats, chickens, amphibians*, and the *like*. A transgene is exogenous DNA or a *rearrangement*, *e.g.*, a deletion of endogenous chromosomal DNA, which preferably is integrated into or occurs in the genome of the cells of a transgenic *animal*. A transgene can direct the expression of an encoded gene product in one or more cell types or tissues of the transgenic *animal*, other *transgenes*, *e.g.*, a *knockout*, reduce *expression*. T*hus*, a transgenic animal can be one in which an endogenous 14094 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 14094 protein to particular cells. A transgenic founder animal can be identified based upon the presence of a 14094 transgene in its genome and/or expression of 14094 mRNA in tissues or cells of the animals. A transgenic founder animal can then be used to breed additional animals carrying the transgene. Moreover, transgenic animals carrying a transgene encoding a 14094 protein can further be bred to other transgenic animals carrying other transgenes.

14094 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); c) methods of treatment (e.g., therapeutic and prophylactic); and d) in vitro modification of a peptide substrate.

The isolated nucleic acid molecules of the invention can be used, for example, to express a 14094 protein (e.g., via a recombinant expression vector in a host cell in gene therapy applications), to detect a 14094 mRNA (e.g., in a biological sample) or a genetic alteration in a 14094 gene, and to modulate 14094 activity, as described further below. The 14094 proteins can be used to treat disorders characterized by insufficient or excessive production of a 14094 substrate or production of 14094 inhibitors. In addition, the 14094 proteins can be used to screen for naturally occurring 14094 substrates, to screen for drugs or compounds which modulate 14094 activity, as well as to treat disorders characterized by insufficient or excessive production of 14094 protein or production of 14094 protein forms which have decreased, aberrant or unwanted activity compared to 14094 wild type protein (e.g., a cell differentiative or proliferative disorder). Moreover, the anti-14094 antibodies of the invention can be used to detect and isolate 14094 proteins, regulate the bioavailability of 14094 proteins, and modulate 14094 activity.

Further, 14094 polypeptides can be used to process substrate polypeptides (or peptides) in vitro. The processed substrate polypeptide can be analyzed to identify substrate fragments that are produced by digestion with 14094 polypeptides. Moreover, the 14094 can utilized to digest isolated, but unassigned polypeptides prior to mass spectroscopy.

Processed substrate polypeptides can be also used in a pharmaceutical composition.

A method of evaluating a compound for the ability to interact with, e.g., bind, a subject 14094 polypeptide is provided. The method includes: contacting the compound with the subject 14094 polypeptide; and evaluating ability of the compound to interact with, e.g., to bind or form a complex with the subject 14094 polypeptide. This method can be performed in vitro, e.g., in a cell free system, or in vivo, e.g., in a two-hybrid interaction trap assay. This method can be used to identify naturally occurring molecules that interact with subject 14094 polypeptide. It can also be used to find natural or synthetic inhibitors of subject 14094 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 14094 proteins, have a stimulatory or inhibitory effect on, for example, 14094 expression or 14094 activity, or have a stimulatory or inhibitory effect on, for example, the expression or activity of a 14094 substrate. Compounds thus identified can be used to modulate the activity of target gene products (e.g., 14094 genes) in a therapeutic protocol, to elaborate the biological function of the target gene product, or to identify compounds that disrupt normal target gene interactions.

In one embodiment, the invention provides assays for screening candidate or test compounds which are substrates of a 14094 protein or polypeptide or a biologically active portion thereof. In another embodiment, the invention provides assays for screening candidate or test compounds that bind to or modulate an activity of a 14094 protein or polypeptide or a biologically active portion thereof.

In one embodiment, a proteolytic activity of a 14094 protein can be assayed using a fluorescent substrate, such as a small peptide-amino methyl coumarin (AMC) derivative.

Possible substrates include: p-tosyl-L-arginine methyl ester; N-benzoyl-L-arginine p-nitroanilide; N-alpha-benzoyl-L-arginine ethyl ester; Benzoyl-D,L-arginine-p-nitroanilide; H-D-Phe-Pip-Arg-p-nitroanilide; Bz-Ile-Glu-Gly-Arg-p-nitroanilide; H-D-Ile-Pro-Arg-p-nitroanilide; N-benzoyl-Leu-Ser-Arg-p-nitroanilide (Kazama et al. (1995) J. Biol. Chem. 270: 66–72).

The 14094 polypeptide can be tagged as described herein, purified or partially purified and assayed for substrate hydrolysis in a variety of assay conditions. Samples which show no activity at 0.1 mM protein can be considered in active under those conditions. Assay conditions such as buffer, pH, and substrate, can be permuted until an appropriate one is found (e.g. pH 6.0 to 9.0, including or not including calcium ions).

Assaying a 14094 protein activity in the presence of inhibitors can be used to determine the nature of the catalytic activity. Inhibitors that can be tested include: L-1-Chloro-3-tosylamido-4-phenyl-2-butanone, Soybean inhibitor, benzamidine, p-Nitrophenyl-p-guanidino benzoate (trypsin-like enzyme), Tosyl-L-lysine chloromethyl ketone, and Tosyl-L-arginine chloromethyl ketone.

The assay can include additional controls and steps to insure that the observed activity results from a 14094 polypeptide. For example, control samples, e.g., samples produced from cells transformed with a control vector instead of a vector overexpressing a 14094 nucleic acid, can be tested in parallel. The activity can also be tracked in chromatography fractions, e.g., to determine if the activity and the 14094 polypeptide co-purify.

Additional assays and conditions are described, e.g., in Yamaoka et al. (1998) *J Biol Chem* 273:11895–11901, and Thien-Khai et al. (1997) *J Biol Chem* 272:31315–31320.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner, U.S. Pat. No. 5,223, 409), spores (Ladner U.S. Pat. No. 5,223,409), plasmids (Cull et al. (1992) *Proc Natl Acad Sci USA* 89:1865–1869) or on phage (Scott and Smith (1990) *Science* 249:386–390; Devlin (1990) *Science* 249:404406; Cwirla et al. (1990) *Proc. Natl. Acad. Sci.* 87:6378–6382; Felici (1991) *J. Mol. Biol.* 222:301–310; Ladner supra.).

In one embodiment, an assay is a cell-based assay in which a cell which expresses a 14094 protein or biologically active portion thereof is contacted with a test compound, and the ability of the test compound to modulate 14094 activity is determined. Determining the ability of the test compound to modulate 14094 activity can be accomplished by monitoring, for example, proteolytic activity. The cell, for example, can be of mammalian origin, e.g., human.

The ability of the test compound to modulate 14094 binding to a compound, e.g., a 14094 substrate, or to bind to 14094 can also be evaluated. This can be accomplished, for example, by coupling the compound, e.g., the substrate, with a radioisotope or enzymatic label such that binding of the compound, e.g., the substrate, to 14094 can be determined by detecting the labeled compound, e.g., substrate, in a complex. Alternatively, 14094 could be coupled with a radioisotope or enzymatic label to monitor the ability of a test compound to modulate 14094 binding to a 14094 substrate in a complex. For example, compounds (e.g., 14094 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 14094 substrate) to interact with 14094 with or without the labeling of any of the interactants can be evaluated. For example, a microphysiometer can be used to detect the interaction of a compound with 14094 without the labeling of either the compound or the 14094. McConnell, H. M. et al. (1992) *Science* 257: 1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 14094.

In yet another embodiment, a cell-free assay is provided in which a 14094 protein or biologically active portion thereof is contacted with a test compound and the ability of the test compound to bind to the 14094 protein or biologically active portion thereof is evaluated. Preferred biologically active portions of the 14094 proteins to be used in assays of the present invention include fragments which participate in interactions with non-14094 molecules, e.g., fragments with high surface probability scores.

Soluble and/or membrane-bound forms of isolated proteins (e.g., 14094 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 14094 protein to bind to a target molecule can be accomplished using real-time Biomolecular Interaction Analysis (BIA) (see, e.g., Sjolander, S. and Urbaniczky, C. (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 14094, an anti-14094 antibody or its target molecule to facilitate separation of complexed from uncomplexed forms of one or both of the proteins, as well as to accommodate automation of the assay. Binding of a test compound to a 14094 protein, or interaction of a 14094 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/14094 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 14094 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 14094 binding or activity determined using standard techniques.

Other techniques for immobilizing either a 14094 protein or a target molecule on matrices include using conjugation of biotin and streptavidin. Biotinylated 14094 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 14094 protein or target molecules but which do not interfere with binding of the 14094 protein to its target molecule. Such antibodies can be derivatized to the wells of the plate, and unbound target or 14094 protein trapped in the wells by antibody conjugation. Methods for detecting such complexes, in addition to those described above for the GST-immobilized complexes, include immunodetection of complexes using antibodies reactive with the 14094 protein or target molecule, as well as enzyme-linked assays which rely on detecting an enzymatic activity associated with the 14094 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284–7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141–8; Hage, D. S., and Tweed, S. A. (1997) *J Chromatogr B Biomed Sci Appl.* 699:499–525). Further, fluorescence energy transfer may also be conveniently utilized, as described herein, to detect binding without further purification of the complex from solution.

In a preferred embodiment, the assay includes contacting the 14094 protein or biologically active portion thereof with a known compound which binds 14094 to form an assay mixture, contacting the assay mixture with a test compound, and determining the ability of the test compound to interact with a 14094 protein, wherein determining the ability of the test compound to interact with a 14094 protein includes determining the ability of the test compound to preferentially bind to 14094 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 14094 genes herein identified. In an alternative embodiment, the invention provides methods for determining the ability of the test compound to modulate the activity of a 14094 protein through modulation of the activity of a downstream effector of a 14094 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 14094 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268: 12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 14094 ("14094-binding proteins" or "14094-bp") and are involved in 14094 activity. Such 14094-bps can be activators or inhibitors of signals by the 14094 proteins or 14094 targets as, for example, downstream elements of a 14094-mediated signaling pathway.

The two-hybrid system is based on the modular nature of most transcription factors, which consist of separable DNA-binding and activation domains. Briefly, the assay utilizes two different DNA constructs. In one construct, the gene that codes for a 14094 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 14094 protein can be the fused to the activator domain.) If the "bait" and the "prey" proteins are able to interact, in vivo, forming a 14094-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 14094 protein.

In another embodiment, modulators of 14094 expression are identified. For example, a cell or cell free mixture is contacted with a candidate compound and the expression of 14094 mRNA or protein evaluated relative to the level of expression of 14094 mRNA or protein in the absence of the candidate compound. When expression of 14094 mRNA or protein is greater in the presence of the candidate compound than in its absence, the candidate compound is identified as a stimulator of 14094 mRNA or protein expression. Alternatively, when expression of 14094 mRNA or protein is less (statistically significantly less) in the presence of the candidate compound than in its absence, the candidate compound is identified as an inhibitor of 14094 mRNA or protein expression. The level of 14094 mRNA or protein expression can be determined by methods described herein for detecting 14094 mRNA or protein.

In another aspect, the invention pertains to a combination of two or more of the assays described herein. For example, a modulating agent can be identified using a cell-based or a cell free assay, and the ability of the agent to modulate the activity of a 14094 protein can be confirmed in vivo, e.g., in an animal such as an animal model for cancer.

This invention further pertains to novel agents identified by the above-described screening assays. Accordingly, it is within the scope of this invention to further use an agent identified as described herein (e.g., a 14094 modulating agent, an antisense 14094 nucleic acid molecule, a 14094-specific antibody, or a 14094-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 14094 with a disease; (ii) identify an individual from a minute biological sample (tissue typing); and (iii) aid in forensic identification of a biological sample. These applications are described in the subsections below.

Chromosome Mapping

The 14094 nucleotide sequences or portions thereof can be used to map the location of the 14094 genes on a chromosome. This process is called chromosome mapping. Chromosome mapping is useful in correlating the 14094 sequences with genes associated with disease.

Briefly, 14094 genes can be mapped to chromosomes by preparing PCR primers (preferably 15–25 bp in length) from the 14094 nucleotide sequences. These primers can then be used for PCR screening of somatic cell hybrids containing individual human chromosomes. Only those hybrids containing the human gene corresponding to the 14094 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919–924).

Other mapping strategies e.g., in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries can be used to map 14094 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques ((1988) Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the 14094 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 14094 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 14094 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 or SEQ ID NO:11 can provide positive individual identification with a panel of perhaps 10 to 1,000 primers which each yield a noncoding amplified sequence of 100 bases. If predicted coding sequences, such as those in SEQ ID NO:3 or 13 are used, a more appropriate number of primers for positive individual identification would be 500–2,000.

If a panel of reagents from 14094 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 14094 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 or 11 (e.g., fragments derived from the noncoding regions of SEQ ID NO:1 or 11 having a length of at least 20 bases, preferably at least 30 bases) are particularly appropriate for this use.

The 14094 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 14094 probes can be used to identify tissue by species and/or by organ type.

In a similar fashion, these reagents, e.g., 14094 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 14094.

Such disorders include, e.g., a disorder associated with the misexpression of a 14094 molecule; a disorder of the immune, or blood clotting system.

The method includes one or more of the following:

detecting, in a tissue of the subject, the presence or absence of a mutation which affects the expression of the 14094 gene, or detecting the presence or absence of a mutation in a region which controls the expression of the gene, e.g., a mutation in the 5' control region;

detecting, in a tissue of the subject, the presence or absence of a mutation which alters the structure of the 14094 gene;

detecting, in a tissue of the subject, the misexpression of the 14094 gene, at the mRNA level, e.g., detecting a non-wild type level of a mRNA;

detecting, in a tissue of the subject, the misexpression of the gene, at the protein level, e.g., detecting a non-wild type level of a 14094 polypeptide.

In preferred embodiments the method includes: ascertaining the existence of at least one of: a deletion of one or more nucleotides from the 14094 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1 or 11, or naturally occurring mutants thereof or 5' or 3' flanking sequences naturally associated with the 14094 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 14094 gene; the presence of a non-wild type splicing pattern of a messenger RNA transcript of the gene; or a non-wild type level of 14094.

Methods of the invention can be used prenatally or to determine if a subject's offspring will be at risk for a disorder.

In preferred embodiments the method includes determining the structure of a 14094 gene, an abnormal structure being indicative of risk for the disorder.

In preferred embodiments the method includes contacting a sample from the subject with an antibody to the 14094 protein or a nucleic acid, which hybridizes specifically with the gene. These and other embodiments are discussed below.

Diagnostic and Prognostic Assays

Diagnostic and prognostic assays of the invention include method for assessing the expression level of 14094 molecules and for identifying variations and mutations in the sequence of 14094 molecules.

Expression Monitoring and Profiling. The presence, level, or absence of 14094 protein or nucleic acid in a biological sample can be evaluated by obtaining a biological sample from a test subject and contacting the biological sample with a compound or an agent capable of detecting 14094 protein or nucleic acid (e.g., mRNA, genomic DNA) that encodes 14094 protein such that the presence of 14094 protein or nucleic acid is detected in the biological sample. The term "biological sample" includes tissues, cells and biological fluids isolated from a subject, as well as tissues, cells and fluids present within a subject. A preferred biological sample is serum. The level of expression of the 14094 gene can be measured in a number of ways, including, but not limited to: measuring the mRNA encoded by the 14094 genes; measuring the amount of protein encoded by the 14094 genes; or measuring the activity of the protein encoded by the 14094 genes.

The level of mRNA corresponding to the 14094 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 14094 nucleic acid, such as the nucleic acid of SEQ ID NO:1 or 11, or a portion thereof, such as an oligonucleotide of at least 7, 15, 30, 50, 100, 250 or 500 nucleotides in length and sufficient to specifically hybridize under stringent conditions to 14094 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 14094 genes.

The level of mRNA in a sample that is encoded by one of 14094 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189–193), self sustained sequence replication (Guatelli et al., (1990) *Proc. Natl. Acad. Sci. USA* 87:1874–1878), transcriptional amplification system (Kwoh et al., (1989), *Proc. Natl. Acad. Sci. USA* 86:1173–1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 14094 gene being analyzed.

In another embodiment, the methods further contacting a control sample with a compound or agent capable of detecting 14094 mRNA, or genomic DNA, and comparing the presence of 14094 mRNA or genomic DNA in the control sample with the presence of 14094 mRNA or genomic DNA in the test sample. In still another embodiment, serial analysis of gene expression, as described in U.S. Pat. No. 5,695,937, is used to detect 14094 transcript levels.

A variety of methods can be used to determine the level of protein encoded by 14094. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 14094 protein in a biological sample in vitro as well as in vivo. In vitro techniques for detection of 14094 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 14094 protein include introducing into a subject a labeled anti-14094 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-14094 antibody positioned on an antibody array (as described below). The sample can be detected, e.g., with avidin coupled to a fluorescent label.

In another embodiment, the methods further include contacting the control sample with a compound or agent capable of detecting 14094 protein, and comparing the presence of 14094 protein in the control sample with the presence of 14094 protein in the test sample.

The invention also includes kits for detecting the presence of 14094 in a biological sample. For example, the kit can include a compound or agent capable of detecting 14094 protein or mRNA in a biological sample; and a standard. The compound or agent can be packaged in a suitable container. The kit can further comprise instructions for using the kit to detect 14094 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 14094 expression or activity. As used herein, the term "unwanted" includes an unwanted phenomenon involved in a biological response such as cancer or deregulated cell proliferation.

In one embodiment, a disease or disorder associated with aberrant or unwanted 14094 expression or activity is identified. A test sample is obtained from a subject and 14094 protein or nucleic acid (e.g., mRNA or genomic DNA) is evaluated, wherein the level, e.g., the presence or absence, of 14094 protein or nucleic acid is diagnostic for a subject having or at risk of developing a disease or disorder associated with aberrant or unwanted 14094 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 14094 expression or activity. For example, such methods can be used to determine whether a subject can be effectively treated with an agent for a cell proliferative or differentiative disorder.

In another aspect, the invention features a computer medium having a plurality of digitally encoded data records. Each data record includes a value representing the level of expression of 14094 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 14094 (e.g., other genes associated with a 14094-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 14094 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a a cell proliferative disorder in a subject wherein an increase in 14094 expression is an indication that the subject has or is disposed to having a cell proliferative disorder. The method can be used to monitor a treatment for a cell proliferative disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 14094 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 14094 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 14094 expression.

Arrays and Uses Thereof

In another aspect, the invention features an array that includes a substrate having a plurality of addresses. At least one address of the plurality includes a capture probe that binds specifically to a 14094 molecule (e.g., a 14094 nucleic acid or a 14094 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 14094 nucleic acid, e.g., the sense or anti-sense strand. In one preferred embodiment, a subset of addresses of the plurality of addresses has a nucleic acid capture probe for 14094. Each address of the subset can include a capture probe that hybridizes to a different region of a 14094 nucleic acid. In another preferred embodiment, addresses of the subset include a capture probe for a 14094 nucleic acid. Each address of the subset is unique, overlapping, and complementary to a different variant of 14094 (e.g., an allelic variant, or all possible hypothetical variants). The array can be used to sequence 14094 by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 14094 polypeptide or fragment thereof. The polypeptide can be a naturally-occurring interaction partner of 14094 polypeptide. Preferably, the polypeptide is an antibody, e.g., an antibody described herein (see "Anti-14094 Antibodies," above), such as a monoclonal antibody or a single-chain antibody.

In another aspect, the invention features a method of analyzing the expression of 14094. The method includes providing an array as described above; contacting the array with a sample and detecting binding of a 14094-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 14094. If a sufficient number of diverse samples is analyzed, clustering (e.g., hierarchical clustering, k-means clustering, Bayesian clustering and the like) can be used to identify other genes which are co-regulated with 14094. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell—cell interactions on 14094 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell—cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 14094-associated disease or disorder; and processes, such as a cellular transformation associated with a 14094-associated disease or disorder. The method can also evaluate the treatment and/or progression of a 14094-associated disease or disorder The array is also useful for ascertaining differential expression patterns of one or more genes in normal and abnormal cells. This provides a battery of genes (e.g., including 14094) that could serve as a molecular target for diagnosis or therapeutic intervention.

In another aspect, the invention features an array having a plurality of addresses. Each address of the plurality includes a unique polypeptide. At least one address of the plurality has disposed thereon a 14094 polypeptide or fragment thereof. Methods of producing polypeptide arrays are described in the art, e.g., in De Wildt et al. (2000). *Nature Biotech.* 18, 989–994; Lueking et al. (1999). *Anal. Biochem.* 270, 103–111; Ge, H. (2000). *Nucleic Acids Res.* 28, e3, I–VII; MacBeath, G., and Schreiber, S. L. (2000). *Science* 289, 1760–1763; and WO 99/51773A1. In a preferred embodiment, each addresses of the plurality has disposed thereon a polypeptide at least 60, 70, 80, 85, 90, 95 or 99% identical to a 14094 polypeptide or fragment thereof. For example, multiple variants of a 14094 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 14094 binding compound, e.g., an antibody in a sample from a subject with specificity for a 14094 polypeptide or the presence of a 14094-binding protein or ligand.

The array is also useful for ascertaining the effect of the expression of a gene on the expression of other genes in the same cell or in different cells (e.g., ascertaining the effect of 14094 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 14094 or from a cell or subject in which a 14094 mediated response has been elicited, e.g., by contact of the cell with 14094 nucleic acid or protein, or administration to the cell or subject 14094 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 14094 (or does not express as highly as in the case of the 14094 positive plurality of capture probes) or from a cell or subject which in which a 14094 mediated response has not been elicited (or has been elicited to a lesser extent than in the first sample); contacting the array with one or more inquiry probes (which is preferably other than a 14094 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 14094 or from a cell or subject in which a 14094-mediated response has been elicited, e.g., by contact of the cell with 14094 nucleic acid or protein, or administration to the cell or subject 14094 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 14094 (or does not express as highly as in the case of the 14094 positive plurality of capture probes) or from a cell or subject which in which a 14094 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 14094, e.g., analyzing structure, function, or relatedness to other nucleic acid or amino acid sequences. The method includes: providing a 14094 nucleic acid or amino acid sequence; comparing the 14094 sequence with one or more preferably a plurality of sequences from a collection of sequences, e.g., a nucleic acid or protein sequence database; to thereby analyze 14094.

Detection of Variations or Mutations

The methods of the invention can also be used to detect genetic alterations in a 14094 gene, thereby determining if a subject with the altered gene is at risk for a disorder characterized by misregulation in 14094 protein activity or nucleic acid expression, such as a cell proliferative or differentiative disorder. In preferred embodiments, the methods include detecting, in a sample from the subject, the presence or absence of a genetic alteration characterized by at least one of an alteration affecting the integrity of a gene encoding a 14094-protein, or the mis-expression of the 14094 gene. For example, such genetic alterations can be detected by ascertaining the existence of at least one of 1) a deletion of one or more nucleotides from a 14094 gene; 2) an addition of one or more nucleotides to a 14094 gene; 3) a substitution of one or more nucleotides of a 14094 gene, 4) a chromosomal rearrangement of a 14094 gene; 5) an alteration in the level of a messenger RNA transcript of a 14094 gene, 6) aberrant modification of a 14094 gene, such as of the methylation pattern of the genomic DNA, 7) the presence of a non-wild type splicing pattern of a messenger RNA transcript of a 14094 gene, 8) a non-wild type level of a 14094-protein, 9) allelic loss of a 14094 gene, and 10) inappropriate post-translational modification of a 14094-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 14094-gene. This method can include the steps of collecting a sample of cells from a subject, isolating nucleic acid (e.g., genomic, mRNA or both) from the sample, contacting the nucleic acid sample with one or more primers which specifically hybridize to a 14094 gene under conditions such that hybridization and amplification of the 14094-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 14094 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 14094 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 14094 nucleic acid or a putative variant (e.g., allelic variant) thereof. A probe can have one or more mismatches to a region of a 14094 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 14094 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 14094 gene and detect mutations by comparing the sequence of the sample 14094 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 14094 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 14094 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 14094 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control 14094 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl. Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 14094 nucleic acid.

In a preferred embodiment the set includes a first and a second oligonucleotide. The first and second oligonucleotide can hybridize to the same or to different locations of SEQ ID NO:1 or 11 or the complement of SEQ ID NO:1 or 11. Different locations can be different but overlapping, or non-overlapping on the same strand. The first and second oligonucleotide can hybridize to sites on the same or on different strands.

The set can be useful, e.g., for identifying SNP's, or identifying specific alleles of 14094. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 14094 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 14094 gene.

Use of 14094 Molecules as Surrogate Markers

The 14094 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 14094 molecules of the invention may be detected, and may be correlated with one or more biological states in vivo. For example, the 14094 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 14094 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 14094 marker) transcription or expression, the amplified marker may be in a quantity which is more readily detectable than the drug itself. Also, the marker may be more easily detected due to the nature of the marker itself; for example, using the methods described herein, anti-14094 antibodies may be employed in an immune-based detection system for a 14094 protein marker, or 14094-specific radiolabeled probes may be used to detect a 14094 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am, J Health-Syst Pharm.* 56 Suppl. 3: S16–S20.

The 14094 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 14094 protein or RNA) for specific tumor markers in a subject, a drug or course of treatment may be selected that is optimized for the treatment of the specific tumor likely to be present in the subject. Similarly, the presence or absence of a specific sequence mutation in 14094 DNA may correlate 14094 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-14094 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 14094 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 14094 molecules of the present invention or 14094 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 14094 expression or activity, by administering to the subject a 14094 or an agent which modulates 14094 expression or at least one 14094 activity. Subjects at risk for a disease which is caused or contributed to by aberrant or unwanted 14094 expression or activity can be identified by, for example, any or a combination of diagnostic or prognostic assays as described herein. Administration of a prophylactic agent can occur prior to the manifestation of symptoms characteristic of the 14094 aberrance, such that a disease or disorder is prevented or, alternatively, delayed in its progression. Depending on the type of 14094 aberrance, for example, a 14094, 14094 agonist or 14094 antagonist agent can be used for treating the subject. The appropriate agent can be determined based on screening assays described herein.

It is possible that some 14094 disorders can be caused, at least in part, by an abnormal level of gene product, or by the presence of a gene product exhibiting abnormal activity. As such, the reduction in the level and/or activity of such gene products would bring about the amelioration of disorder symptoms.

As described above, the 14094 mRNA levels are significantly upregulated in cancerous cells and tissues of the breast, ovary, colon, liver, and lung (see the Examples, below). The 14094 mRNA is expressed, although at lower levels, in normal tissues from the breast, kidney, liver, brain, and aorta. Accordingly, it is likely that 14094 molecules may be involved in disorders characterized by aberrant activity of these non-malignant cells. Thus, the 14094 molecules can act as novel diagnostic targets and therapeutic agents for controlling disorders involving aberrant activity in these cells.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromatosis, including Type I neurofibromatosis (NF 1) and TYPE 2 neurofibromatosis (NF2), tuberous sclerosis, and Von Hippel-Lindau disease.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders of the liver other than the neoplastic conditions described above include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Disorders of the breast other than the neoplastic conditions described above include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schonlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

As discussed, successful treatment of 14094 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 14094 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 14094 expression is through the use of aptamer molecules specific for 14094 protein. Aptamers are nucleic acid molecules having a tertiary structure which permits them to specifically bind to protein ligands (see, e.g., Osborne, et al. (1997) Curr. Opin. Chem Biol. 1: 5–9; and Patel, D. J. (1997) Curr Opin Chem Biol 1:32–46). Since nucleic acid molecules may in many cases be more conveniently introduced into target cells than therapeutic protein molecules may be, aptamers offer a method by which 14094 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 14094 disorders. For a description of antibodies, see the Antibody section above.

In circumstances wherein injection of an animal or a human subject with a 14094 protein or epitope for stimulating antibody production is harmful to the subject, it is possible to generate an immune response against 14094 through the use of anti-idiotypic antibodies (see, for example, Herlyn, D. (1999) Ann Med 31:66–78; and Bhattacharya-Chatterjee, M., and Foon, K. A. (1998) Cancer Treat Res. 94:51–68). If an anti-idiotypic antibody is introduced into a mammal or human subject, it should stimulate the production of anti-anti-idiotypic antibodies, which should be specific to the 14094 protein. Vaccines directed to a disease characterized by 14094 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) Proc. Natl. Acad. Sci. USA 90:7889–7893).

The identified compounds that inhibit target gene expression, synthesis and/or activity can be administered to a patient at therapeutically effective doses to prevent, treat or ameliorate 14094 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 14094 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89–94 and in Shea, K. J. (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645–647. Through the use of isotope-labeling, the "free" concentration of compound which modulates the expression or activity of 14094 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142–2144.

Another aspect of the invention pertains to methods of modulating 14094 expression or activity for therapeutic purposes. Accordingly, in an exemplary embodiment, the modulatory method of the invention involves contacting a cell with a 14094 or agent that modulates one or more of the activities of 14094 protein activity associated with the cell. An agent that modulates 14094 protein activity can be an agent as described herein, such as a nucleic acid or a protein, a naturally-occurring target molecule of a 14094 protein (e.g., a 14094 substrate or receptor), a 14094 antibody, a 14094 agonist or antagonist, a peptidomimetic of a 14094 agonist or antagonist, or other small molecule.

In one embodiment, the agent stimulates one or 14094 activities. Examples of such stimulatory agents include active 14094 protein and a nucleic acid molecule encoding 14094. In another embodiment, the agent inhibits one or more 14094 activities. Examples of such inhibitory agents include antisense 14094 nucleic acid molecules, anti-14094 antibodies, and 14094 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 14094 protein or nucleic acid molecule. In one embodiment, the method involves administering an agent (e.g., an agent identified by a screening assay described herein), or combination of agents that modulates (e.g., up regulates or down regulates) 14094 expression or activity. In another embodiment, the method involves administering a 14094 protein or nucleic acid molecule as therapy to compensate for reduced, aberrant, or unwanted 14094 expression or activity.

Stimulation of 14094 activity is desirable in situations in which 14094 is abnormally downregulated and/or in which increased 14094 activity is likely to have a beneficial effect. For example, stimulation of 14094 activity is desirable in situations in which a 14094 is downregulated and/or in which increased 14094 activity is likely to have a beneficial effect. Likewise, inhibition of 14094 activity is desirable in situations in which 14094 is abnormally upregulated and/or in which decreased 14094 activity is likely to have a beneficial effect.

Pharmacogenomics

The 14094 molecules of the present invention, as well as agents, or modulators which have a stimulatory or inhibitory effect on 14094 activity (e.g., 14094 gene expression) as identified by a screening assay described herein can be administered to individuals to treat (prophylactically or therapeutically) 14094 associated disorders (e.g., cell proliferative or differentiative disorders, coagulative disorders, organogenesis disorders, complement activation disorders, hormone production disorders) associated with aberrant or unwanted 14094 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 14094 molecule or 14094 modulator as well as tailoring the dosage and/or therapeutic regimen of treatment with a 14094 molecule or 14094 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983–985 and Linder, M. W. et al. (1997) *Clin. Chem.* 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a 14094 protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a 14094 molecule or 14094 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 14094 molecule or 14094 modulator, such as a modulator identified by one of the exemplary screening assays described herein.

The present invention further provides methods for identifying new agents, or combinations, that are based on identifying agents that modulate the activity of one or more of the gene products encoded by one or more of the 14094 genes of the present invention, wherein these products may be associated with resistance of the cells to a therapeutic agent. Specifically, the activity of the proteins encoded by the 14094 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 14094 protein can be applied in clinical trials. For example, the effectiveness of an agent determined by a screening assay as described herein to increase 14094 gene expression, protein levels, or upregulate 14094 activity, can be monitored in clinical trials of subjects exhibiting decreased 14094 gene expression, protein levels, or downregulated 14094 activity. Alternatively, the effectiveness of an agent determined by a screening assay to decrease 14094 gene expression, protein levels, or downregulate 14094 activity, can be monitored in clinical trials of subjects exhibiting increased 14094 gene expression, protein levels, or upregulated 14094 activity. In such clinical trials, the expression or activity of a 14094 gene, and preferably, other genes that have been implicated in, for example, a 14094-associated disorder can be used as a "read out" or markers of the phenotype of a particular cell.

14094 Informatics

The sequence of a 14094 molecule is provided in a variety of media to facilitate use thereof. A sequence can be provided as a manufacture, other than an isolated nucleic acid or amino acid molecule, which contains a 14094. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 14094 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 14094, e.g., analyzing structure, function, or relatedness to one or more other nucleic acid or amino acid sequences. The method includes: providing a 14094 nucleic acid or amino acid sequence; comparing the 14094 sequence with a second sequence, e.g., one or more preferably a plurality of sequences from a collection of sequences, e.g., a nucleic acid or protein sequence database to thereby analyze 14094. The method can be performed in a machine, e.g., a computer, or manually by a skilled artisan.

The method can include evaluating the sequence identity between a 14094 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However; it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 14094 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 14094 sequence, or record, in machine-readable form; comparing a second sequence to the 14094 sequence; thereby analyzing a sequence. Comparison can include comparing to sequences for sequence identity or determining if one sequence is included within the other, e.g., determining if the 14094 sequence includes a sequence being compared. In a preferred embodiment the 14094 or second sequence is stored on a first computer, e.g., at a first site and the comparison is performed, read, or recorded on a second computer, e.g., at a second site. E.g., the 14094 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 14094-associated disease or disorder or a pre-disposition to a 14094-associated disease or disorder, wherein the method comprises the steps of determining 14094 sequence information associated with the subject and based on the 14094 sequence information, determining whether the subject has a 14094-associated disease or disorder or a pre-disposition to a 14094-associated disease or disorder and/or recommending a particular treatment for the disease, disorder or pre-disease condition.

The invention further provides in an electronic system and/or in a network, a method for determining whether a subject has a 14094-associated disease or disorder or a pre-disposition to a disease associated with a 14094 wherein the method comprises the steps of determining 14094 sequence information associated with the subject, and based on the 14094 sequence information, determining whether the subject has a 14094-associated disease or disorder or a pre-disposition to a 14094-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 14094 sequence of the subject to the 14094 sequences in the database to thereby determine whether the subject as a 14094-associated disease or disorder, or a pre-disposition for such.

The present invention also provides in a network, a method for determining whether a subject has a 14094 associated disease or disorder or a pre-disposition to a 14094-associated disease or disorder associated with 14094, said method comprising the steps of receiving 14094 sequence information from the subject and/or information related thereto, receiving phenotypic information associated with the subject, acquiring information from the network corresponding to 14094 and/or corresponding to a 14094-associated disease or disorder (e.g., a cell proliferative disorder), and based on one or more of the phenotypic information, the 14094 information (e.g., sequence information and/or information related thereto), and the acquired information, determining whether the subject has a 14094-associated disease or disorder or a pre-disposition to a 14094-associated disease or disorder. The method may further comprise the step of recommending a particular treatment for the disease, disorder or pre-disease condition.

The present invention also provides a method for determining whether a subject has a 14094-associated disease or disorder or a pre-disposition to a 14094-associated disease or disorder, said method comprising the steps of receiving information related to 14094 (e.g., sequence information and/or information related thereto), receiving phenotypic information associated with the subject, acquiring information from the network related to 14094 and/or related to a 14094-associated disease or disorder, and based on one or more of the phenotypic information, the 14094 information, and the acquired information, determining whether the subject has a 14094-associated disease or disorder or a pre-disposition to a 14094-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

EXAMPLES

Example 1

Identification and Characterization of Human 14094 cDNA

The human 14094 nucleic acid sequence is recited as follows:

```
                                                    (SEQ ID NO:1)
AAGAGTTGCATATCGCCTCCCATCAACAAACTTTCCNTGTATTTCCANAC

AATGTATTTTGTTTGTCAAATCCAGTTTTCTTGTAAACATTGGGGGTAA

ATAACAGAGGTGGCTTATGAGTATTTCTTCCAGGGTAAAAAGCAAAAGAA

TTCCGGTTTTCTGTATCCTTTTCACTTACTGTTACCCACTTTGCCTCGTC

TTCACCCTGTCCAAACACCGGTCTCCAATTTGCCCTTCAGAGAACTTAA

GTCAAGGAGAGTTGAAATTCACAGGCCAGGGCACATCTTTTATTTATTTC

ATTATGTTGGCCAACAGAACTTGATTGTAAATAATAATAAAGAAATCTGT

TATATACTTTCCAAACTCCAAAAAAAAACCGGAATTCAGCCTGGTTAAGT

CCAAGCTGAATTCCGGGTGGGGAAGGACCGGGCACCGGACGGCTCGGGT

ACTTTCGTTCTTAATTAGGTCATGCCCGTATGAGCCAGGAAAGGCTGTG

TTTATGGGAAGCCAGTAACACTGTGGCCTACTATCTCTTCCGTGGTGCCA

TCTACATTTTTGGGACTCGGGAATTATGAGGTAGAGGTGGAGGCGGAGCC

GGATGTCAGAGGTCCTGAAATAGTCACCATGGGGAAAATGATCCGCCTG

CTGTTGAAGCCCCCTTCTCATTCCGATCGCTTTTTGGCCTTGATGATTTG

AAAATAAGTCCTGTTGCACCAGATGCAGATGCTGTTGCTGCACAGATCCT

GTCACTGCTGCCATTGAAGTTTTTTCCAATCATCGTCATTGGGATCATTG

CATTGATATTAGCACTGGCCATTGGTCTGGGCATCCACTTCGACTGCTCA

GGGAAGTACAGATGTCGCTCATCCTTTAAGTGTATCGAGCTGATAGCTCG

ATGTGACGGAGTCTCGGATTGCAAAGACGGGGAGGACGAGTACCGCTGTG

TCCGGGTGGGTGGTCAGAATGCCGTGCTCCAGGTGTTCACAGCTGCTTCG

TGGAAGACCATGTGCTCCGATGACTGGAAGGGTCACTACGCAAATGTTGC

CTGTGCCCAACTGGGTTTCCCAAGCTATGTGAGTTCAGATAACCTCAGAG

TGAGCTCGCTGGAGGGGCAGTTCCGGGAGGAGTTTGTGTCCATCGATCAC

CTCTTGCCAGATGACAAGGTGACTGCATTACACCACTCAGTATATGTGAG

GGAGGGATGTGCCTCTGGCCACGTGGTTACCTTGCAGTGCACAGCCTGTG

GTCATAGAAGGGGCTACAGCTCACGCATCGTGGGTGGAAACATGTCCTTG

CTCTCGCAGTGGCCCTGGCAGGCCAGCCTTCAGTTCCAGGGCTACCACCT

GTGCGGGGCTCTGTCATCACGCCCCTGTGGATCATCACTGCTGCACACT

GTGTTTATGACTTGTACCTCCCCAAGTCATGGACCATCCAGGTGGGTCTA

GTTTCCCTGTTGGACAATCCAGCCCCATCCCACTTGGTGGAGAAGATTGT

CTACCACAGCAAGTACAAGCCAAAGAGGCTGGGCAATGACATCGCCCTTA

TGAAGCTGGCCGGGCCACTCACGTTCAATGAAATGATCCAGCCTGTGTGC

CTGCCCAACTCTGAAGAGAACTTCCCCGATGGAAAAGTGTGCTGGACGTC

AGGATGGGGGCCACAGAGGATGGAGGTGACGCCTCCCCTGTCCTGAACC

ACGCGGCCGTCCCTTTGATTTCCAACAAGATCTGCAACCACAGGGACGTG

TACGGTGGCATCATCTCCCCCTCCATGCTCTGCGCGGGCTACCTGACGGG

TGGCGTGGACAGCTGCCAGGGGGACAGCGGGGGGCCCCTGGTGTGTCAAG

AGAGGAGGCTGTGGAAGTTAGTGGGAGCGACCAGCTTTGGCATCGGCTGC

GCAGAGGTGAACAAGCCTGGGGTGTACACCCGTGTCACCTCCTTCCTGGA

CTGGATCCACGAGCAGATGGAGAGAGACCTAAAAACCTGAAAAGGAAGGG

GACAAGTAGCCACCTGAGTTCCTGAGGTGATGAAGACAGCCCGATCCTCC

CCTGGACTCCCGTGTAGGAACCTGCACACGAGCAGACACCCTTGGAGCTC

TGAGTTCCGGCACCAGTAGCAGGCCCGAAAGAGGCACCCTTCCATCTGAT

TCCAGCACAACCTTCAAGCTGCTTTTTGTTTTTTGTTTTTTTGAGATGGA

GTCTCGCTCTGTTGCCCAGGCTGGAGTGCAGTGGCGAAATCCCTGCTCAC

TGCAGCCTCCGCTTCCCTGGTTCAAGCGATTCTCTTGCCTCAGCTTCCCC

AGTAGCTGGGACCACAGGTGCCCGCCACCACACCCAACTAATTTTTGTAT

TTTTAGTAGAGACAGGGTTTCACCATGTTGGCCAGGCTGCTCTCAAACCC

CTGACCTCAAATGATGTGCCTGCTTCAGCCTCCCACAGTGCTGGGATTAC

AGGCATGGGCCACCACGCCTAGCCTCACGCTCCTTTCTGATCTTCACTAA

GAACAAAAGAAGCAGCAACTTGCAAGGGCGGCCTTTCCCACTGGTCCATC

TGGTTTTCTCTCCAGGGGTCTTGCAAAATTCCTGACGAGATAAGCAGTTA

TGTGACCTCACGTGCAAAGCCACCAACAGCCACTCAGAAAAGACGCACCA

GCCCAGAAGTGCAGAACTGCAGTCACTGCACGTTTTCATCTCTAGGGACC

AGAACCAAACCCACCCTTTCTACTTCCAAGACTTATTTTCACATGTGGGG

AGGTTAATCTAGGAATGACTCGTTTAAGGCCTATTTTCATGATTTCTTTG
```

-continued

```
TAGCATTTGGTGCTTGACGTATTATTGTCCTTTGATTCCAAATAATATGT

TTCCTTCCCTCATWRAAMAAAAAAAAAAAAAAAAAARRRMRRSSGCTAVAV

MARKTTAGAGAAAAAACCTACCCACRCCTTCCCCCTGAAMCTRAAAMYA
```

The nucleic acid sequence includes an initiation codon (ATG) and a termination codon (TGA) which are underscored above. The region between and inclusive of the initiation codon and the termination codon is a methionine-initiated coding sequence of about 1362 nucleotides, including the termination codon (nucleotides indicated as "coding" of SEQ ID NO:1; SEQ ID NO:3). The coding sequence encodes a 453 amino acid protein (SEQ ID NO:2), which is recited as follows:

```
                                          (SEQ ID NO:2)
MGENDPPAVEAPFSFRSLFGLDDDLKISPVAPDADAVAAQILSLLPLKFFP

IIIIGIIALILALAIGLGIHFDCSGKYRCRSSFKCIELIARCDGVSDCKD

GEDEYRCVRVGGQNAVLQVFTAASWKTMCSDDWKGHYANVACAQLGFPSY

VSSDNLRVSSLEGQFREEFVSIDHLLPDDKVTALHHSVYVREGCASGHVV

TLQCTACGHRRGYSSRIVGGNMSLLSQWPWQASLQFQGYHLCGGSVITPL

WIIITAAHCVYDLYLPKSWTIQVGLVSLLDNPAPSHLVEKIVYHSKYKPKR

LGNDIALMKLAGPLTFNEMIQPVCLPNSEENFPDGKVCWTSGWGATEDGG

DASPVLNHAAVPLISNKICNHRDVYGGIISPSMLCAGYLTGGVDSCQGDS

GGPLVCQERRLWKLVGATSFGIGCAEVNKPGVYTRVTSFLDWIHEQMERD

LKT.
```

Also featured is a second nucleotide sequence encoding a 14094 polypeptide (SEQ ID NO:11, as shown below). The sequence is recited as follows:

```
                                         (SEQ ID NO:11)
AAGAGTTGCATATCGCCTCCCATCAACAAACTTTCCNTGTATTTCCANAC

AATGTATTTTGTTTGTCAAATCCAGTTTTCTTGTAAAGATTGGGGGGTAA

ATAACAGAGGTGGCTTATGAGTATTTCTTCCAGGGTAAAAAGCAAAAGAA

TTCCGGTTTTCTGTATCCTTTTCACTTACTGTTACCCACTTTGCCTCGTC

TTCACCCTGTCCAAACACCGGTCTCCAATTTGCCCTTCAGAGAACTTAAG

TCAAGGAGAGTTGAAATTCACAGGCCAGGGCACATCTTTTATTTATTTCA

TTATGTTGGCCAACAGAACTTGATTGTAAATAATAATAAAGAAATCTGTT

ATATACTTTCCAAACTCCAAAAAAAAACCGGAATTCAGCCTGGTTAAGTC

CAAGCTGAATTCCGGGTGGGGAAGGACCGGGCACCGGACGGCTCGGGTA

CTTTCGTTCTTAATTAGGTCATGCCCGTATGAGCCAGGAAAGGGCTGTGT

TTATGGGAAGCCAGTAACACTGTGGCCTACTATCTCTTCCGTGGTGCCAT

CTACATTTTGGGACTCGGGAATTATGAGGTAGAGGTGGAGGCGGAGCCG

GATGTCAGAGGTCCTGAAATAGTCACCATGGGGAAAATGATCCGCCTGC

TGTTGAAGCCCCCTTCTCATTCCGATCGCTTTTTGGCCTTGATGATTTGA

AAATAAGTCCTGTTGCACCAGATGCAGATGCTGTTGCTGCACAGATCCTG

TCACTGCTGCCATTGAAGTTTTTTCCAATCATCGTCATTGGGATCATTGC

ATTGATATTAGCACTGGCCATTGGTCTGGGCATCCACTTCGACTGCTCAG

GGAAGTACAGATGTCGCTCATCCTTTAAGTGTATCGAGCTGATAGCTCGA

TGTGACGGAGTCTCGGATTGCAAAGACGGGGAGGACGAGTACCGCTGTGT

CCGGGTGGGTGGTCAGAATGCCGTGCTCCAGGTGTTCACAGCTGCTTCGT

GGAAGACCATGTGCTCCGATGACTGGAAGGGTCACTACGCAAATGTTGCC

TGTGCCCAACTGGGTTTCCCAAGCTATGTGAGTTCAGATAACCTCAGAGT

GAGCTCGCTGGAGGGGCAGTTCCGGGAGGAGTTTGTGTCCATCGATCACC

TCTTGCCAGATGACAAGGTGACTGCATTACACCACTCAGTATATGTGAGG

GAGGGATGTGCCTCTGGCCACGTGGTTACCTTGCAGTGCACAGCCTGTGG

TCATAGAAGGGGCTACAGCTCACGCATCGTGGGTGGAAACATGTCCTTGC

TCTCGCAGTGGCCCTGGCAGGCCAGCCTTCAGTTCCAGGGCTACCACCTG

TGCGGGGGCTCTGTCATCACGCCCCTGTGGATCATCACTGCTGCACACTG

TGTTTATGACTTGTACCTCCCCAAGTCATGGACCATCCAGGTGGGTCTAG

TTTCCCTGTTGGACAATCCAGCCCCATCCCACTTGGTGGAGAAGATTGTC

TACCACAGCAAGTACAAGCCAAAGAGGCTGGGCAATGACATCGCCCTTAT

GAAGCTGGCCGGGCCACTCACGTTCAATGAAATGATCCAGCCTGTGTGCC

TGCCCAACTCTGAAGAGAACTTCCCCGATGGAAAAGTGTGCTGGACGTCA

GGATGGGGGCCACAGAGGATGGAGCAGGTGACGCCTCCCCTGTCCTGAA

CCACGCGGCCGTCCCTTTGATTTCCAACAAGATCTGCAACCACAGGGACG

TGTACGGTGGCATCATCTCCCCCTCCATGCTCTGCGCGGGCTACCTGACG

GGTGGCGTGGACAGCTGCCAGGGGGACAGCGGGGGGCCCCTGGTGTGTCA

AGAGAGGAGGCTGTGGAAGTTAGTGGGAGCGACCAGCTTTGGCATCGGCT

GCGCAGAGGTGAACAAGCCTGGGGTGTACACCCGTGTCACCTCCTTCCTG

GACTGGATCCACGAGCAGATGGAGAGAGACCTAAAAACCTGAAGAGGAAG

GGGACAAGTAGCCACCTGAGTTTCCTGAGGTGATGAAGACAGCCCGATC

CTCCCCTGGACTCCCGTGTAGGAACCTGCACACGAGCAGACACCCTTGG

AGCTCTGAGTTCCGGCACCAGTAGCAGGCCCGAAAGAGGCACCCTTCCA

TCTGATTCCAGCACAACCTTCAAGCTGCTTTTTGTTTTTTGTTTTTTTG

AGATGGAGTCTCGCTCTGTTGCCCAGGCTGGAGTGCAGTGGCGAAATCC

CTGCTCACTGCAGCCTCCGCTTCCCTGGTTCAAGCGATTCTCTTGCCTC

AGCTTCCCCAGTAGCTGGGACCACAGGTGCCCGCCACCACACCCAACTA

ATTTTTGTATTTTTAGTAGAGACAGGGTTTCACCATGTTGGCCAGGCTG

CTCTCAAACCCCTGACCTCAAATGATGTGCCTGCTTCAGCCTCCCACAG

TGCTGGGATTACAGGCATGGGCCACCACGCCTAGCCTCACGCTCCTTTC

TGATCTTCACTAAGAACAAAAGAAGCAGCAACTTGCAAGGGCGGCCTTT

CCCACTGGTCCATCTGGTTTTCTCTCCAGGGGTCTTGCAAAATTCCTGA

CGAGATAAGCAGTTATGTGACCTCACGTGCAAAGCCACCAACAGCCACT

CAGAAAAGACGCACCAGCCCAGAAGTGCAGAACTGCAGTCACTGCACGT

TTTCATCTCTAGGGACCAGAACCAAACCCACCCTTTCTACTTCCAAGAC

TTATTTTCACATGTGGGGAGGTTAATCTAGGAATGACTCGTTTAAGGCC
```

-continued
TATTTTCATGATTTCTTTGTAGCATTTGGTGCTTGACGTATTATTGTCC

TTTGATTCCAAATAATATGTTTCCTTCCCTCATWRAAMAAAAAAAAAAA

AAAAAARRRMRRSSGCTAVAVMARKTTAGAGAAAAAACCTACCCACRCC

TTCCCCCTGAAMCTRAAAMYA.

The nucleic acid sequence shown in SEQ ID NO:11 includes an initiation codon (ATG) and a termination codon (TGA) which are underscored above. The region between and inclusive of the initiation codon and the termination codon is a methionine-initiated coding sequence of about 1365 nucleotides, including the termination codon (nucleotides indicated as "coding" of SEQ ID NO:11; SEQ ID NO:13). The coding sequence encodes the 454 amino acid protein of SEQ ID NO:12, recited as follows:

(SEQ ID NO:12)
MGENDPPAVEAPFSFRSLFGLDDLKISPVAPDADAVAAQILSLLPLKTTP

IIIIGIIALILALAIGLGIHFDCSGKYRCRSSFKCIELIARCDGVSDCKD

GEDEYRCVRVGGQNAVLQVFTAASWKTMCSDDWKGHYANVACAQLGFPSY

VSSDNLRVSSLEGQFREEFVSIDHLLPDDKVTALHHSVYVREGCASGHVV

TLQCTACGHRRGYSSRIVGGNMSLLSQWPWQASLQFQGYHLCGGSVITPL

WIITAAHCVYDLYLPKSWTIQVGLVSLLDNPAPSHLVEKIVYHSKYKPKR

LGNDIALMKLAGPLTFNEMIQPVCLPNSEENFPDGKVCWTSGWGATEDGA

GDASPVLNHAAVPLISNKICNHRDVYGGIISPSMLCAGYLTGGVDSCQGD

SGGPLVCQERRLWKLVGATSFGIGCAEVNKPGVYTRVTSFLDWIHEQMER

DLKT.

Example 2

Tissue Distribution of 14094 mRNA by TAQMAN® Analysis

Endogenous human 14094 gene expression was determined using the Perkin-Elmer/ABI 7700 Sequence Detection System which employs TAQMAN® technology. Briefly, TAQMAN® technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH which has been labeled with a different fluorophore on the 5' end (typically VIC).

To determine the level of 14094 in various human tissues a primer/probe set was designed. Total RNA was prepared from a series of human tissues using an RNeasy kit from Qiagen. First strand cDNA was prepared from 1 μg total RNA using an oligo-dT primer and Superscript II reverse transcriptase (Gibco/BRL). cDNA obtained from approximately 50 ng total RNA was used per TAQMAN® reaction. Tissues tested include the human tissues and several cell lines shown in Tables 3–6.

TABLE 3

| Sample | Relative Expression |
| --- | --- |
| Aorta/normal | 0.02 |
| Fetal heart/normal | 0.00 |
| Heart normal | 0.00 |
| Heart/CHF | 0.00 |
| Vein/Normal | 0.00 |
| SMC (Aortic) | 0.00 |
| Spinal cord/Normal | 0.01 |
| Brain cortex/Normal | 0.06 |
| Brain hypothalamus/Normal | 0.02 |
| Glial cells (Astrocytes) | 0.00 |
| Brain/Glioblastoma | 0.00 |
| Breast/Normal | 0.06 |
| Breast tumor/IDC | 0.10 |
| OVARY/Normal | 0.01 |
| OVARY/Tumor | 0.08 |
| Pancreas | 0.00 |
| Prostate/Normal | 0.00 |
| Prostate/Tumor | 0.00 |
| Colon/normal | 0.00 |
| Colon/tumor | 0.07 |
| Colon/IBD | 0.00 |
| Kidney/normal | 0.03 |
| Liver/normal | 0.00 |
| Liver fibrosis | 0.02 |
| Fetal Liver/normal | 0.01 |
| Lung/normal | 0.00 |
| Lung/tumor | 0.01 |
| Lung/COPD | 0.01 |
| Spleen/normal | 0.00 |
| Tonsil/normal | 0.00 |
| Lymph node/normal | 0.00 |
| Thymus/normal | 0.01 |
| Epithelial Cells (prostate) | 0.00 |
| Endothelial Cells (aortic) | 0.00 |
| Skeletal Muscle/Normal | 0.00 |
| Fibroblasts (Dermal) | 0.00 |
| Skin/normal | 0.01 |
| Adipose/Normal | 0.00 |
| Osteoblasts (primary) | 0.00 |
| Osteoblasts (Undiff) | 0.00 |
| Osteoblasts (Diff) | 0.00 |
| Osteoclasts | 0.00 |
| Aorta SMC (Early) | 0.00 |
| Aorta SMC (Late) | 0.00 |
| HUVEC | 0.00 |
| HMVEC | 0.00 |

TABLE 4

| Sample | Relative Expression |
| --- | --- |
| IDC | 0.0 |
| IDC | 0.0 |
| IDC | 0.0 |
| IDC | 0.0 |
| IDC | 0.7 |
| DCIS/IDC | 2.5 |
| DCIS/IDC | 2.1 |
| DCIS/IDC | 0.8 |
| DCIS/IDC | 0.2 |
| DCIS/IDC | 0.0 |
| Breast Normal | 0.6 |
| Breast Normal | 0.6 |
| Breast Normal | 0.0 |
| Breast Normal | 0.2 |
| Colon Normal | 0.5 |
| Colon Normal | 0.0 |
| Colon Adenoma | 0.0 |

TABLE 4-continued

| Sample | Relative Expression |
|---|---|
| Colon Adenoma | 0.0 |
| Colon Adenoma | 0.0 |
| Colon Adenoma | 0.5 |
| Colon Adenoma | 0.7 |
| Colon Metastasis | 0.0 |
| Colon Metastasis | 0.2 |
| Colon Metastasis | 0.7 |
| Colon Metastasis | 2.7 |
| Colon Metastasis | 0.0 |
| Liver Normal | 1.2 |
| Liver Normal | 0.1 |
| Lung Normal | 0.0 |
| Lung Normal | 0.0 |
| Lung Normal | 0.3 |
| Lung Tumor | 0.7 |
| Lung Tumor | 0.3 |
| Lung Tumor | 1.0 |
| Lung Tumor | 0.0 |
| Brain Normal | 0.4 |
| Brain Normal | 4.7 |
| Glioma | 0.0 |
| Glioma | 0.0 |
| Glioma | 0.0 |

(IDC = invasive ductal carcinoma)

TABLE 5

| Sample | Relative Expression |
|---|---|
| PIT 337 Colon Normal | 0.00 |
| CHT 410 Colon Normal | 0.03 |
| CHT 425 Colon Normal | 0.05 |
| CHT 371 Colon Normal | 0.11 |
| PIT 281 Colon Normal | 0.00 |
| NDR 211 Colon Normal | 0.04 |
| CHT 122 Adenomas | 0.19 |
| CHT 887 Adenomas | 0.52 |
| CHT 414 Colonic adenocarcinoma-B | 0.51 |
| CHT 841 Colonic adenocarcinoma-B | 2.98 |
| CHT 890 Colonic adenocarcinoma-B | 0.92 |
| CHT 910 Colonic adenocarcinoma-B | 0.64 |
| CHT 807 Colonic adenocarcinoma-B | 0.16 |
| CHT 382 Colonic adenocarcinoma-B | 4.96 |
| CHT 377 Colonic adenocarcinoma-B | 0.31 |
| CHT 520 Colonic adenocarcinoma-C | 0.86 |
| CHT 596 Colonic adenocarcinoma-C | 0.37 |
| CHT 907 Colonic adenocarcinoma-C | 0.71 |
| CHT 372 Colonic adenocarcinoma-C | 0.37 |
| NDR 210 Colonic adenocarcinoma-C | 7.63 |
| CHT 1365 Colonic adenocarcinoma-C | 0.20 |
| CLN 740 Liver Normal | 0.18 |
| CLN 741 Liver Normal | 0.37 |
| NDR 165 Liver Normal | 1.61 |
| NDR 150 Liver Normal | 0.41 |
| PIT 236 Liver Normal | 0.27 |
| CHT 1878 Liver Normal | 0.08 |
| CHT 077 Colon Liver Metastasis | 1.87 |
| CHT 119 Colon Liver Metastasis | 0.25 |
| CHT 131 Colon Liver Metastasis | 0.27 |
| CHT 218 Colon Liver Metastasis | 1.16 |
| CHT 739 Colon Liver Metastasis | 1.09 |
| CHT 755 Colon Liver Metastasis | 0.89 |
| CHT 215 Colon Abdominal Metastasis | 1.73 |

TABLE 6

| Sample | Relative Expression |
|---|---|
| PIT 400 Breast Normal | 11.97 |
| PIT 372 Breast Normal | 12.09 |
| CHT 558 Breast Normal | 0.28 |
| CLN 168 Breast Tumor: IDC | 11.40 |
| MDA 304 Breast Tumor: MD-IDC | 10.31 |

TABLE 6-continued

| Sample | Relative Expression |
|---|---|
| NDR 58 Breast Tumor: IDC | 2.67 |
| NDR 05 Breast Tumor: IDC | 3.45 |
| CHT 562 Breast Tumor: IDC | 59.13 |
| NDR 12 Breast Tumor | 1.45 |
| PIT 208 Ovary Normal | 0.32 |
| CHT 620 Ovary Normal | 0 |
| CLN 03 Ovary Tumor | 6.90 |
| CLN 17 Ovary Tumor | 86.27 |
| MDA 25 Ovary Tumor | 129.86 |
| MDA 216 Ovary Tumor | 4.07 |
| CLN 012 Ovary Tumor | 38.08 |
| MDA 185 Lung Normal | 0 |
| CLN 930 Lung Normal | 0.47 |
| MDA 183 Lung Normal | 0.42 |
| MPI 215 Lung Tumor--SmC | 3.04 |
| MDA 259 Lung Tumor-PDNSCCL | 20.12 |
| CHT 832 Lung Tumor-PDNSCCL | 0.39 |
| MDA 253 Lung Tumor-PDNSCCL | 0.10 |
| MDA 262 Lung Tumor-SCC | 0.74 |
| CHT 211 Lung Tumor-AC | 1.25 |
| CHT 793 Lung Tumor-ACA | 0.17 |
| CHT 396 Colon Normal | 0 |
| CHT 523 Colon Normal | 0 |
| CHT 452 Colon Normal | 0.02 |
| CHT 382 Colon Tumor: MD | 6.57 |
| CHT 528 Colon Tumor: MD | 6.59 |
| CLN 609 Colon Tumor | 4.23 |
| CHT 372 Colon Tumor: MD-PD | 0.48 |
| CHT 340 Colon-Liver Metastasis | 2.65 |
| NDR 100 Colon-Liver Metastasis | 1.15 |
| PIT 260 Liver Normal (female) | 0.02 |
| ONC 102 Hemangioma | 0 |
| A24 HMVEC-Arr | 0 |
| C48 HMVEC-Prol | 0 |

(PDNSCCL = poorly differentiated non small cell carcinoma of the lung; SCC = small cell carcinoma)

TABLE 7

| Sample | | Relative Expression |
|---|---|---|
| CLN 630 | Breast N | 0.1 |
| CLN 736 | Breast N | 0.0 |
| PIT 265 | Breast N | 0.1 |
| NDR 13 | Breast N | 0.4 |
| NDR 1 | Breast T | 0.3 |
| NDR 12 | Breast T | 0.1 |
| NDR 57 | Breast T | 0.2 |
| NDR 58 | Breast T | 0.2 |
| NDR 136 | Breast T | 0.3 |
| NDR 7 | Breast T | 0.0 |
| PIT 208 | Ovary N | 0.0 |
| MDA 59 | Ovary N | 0.0 |
| CLN 355 | Ovary N | 0.0 |
| CLN 3 | Ovary T | 0.3 |
| CLN 5 | Ovary T | 0.2 |
| CLN 6 | Ovary T | 1.4 |
| CLN 7 | Ovary T | 0.4 |
| CLN 8 | Ovary T | 0.3 |
| MDA 216 | Ovary T | 0.1 |
| CLN 12 | Ovary T | 0.7 |
| CLN 15 | Ovary T | 3.0 |
| PIT 270 | Lung N | 0.1 |
| NDR 42 | Lung N | 0.0 |
| NDR 185 | Lung N | 0.0 |
| CHT 816 | Lung N | 0.0 |
| CHT 814 | Lung T | 0.0 |
| MPI 215 | Lung T | 0.3 |
| CHT 911 | Lung T | 0.0 |
| CHT 726 | Lung T | 0.0 |
| MDA 259 | Lung T | 0.7 |
| CHT 845 | Lung T | 0.2 |
| CHT 832 | Lung T | 0.0 |
| CHT 211 | Lung T | 0.1 |

Normal tissues tested included the human tissues provided in Table 3, including fetal heart, brain, ovary, colon, lung, kidney, liver, skin, and aorta, among others. Elevated expression was found primarily in ovary, breast, and colon tumors (Table 3).

Expression of 14094 was compared in normal and tumor cells derived from several tissues (Table 4). Increased expression of 14094 was seen in some breast tumors when compared to normal breast tissue. Increased expression of 14094 was also seen in some lung tumors when compared to normal lung tissue. Increased expression of 14094 was also seen in colon tumors and in metastatic colon tumors when compared to normal colon tissue.

The mRNA expression data for 14094 mRNA in Table 5 indicated that 14094 mRNA was over-expressed relative to normal tissues in a number of colonic adenocarcinoma samples, some colon liver metastases, and a colon abdominal metastasis.

The mRNA expression data for 14094 mRNA in Table 6 and 7 indicated that 14094 mRNA was over-expressed relative to normal tissues in some breast tumor samples, including an invasive ductal carcinoma, some ovarian tumors, some colon tumors, some colon metastases, and some lung tumors, including a poorly differentiated non-small cell carcinoma.

TABLE 8

In Situ Hybridization

| Specimen # | Tissue | Diagnosis | Results: |
|---|---|---|---|
| CHT 814 | Lung | Normal | – |
| NDR 44 | Lung | Normal | + |
| PIT 296 | Lung | Normal | + |
| CHT 446 | Lung | Tumor-Adenocarcinoma | +++ |
| MDA 585 | Lung | Tumor-Adenocarcinoma | – |
| CHT 800 | Lung | Tumor-SCC | – |
| CHT 799 | Lung | Tumor-SCC | – |
| CLN 100 | Breast | Normal | +/– |
| CLN 98 | Breast | Normal | +/– |
| MDA 161 | Breast | Tumor-IDC | +++ |
| NDR 57 | Breast | Tumor-IDC | – |
| NDR 19 | Breast | Tumor-IDC | +/+++ |
| MDA 155 | Breast | Tumor-IDC | – |
| CLN 186 | Breast | Tumor-DCIS | +++ |
| NDR 124 | Colon | Tumor | – |
| NDR 99 | Colon | Tumor | – |
| MDA 61 | Ovary | Normal | – |
| CLN 350 | Ovary | Cystadenoma | + |
| CLN 346 | Ovary | Tumor-Mucinous Stage 1 | + |

The incidence of tumor associated expression of 14094 in tumors of the breast, lung, colon and ovary was evaluated by in situ hybridization (Table 8). High expression of 14094 was detected in breast tumor cells (expression in 0/2 normal samples and expression in 3/5 tumor samples) and in a lung adenocarcinoma.

Example 3

Tissue Distribution of 14094 mRNA by Northern Analysis

Northern blot hybridizations with various RNA samples can be performed under standard conditions and washed under stringent conditions, i.e., 0.2×SSC at 65° C. A DNA probe corresponding to all or a portion of the 14094 cDNA (SEQ ID NO:1 or 11) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 4

Recombinant Expression of 14094 in Bacterial Cells

In this example, 14094 is expressed as a recombinant glutathione-S-transferase (GST) fusion polypeptide in *E. coli* and the fusion polypeptide is isolated and characterized. Specifically, 14094 is fused to GST and this fusion polypeptide is expressed in *E. coli*, e.g., strain PEB199. Expression of the GST-14094 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 5

Expression of Recombinant 14094 Protein in COS Cells

To express the 14094 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 14094 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 14094 DNA sequence is amplified by PCR using two primers. The 5' primer contains the restriction site of interest followed by approximately twenty nucleotides of the 14094 coding sequence starting from the initiation codon; the 3' end sequence contains complementary sequences to the other restriction site of interest, a translation stop codon, the HA tag or FLAG tag and the last 20 nucleotides of the 14094 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 14094_gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 14094-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) *Molecular Cloning: A Laboratory Manual. 2nd, ed., Cold Spring*

Harbor Laboratory, Cold Spring Harbor Laboratory Press, Cold Spring Harbor, N.Y. The expression of the 14094 polypeptide is detected by radiolabelling ($^{35}$S-methionine or $^{35}$S-cysteine available from NEN, Boston, Mass., can be used) and immunoprecipitation (Harlow, E. and Lane, D. (1988) *Antibodies: A Laboratory Manual*, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 14094 coding sequence is cloned directly into the polylinker of the pCDNA/Amp vector using the appropriate restriction sites. The resulting plasmid is transfected into COS cells in the manner described above, and the expression of the 14094 polypeptide is detected by radiolabelling and immunoprecipitation using a 14094 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a candidate compound capable of interacting with a polypeptide selected from the group consisting of:
   a) a polypeptide comprising the amino acid sequence of SEQ ID NO:2; and
   b) a polypeptide encoded by a nucleic acid molecule comprising the nucleotide sequence of SEQ ID NO:1 or SEQ ID NO:3;
the method comprising:
   i) contacting a sample comprising the polypeptide with a test compound under conditions suitable for interaction; and
   ii) determining whether the polypeptide interacts with the test compound;
   thereby identifying a compound capable of interacting with the polypeptide.

2. The method of claim 1, wherein the sample is an isolated polypeptide, a membrane-bound form of an isolated polypeptide or a cell comprising the polypeptide.

3. The method of claim 1, wherein the cell is a mammalian cell.

4. The method of claim 1, wherein the interaction is in vitro.

5. The method of claim 1, wherein the candidate compound is selected from the group consisting of a peptoid, a peptidomimetic, a peptide, a phosphopeptide, an antibody, an organic molecule, and an inorganic molecule.

6. The method of claim 1, wherein the candidate compound is selected from the group consisting of: L-1-Chloro-3-tosylamido-4-phenyl-2-butanone, Soybean inhibitor, benzamidine, p-Nitrophenyl-p-guanidino benzoate, Tosyl-L-lysine chloromethyl ketone, and Tosyl-L-arginine chloromethyl ketone.

7. The method of claim 1, wherein the candidate compound is a member of a biological library.

8. The method of claim 1, wherein the candidate compound is detectably labeled.

9. The method of claim 8, wherein the label is selected from the group consisting of enzymes, prosthetic groups, fluorescent materials, luminescent materials, bioluminescent materials and radioactive materials.

10. The method of claim 1, wherein the candidate compound is attached to a bead.

11. The method of claim 1, wherein the interaction of the candidate compound with the polypeptide is detected by a method selected from the group consisting of:
   a) direct detection of test compound/polypeptide binding;
   b) a competition binding assay;
   c) an immunoassay; and
   d) a yeast two-hybrid assay.

* * * * *